US010119927B2

(12) United States Patent
Naidu et al.

(10) Patent No.: US 10,119,927 B2
(45) Date of Patent: Nov. 6, 2018

(54) ANALYTE ION DETECTION METHOD AND DEVICE

(75) Inventors: Ravendra Naidu, Mawson Lakes (AU);
Liang Wang, Mawson Lakes (AU);
Zuliang Chen, Mawson Lakes (AU);
Megharaj Mallavarapu, Mawson Lakes (AU)

(73) Assignee: CRC CARE PTY LTD, Adelaide (AU)

( * ) Notice: Subject to any disclaimer, the term of this patent is extended or adjusted under 35 U.S.C. 154(b) by 1088 days.

(21) Appl. No.: 13/997,123

(22) PCT Filed: Dec. 22, 2011

(86) PCT No.: PCT/AU2011/001663
§ 371 (c)(1),
(2), (4) Date: Jul. 30, 2013

(87) PCT Pub. No.: WO2012/083371
PCT Pub. Date: Jun. 28, 2012

(65) Prior Publication Data
US 2013/0304395 A1    Nov. 14, 2013

(30) Foreign Application Priority Data
Dec. 23, 2010   (AU) ................. 2010905647

(51) Int. Cl.
*G01N 31/00*     (2006.01)
*G01N 27/00*     (2006.01)
(Continued)

(52) U.S. Cl.
CPC ........... *G01N 27/00* (2013.01); *G01N 27/333* (2013.01); *G06N 3/084* (2013.01); *G06N 3/126* (2013.01)

(58) Field of Classification Search
CPC .............................. G01N 27/00; G01N 27/333
(Continued)

(56) References Cited

U.S. PATENT DOCUMENTS

| 2003/0237058 | A1* | 12/2003 | Burghaus ............... G06F 17/50 702/81 |
| 2005/0267377 | A1* | 12/2005 | Marossero ......... A61B 5/02411 600/511 |
| 2010/0222224 | A1* | 9/2010 | Suni ................... G01N 33/5438 506/8 |

OTHER PUBLICATIONS

Baret et al., Application of neural network calibrations to an halide ISE array, Talanta, vol. 51, Issue 5, Apr. 28, 2000, pp. 863-877.*
(Continued)

*Primary Examiner* — Toan Le
*Assistant Examiner* — Xiuquin Sun
(74) *Attorney, Agent, or Firm* — Mintz, Levin, Cohn, Ferris, Glovsky and Popeo, P.C.

(57) ABSTRACT

A method of assessing concentration of analyte ion(s) in a liquid can include contacting the liquid with a plurality of electrodes, each of which is configured to generate a signal in response to sensing a selected ion in the liquid. The signal received from each of the electrodes can be processed using a neural network algorithm trained to calculate ion interference between the selected ion and other ions in the liquid sensed at one of the electrodes and/or electrode interference between ones of the electrodes sensing a same selected ion based on a result of a comparison of training data. The ion interference and/or electrode interference can be compensated for, and the concentration of the analyte ion(s) in the liquid can be assessed on the basis of a compensated output from the neural network algorithm.

15 Claims, 20 Drawing Sheets

(51) Int. Cl.
  *G01N 27/333* (2006.01)
  *G06N 3/12* (2006.01)
  *G06N 3/08* (2006.01)
(58) Field of Classification Search
  USPC .......................................................... 702/25
  See application file for complete search history.

(56) References Cited

OTHER PUBLICATIONS

Postolache, et al., "Increasing Ion Selective Electrodes Performance Using Neural Networks", Sicon/02—Sensors for Industry Conference, Houston, Texas, USA, Nov. 19-21, 2002, pp. 127-132.
PCT International Search Report dated Mar. 7, 2012 for PCT application No. PCT/AU2011/001663.
Baret, M. et al. (Apr. 28, 2000). "Application of neural network calibrations to an halide ISE array," *Talanta* 51(5):863-877.
Ciosek, P. et al. (Jul. 2004, e-published Jun. 8, 2004). "Polymeric membrane ion-selective and cross-sensitive electrode-based electronic tongue for qualitative analysis of beverages," Analyst 129(7):639-644.
European Search Report dated Dec. 7, 2016, for EP Application No. EP 11851213.6, 10 pages.
Men, H. et al. (2010). "Optimizatin of Sensor Array Data with Various Pattern Recognition Techniques," *Applied Mechanics and Materials* 20-23:694-699.

\* cited by examiner

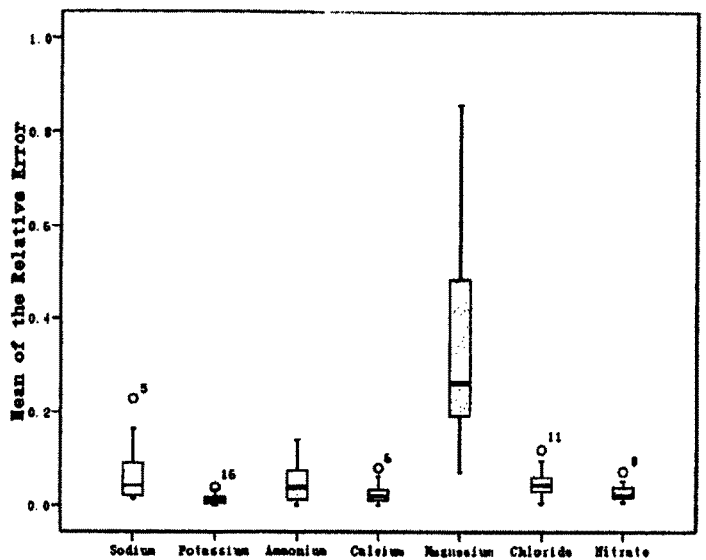

FIG. 12

| | M.Lakes.1 | | | | M.Lakes.2 | | | | River Torrens | | | |
|---|---|---|---|---|---|---|---|---|---|---|---|---|
| | ISE (10ˣ mol/L) | | ICP/IC (10ˣ mol/L) | | ISE (10ˣ mol/L) | | ICP/IC (10ˣ mol/L) | | ISE (10ˣ mol/L) | | ICP/IC (10ˣ mol/L) | |
| Na+ | -1.32 | ±5.1% | -1.23 | ±0.5% | -1.3 | ±7.4% | -1.31 | ±0.7% | -1.98 | ±5.1% | -2.13 | ±0.5% |
| K+ | -3.06 | ±1.2% | -3.09 | ±1.0% | -2.99 | ±0.2% | -2.95 | ±0.1% | -3.67 | ±0.3% | -3.6 | ±0.01% |
| NH4+ | -4.4 | ±1.3% | N/A | | -4.36 | ±1.1% | N/A | | -4.67 | ±1.3% | N/A | |
| Ca2+ | -3.27 | ±2.2% | -3.38 | ±0.2% | -3.54 | ±2.1% | -3.82 | ±0.2% | -2.93 | ±3.6% | -2.84 | ±0.2% |
| Mg2+ | -3.21 | ±0.4% | -2.64 | ±2% | -3.86 | ±0.3% | -2.69 | ±1.4% | -1.12 | ±34% | -4 | ±0.8% |
| Cl- | -1.36 | ±13% | -1.36 | ±0.6% | -1.44 | ±17.8% | -1.4 | ±0.2% | -1.8 | ±11.8% | -2.04 | ±0.1% |
| NO3- | -3.4 | ±3.7% | -3.21 | ±1.3% | -3.32 | ±3.5% | -3.04 | ±2.3% | -3.77 | ±0.5% | -3.6 | ±11.1% |
| | ISE (mg/L) | | ICP/IC (mg/L) | | ISE (mg/L) | | ICP/IC (mg/L) | | ISE (mg/L) | | ICP/IC (mg/L) | |
| Na+ | 1100.8 | ±126.3 | 1130 | ±15.3 | 1152.7 | ±150.3 | 1221 | ±9 | 247 | ±43.1 | 172.5 | |
| K+ | 34 | ±4.1 | 31.7 | ±6.3 | 39.9 | ±4.0 | 44.7 | ±1.4 | 8.3 | ±0.5 | 16.4 | ±0.1 |
| NH4+ | 0.7 | ±0.1 | N/A | | 0.8 | ±0.1 | N/A | | 0.4 | ±0.1 | N/A | |
| Ca2+ | 21.5 | ±3.4 | 16.7 | ±2 | 11.4 | ±1.3 | 4.3 | ±4 | 47 | ±6.1 | 38.3 | ±18 |
| Mg2+ | 3.83 | ±6.3 | 44.5 | ±4.5 | 1.8 | ±0.9 | 54.6 | ±1.5 | 36.1 | ±11.3 | 22 | ±2.5 |
| Cl- | 1547.4 | ±31.2 | 1536.3 | ±18.3 | 1287.1 | ±43.6 | 1410.5 | ±9.2 | 561.8 | ±67.9 | 320.6 | ±2 |
| NO3- | 24.7 | ±2.8 | 41.3 | ±2.3 | 26.1 | ±3.4 | 64.8 | ±9.3 | 10.5 | ±0.8 | 47.86 | ±6.3 |

FIG. 13

| Ion | Ion-selective Electrodes | | | | | | |
|---|---|---|---|---|---|---|---|
| | Sodium | Potassium | Ammonium | Calcium | W. H.* | Chloride | Nitrate |
| Na | — | -0.06 | -0.05 | -0.01 | -0.03 | -0.08 | -0.04 |
| K | -0.14 | — | 0.26 | 0.01 | -0.04 | -0.04 | 0.02 |
| $NH_4$ | -0.09 | 0.10 | — | 0.01 | -0.04 | -0.09 | 0.01 |
| Ca | 0.02 | -0.01 | -0.01 | — | — | -0.06 | -0.02 |
| Mg | -0.01 | 0.01 | 0.02 | 0.05 | 0.14 | -0.06 | 0.02 |
| Cl | 0.08 | 0.08 | 0.18 | 0.17 | 0.11 | — | -0.17 |
| $NO_3$ | 0.04 | -0.01 | -0.07 | -0.02 | -0.03 | 0.07 | — |

*- Water Hardness ISE

FIG. 16

| Ion | Mawson Lakes.1 | | | | Mawson Lakes.2 | | | | River Torrens | | | |
|---|---|---|---|---|---|---|---|---|---|---|---|---|
| | ISE ($10^x$ mol/L) | | ICP/IC ($10^x$ mol/L) | | ISE ($10^x$ mol/L) | | ICP/IC ($10^x$ mol/L) | | ISE ($10^x$ mol/L) | | ICP/IC ($10^x$ mol/L) | |
| $Na^+$ | -1.32 | ±5.1% | -1.23 | ±0.5% | -1.3 | ±7.4% | -1.31 | ±0.7% | -1.98 | ±5.1% | -2.13 | ±0.5% |
| $K^+$ | -3.06 | ±1.2% | -3.09 | ±1.0% | -2.99 | ±0.2% | -2.95 | ±0.1% | -3.67 | ±0.3% | -3.6 | ±0.01% |
| $NH_4^+$ | -4.4 | ±1.3% | N/A | | -4.36 | ±1.1% | N/A | | -4.67 | ±1.3% | N/A | |
| $Ca^{2+}$ | -3.27 | ±2.2% | -3.38 | ±0.2% | -3.54 | ±2.1% | -3.82 | ±0.2% | -2.93 | ±3.6% | -2.84 | ±0.2% |
| $Mg^{2+}$ | -3.21 | ±0.4% | -2.64 | ±2% | -3.86 | ±0.3% | -2.69 | ±1.4% | -1.12 | ±34% | -4 | ±0.8% |
| $Cl^-$ | -1.36 | ±13% | -1.36 | ±0.6% | -1.44 | ±17.8% | -1.4 | ±0.2% | -1.8 | ±11.8% | -2.04 | ±0.1% |
| $NO_3^-$ | -3.4 | ±3.7% | -3.21 | ±1.3% | -3.32 | ±3.5% | -3.04 | ±2.3% | -3.77 | ±0.5% | -3.6 | ±11.1% |

FIG. 19

| Ion | Ion-selective Electrodes | | | | | | | |
|---|---|---|---|---|---|---|---|---|
| | K | NH4 | Ca | Na | EC | Cl | NO3 | Cobalt |
| K | -- | 0.23 | ## | ## | 0.07 | ## | ## | ## |
| NH₄ | ## | -- | ## | ## | -0.09 | -0.08 | -0.07 | ## |
| Ca | 0.10 | 0.13 | -- | 0.18 | 0.24 | 0.08 | 0.15 | 0.22 |
| Na | 0.39** | 0.40** | 0.47** | -- | 0.63** | ## | 0.20 | 0.23 |
| Mg | 0.07 | ## | 0.07 | 0.07 | ## | -0.10 | ## | 0.16 |
| Cl | ## | ## | ## | ## | 0.68** | -- | 0.37** | 0.60** |
| NO₃ | ## | 0.09 | ## | 0.18 | 0.21 | 0.22 | -- | 0.07 |
| H₂PO₄ | 0.08 | 0.10 | 0.08 | -0.15 | -0.45** | 0.36** | 0.13 | -- |

\*\*-severe interference

- selectivity coefficient K < 0.05

FIG. 20

ANALYTE ION DETECTION METHOD AND DEVICE

CROSS REFERENCE TO RELATED APPLICATIONS

This application is a national stage application, filed under 35 U.S.C. § 371, of PCT Application No. PCT/AU2011/001663, filed on Dec. 22, 2011, and claims priority to Australian Patent Application No. 2010905647, filed on Dec. 23, 2010, the contents of which are incorporated herein by reference in their entirety for all purposes.

FIELD

The present invention relates to a method and device for assessing the concentration of at least one analyte ion in a liquid. Aspects of the present invention relate to the assessment of the concentration of an analyte ion in a liquid containing multiple ions.

BACKGROUND

Classical chemical analytical instruments, such as High-performance Liquid Chromatography (HPLC), Gas Chromatography (GC), Capillary Electrophoresis (CE) and Plasma Atomic Emission Spectrometry (PAES) have been used to assess concentration of ions in an environment. However, these instruments are expensive, not very portable and require considerable preparation and analysis time to assess concentrations, and thus are not suited to being deployed in real time, in situ applications. Such applications include, for example, food quality control in the food industry, nutrient monitoring in the agricultural sector and industrial pollution assessment for environmental monitoring.

In an example, assessment of water quality is important in a range of industries including agronomy, horticulture, waste water management, and nutrient monitoring of freshwater waterways and reservoirs. Examples of water quality assessment in agronomy/horticulture include: nutrient monitoring for a wide range of vegetable crops; hydroponic farming; irrigation water quality analysis; irrigation water discharge security; and soil structure and quality analysis.

Current water quality assessment methods require users to collect samples, send them to a laboratory, and wait several days for the results. This process is time consuming, costly, inefficient and does not allow for real time monitoring of water quality.

While commercial Ion Selective Electrodes (ISEs) have the capacity to provide rapid and quantitative analysis of an ion in solution, these existing ISEs have been limited by their inability to provide accurate readings of mixed ion samples. Ion Selective Electrodes (ISEs) are normally co-reactive which means that one ISE responds to similar analyte ions in solution and many ISEs in an array of ISEs respond to the same analyte ion. Interference from the other undesired analytes, which are similar to the desired one, constitutes one problem faced when ion-selective electrodes are used. In one example, attempts have been made to minimise interference by removing interfering analytes from the solution by chemical precipitations. However, the chemicals used might not be able to remove all the undesired analytes and also can introduce further interference. In another example, to avoid disturbing the natural speciation of the solution using chemicals, analysis can be done using the co-reactive electrode sensor array data directly using computational methods. However, the accuracy of these methods is still far from satisfying the requirements for, say, simultaneous determination of multiple chemical compositions, especially in complex mixtures of ions.

It is therefore desirable to provide a method and/or device that is able to rapidly and reliably assess concentrations of ions in a mixed ion solution.

Reference to any prior art in this specification is not, and should not be taken as, an acknowledgment or any form of suggestion that this prior art forms part of the common general knowledge in any country.

SUMMARY

In one aspect, the present invention provides a method of assessing concentration of at least one analyte ion in a liquid, the method including contacting the liquid with a plurality of electrodes, each of which is configured to generate a signal in response to sensing a selected ion in the liquid; receiving the signal from each of the electrodes; processing the signal from each of the electrodes using a neural network algorithm residing on a processor that has been trained to calculate ion interference between the selected ion and other ions in the liquid sensed at one of the electrodes and/or electrode interference between ones of the electrodes sensing a same selected ion based on a result of a comparison of training data indicative of a known ionic concentration applied to the neural network algorithm and the known ionic concentration; compensating for said ion interference and/or said electrode interference; and assessing the concentration of the at least analyte ion in the liquid on the basis of a compensated output from the neural network algorithm. In another aspect, the present invention also provides a device for assessing the concentration of an analyte ion in a liquid according to the above method. The device including a plurality of electrodes each of which generate a signal in response to sensing a selected ion in the liquid; and a data processing unit implementing a neural network algorithm that has been trained to calculate ion interference between the selected ion and other ions in the liquid sensed at one of the electrodes and/or electrode interference between ones of the electrodes sensing a same selected ion based on a result of a comparison of training data indicative of a known ionic concentration applied to the neural network algorithm and the known ionic concentration, wherein a signal generated by each electrode is received by the data processing unit and is processed by the neural network algorithm, and wherein the data processing unit compensates for said ion interference and/or said electrode interference and assesses the concentration of the at least one analyte ion in the liquid on the basis of a compensated output from the neural network algorithm.

In another aspect, the present invention also provides software for assessing the concentration of at least one analyte ion in a liquid, the software including a series of instructions executable by a processor to perform the steps of: receiving a signal from each of a plurality of electrodes contacting the liquid, each electrode generating the signal in response to sensing a selected ion in the liquid; inputting the signal from each of the electrodes as input data to a neural network algorithm that has been trained to calculate ion interference between the selected ion and other ions in the liquid sensed at one of the electrodes and/or electrode interference between ones of the electrodes sensing a same selected ion based on a result of a comparison of training data indicative of a known ionic concentration applied to the neural network algorithm and the known ionic concentration; compensating for said ion interference and/or said electrode interference; assessing the concentration of the at least one analyte ion in the liquid on the basis of a compensated output from the neural network algorithm; and outputting an easement of the concentration of the at least one analyte ion in the liquid.

In an embodiment, the ion selective electrodes (ISEs) comprise an Electronic Tongue (ET), which is an artificial taste system created from response signals from an array of sensors. Normally, an ET system comprises three main components: 1) a sensor array, 2) a signal transmitting devices and 3) data analyzing methods. The sensor array generally includes a number of co-reactive electrodes.

The above neural network is an example of a pattern recognition algorithm or technique which, in this case, is used to improve prediction accuracy in, for example, the foodstuff industry and for environmental assessments. In one arrangement, the pattern recognition technique has been developed to improve the pattern recognition accuracy of Electronic Tongue (ET) systems. Using input data from an ion-selective electrode array, the above method is able to avoid interference from undesired ions to offer high prediction accuracy and simultaneously determine multiple free ions in water samples. Furthermore, the Electronic Tongue system can be used for online in situ assessment of water quality and can be employed as a real time nutrient monitoring system for analysis of irrigation water quality for agronomy and horticulture.

In an embodiment, pattern recognition includes mathematical and artificial intelligence algorithms. It will be appreciated by those persons skilled in the art that the mathematical algorithms are less complicated and assume linear data I/O relationships. In comparison, artificial intelligence algorithms, including Artificial Neural Network algorithms, are far more complicated but are also applicable to non-linear systems. Furthermore, pattern recognition methods can also be separated into supervised and unsupervised algorithms, depending on whether the target objects need pattern recognition models to be constructed.

In an embodiment, pattern recognition algorithms includes two stages; the first stage including a pre-processing stage to improve pattern recognition performance by minimising interference and noise by pre-processing data using data reduction methods, such as Principal Component Analysis (PCA), Partial Least Square (PLS) and Fourier Transform (FT). These pre-processing methods reduce the complexities of pattern recognition and increase prediction accuracy.

In an embodiment, all sensor arrays in an ET system contain a variety of different working and reference electrodes and either the differences in potential or current between reference and working electrodes are utilized as data for the pattern recognition techniques. The method, device and software are particularly suitable for assessing the concentration of an analyte ion in a liquid including a mixture of ions. As the neural network compensates for ion interference and/or electrode interference, the method, device and/or software allows one or more ions to be accurately assessed even in the presence of other ions. In some embodiments, the method, device and/or software may be used for in situ analysis of a liquid, which can alleviate the need to collect and send samples to a laboratory for analysis.

In an embodiment, the pre-processing stage includes processing the signal from the electrodes using a genetic Independent Component Analysis (ICA) (geneticICA) algorithm. As stated below, it was found that prediction accuracy of ion concentrations in a liquid improved, when compared against known concentrations of the ions, when the geneticICA algorithm was used with respect to the neural network. In particular, prediction accuracy improved when the algorithm was used with respect to the artificial neural network 'geneticICA_ANN'. Thus, concentrations of ions can be assessed with greater accuracy when a genetic algorithm is used to process the signal from the electrodes before it is processed by the neural network algorithm.

GENERAL DESCRIPTION

As mentioned above, the method of the present invention involves contacting a liquid with a plurality of electrodes. The electrodes may include one or more ion selective electrodes including, for example, polymer membrane electrodes, solid state electrodes, gas sensing electrodes, ion-exchange resin membranes, crystalline membrane electrodes, or glass membrane electrodes. In some embodiments, 2, 3, 4, 5, 6, 7, 8, 9, 10, 11, 12, or more ion selective electrodes may be used.

Ion selective electrodes generally function by converting the activity of a specific ion dissolved in a solution into an electrical potential which is detected. The electric potential may be detected by a voltmeter or a pH meter. Thus, the term "signal" as used herein in relation to the electrodes is intended to mean an electric potential produced by the electrode and/or a reading from a voltmeter, pH meter or other electrical potential detection device.

While ion selective electrodes may be "selective" for a particular ion (e.g. sodium, magnesium, calcium, potassium, ammonium, nitrate, phosphorus, chloride, or sulphur ions), it will be appreciated that ion selective electrodes may not be completely ion specific. Thus, the term "ion selective electrode", as used herein, is intended to mean an electrode that elicits a strong signal in the presence of a particular ion relative to the signal of another particular ion. For example, a potassium selective electrode is likely to generate a signal in the presence of calcium ions, although the signal would be expected to be lower than in the presence of potassium ions. The signal generated by the potassium selective electrode in response to the calcium ion is referred to herein as "ion interference". If the potassium selective electrode is used in a liquid containing calcium and potassium ions, the signal generated will be a compound signal (e.g. a potassium signal+a calcium interference signal).

Individual ion selective electrodes may also influence signals generated by other electrodes via the liquid in which they reside. This may be particularly evident when a single reference electrode is used. The potential differences between the ion selective electrodes and the reference electrode may be influenced by each other, since all the ion selective electrodes are measuring the same liquid at the same time and sharing the same reference electrode. For example, an activated potassium selective electrode may cause a calcium selective electrode to generate a signal independent of the presence of calcium ions in the liquid. The signal generated by the calcium selective electrode in response to the activated potassium selective electrode is referred to herein as "electrode interference". Accordingly, a signal generated by an electrode may be a compound signal including a selective ion signal, an electrode interference signal and/or an ion interference signal.

As described above, the present method includes obtaining a signal from each of the electrodes and providing the signal from each electrode as input data for a neural network. The input data may be for example a set of values, each value indicative of the electric potential of an electrode, or the input data may be a set of values obtained from pre-processing the signals. Each electrode may generate a compounded signal, which includes a selective ion signal, one or more ion interference signals and/or one or more electrode interference signals. The purpose of the neural network is to calculate and/or compensate for ion interference and/or electrode interference. In this regard, the present invention may allow for accurate measurement of one or more ions in a mixed ion solution.

In one arrangement, the sensor array of an Electronic Tongue (ET) system includes one reference electrode in conjunction with several working electrodes. Depending on the type of working electrode, either differences in potential (potentiometric) or current (voltammetric) between the reference and working electrodes can be assessed using pattern recognition. Thus, in this arrangement, there are two classes of sensors: firstly potentiometric sensors are used when differences in voltages are considered; and secondly voltammetric sensors are used when differences in currents are studied.

For potentiometric systems, the potential of a solution between working electrode and the reference electrode is related to the concentration of one or more analytes. In an embodiment, the working electrodes of potentiometric sensors include ion-selective electrodes (ISEs), solid-contact electrodes (SCE), coated wire electrodes (CWE), ion-sensitive field-effect transistors (ISFETs) and light addressable potentiometric sensors (LAPS) and can be made from different types of chemical sensors. Also, depending on the response reproducibility and non-selectivity factors, potentiometric working electrodes can be divided into specific electrodes, partially specific electrodes and non-specific electrodes. Compared to the variety of different working electrodes, in the embodiment, there are only two main types of reference electrodes used in potentiometric systems. These include Calomel electrodes and silver/silver chloride electrodes (Ag/AgCl).

Compared to other analytical techniques, ion-selective electrodes have the benefits of being relatively inexpensive, simple to use and exhibit a rapid response, which are essential for in situ monitoring of ions in environmental samples. ISEs may be made from a variety of materials, such as impregnated-PVC (Polyvinyl Chloride), glass and crystalline minerals. Depending on selectivity, the electrodes can be separated into ion-selective and cross-selective electrodes and interference is measured by selectivity coefficients.

It will be appreciated by those persons skilled in the art that the working electrodes utilized in voltammetry are much simpler than those used in potentiometric systems, and are usually composed of special metallic wires or discs. However, the electro-analytical systems for recording current values are far more complicated than those required for recording potential values, and a current-to-voltage converter is also necessary to provide signals suitable for analysis. In addition, instead of recording the signal simultaneously, a Solid State Relay (SSR) is normally introduced for logging the signals from each working electrode consecutively. Furthermore, in addition to the reference and working electrodes, an extra electrode, known as the counter electrode, is utilized for stabilizing the potential differences between working and reference electrodes.

The materials most commonly used for the construction of working electrodes are metallic, carbon paste or polypyrrole based. In an embodiment, metallic electrodes are made of noble metals (e.g. gold, platinum, rhodium, Iridium, silver) or non-noble metals (e.g. copper, tin, iron, aluminium, brass and stainless steel). Carbon paste and polypyrrole-based electrodes are special types of electrodes made from a mixture of conducting graphite powder and a pasting liquid. For the reference electrodes, both Ag/AgCl or Hg/Hg2SO4 reference electrodes and stainless steel electrodes are used. It will be appreciated, however, that reference electrodes are not required when the received values are sufficiently stable for pattern recognition analysis. Also, stainless steel and platinum electrodes are employed as the counter electrodes.

Various voltammetric waveforms are used to supply current information to the ET systems for different applications including: Pulse Voltammetry (PV), Cyclic Voltammetry (CV) and Square-Wave Voltammetry (SWV). Pulse Voltammetry has a low detection limit, which is appropriate for detecting trace elements like heavy metals. Square-Wave Voltammetry has a high sensitivity and is suitable when high prediction accuracy is required. Cyclic Voltammetry has a lower sensitivity, and is applicable to general studies.

As described, Electronic Tongue (ET) systems with various pattern recognition techniques are used for potential applications in the food industry and in environment monitoring. The applications of ET systems can be classified into either qualitative or quantitative analysis. Qualitative analysis involves separating observations into different clusters and predicting the probable class membership for new observations (which has been applied in the food and beverages industries). Qualitative analysis is principally concerned with discrimination, classification and identification of the observations from different classes. According to the unit responses from each individual sensor within the sensor array, ETs attempt to provide digital "fingerprints" for different "tastes" and specify the identity from the various solutions. In terms of quantitative analysis, ETs have been used to find specific ions or neutral species in both foodstuffs and environmental matrices.

For example, in qualitative analysis, the mathematical algorithms can be divided into supervised and unsupervised learning algorithms. Supervised algorithms are generally implemented by assigning or discriminating an unknown instance to the known groups of objects. For supervised algorithms, before analysing the observation data, it is necessary to build pattern recognition models with pairs of training data and targets. The supervised algorithms include K-Nearest Neighbours (KNN) and Discriminate Analysis (DA). The unsupervised algorithms include Cluster Analysis (CA), which is generally used for separating a group of unknown objects into different clusters without building a model.

For quantitative analysis, the mathematical algorithms use supervised regression methods. There are three widely employed regression methods: Multivariate Linear Regression (MLR), Principal Component Regression (PCR) and Partial Least Squares Regression (PLS). MLR is a powerful prediction method used to build equations or models that evaluate the concentration of observations, based on predictor variables. It is often assumed that the observation data set denoted as X, n×m matrix, where n is the number of observations and has m number of predictor variables per observation. In an ET system, for example, the matrix X is organized by n training solutions, and m is the variable values from each response sensor. The target data, is denoted as Y, n×k matrix, where n number of observation solutions with k number of concentrations. For building the models, the Multivariate Linear Regression estimates a m×k matrix of coefficients W, where $Y = W \cdot X$. Principal Component Regression (PCR) and Partial Least Square (PLS) Regression are similar to Multiple Linear Regression, except choosing the predictor variables. Instead of directly utilizing the observation data from the sensor array, PCs by PCA and LVs by PLS can be employed as predictor variables by PCR and PLS respectively. It will be appreciated by those persons skilled in the art that all the regression methods mentioned above are linear methods and may not suitable for more complicated non-linear discrimination, even if the regression methods can be implemented in a non-linear way using Non-linear Iterative algorithms. The iterative algorithms initialize the weight matrix with random numbers then iteratively adjust the weights by minimizing the square deviations between the predicted and target values. There are usually 4 types of non-linearities: (pow3(x), tan h(x), gauss(x), skew(x)) to be considered.

As described, before utilizing pattern recognition techniques, the data collected from sensor arrays undergoes, in one embodiment, some data pre-processing processes, such as auto scaling and normalization. With respect to the above arrangement, since all the electrodes measure observations together, the co-reactive responses from the electrodes may correlate to one another. These co-reactive responses afford redundant information to the ET system. Additionally, there are errors in the observation data generated during sample preparation or measurement which bring deviations into pattern recognition. Considering such complicated scenarios, pattern recognition techniques are often combined with data pre-processing techniques to remove redundant information in a two-stage pattern recognition technique.

In an embodiment, common data pre-processing techniques include Principal Components Analysis (PCA), Partial Least Square (PLS) and Fast Fourier Transform (FFT).

In an embodiment, pattern recognition methods can be generally categorized into either mathematical or artificial Neural Network algorithms. The mathematical algorithms are mainly applied to the analysis of data based on linear input/output data relationships and the Artificial Neural Networks (ANNs) algorithms can solve non-linear data relationships in real complex situations for both qualitative and quantitative analysis.

A neural network is a mathematical or computational model that is trained to predict a set of one or more outputs resulting from a given set of one or more inputs. Neural networks may be used for classifying patterns or modelling complex relationships between inputs and outputs. The architecture of a neural network includes a number of interconnected processing elements (neurons). Each neuron receives one or more inputs and computes an output which is propagated to other neurons in the network. The network may be arranged in layers including an input layer, a layer of hidden neurons and a layer of output neurons. Generally, the inputs into the neurons are weighted and summed, and the output of the neuron is controlled by a transfer function, which outputs a value depending on the summed weighted inputs. For example, the transfer function may be a threshold function that outputs one of two values, depending on whether the summed weighted inputs are below or above a threshold. Alternatively, the transfer function may simply output the input unchanged, or may output a value on a given scale.

A neural network may be trained by feeding it inputs having known outputs. The error between the outputs predicted by the neural network and the known outputs is determined and used to adjust the weights according to a modification rule. This process continues iteratively using a number of training examples until the error between the predicted outputs and the known outputs reaches an acceptable level.

In the present invention, the neural network may produce output data indicative of the concentration of an analyte ion in a liquid. The output data may be a set of values, each value indicating the concentration of a different analyte ion e.g. in mol/L or mg/L. Post-processing of the output data may be required to assess the concentration of each analyte ion. For example, the output data may need to be scaled. Alternatively, the neural network may produce output data indicative of the errors caused by ion interference and/or electrode interference. These errors may then be subtracted (or otherwise compensated for) from the actual signal from the relevant electrodes to assess the concentration of the analyte ion in the liquid. In this case, the neural network would be trained to predict errors in the signals, rather than to predict the ion concentration.

In an embodiment, the neural network includes Artificial Neural Networks (ANNs), which are applied as a pattern recognition method in ET systems for both qualitative and quantitative analysis. An Artificial Neural Network (ANN) is a nonparametric modeling algorithm which emulates biological neurons in order to understand the relationship between the input patterns and their targets. The technique is particularly appropriate for both qualitative and quantitative analysis in pattern recognitions, where complicated, noisy and imprecise input patterns occur. For example, for qualitative analysis, two ANN algorithms include Learning Vector Quantization and Self-organizing Map. Normally, ANN contains one input layer, one output layer and one or more hidden layers and there are a series of neurons with relative weight vectors in each layer. The complex relationships between the vector of input patterns X and their target vector Y are approximated by adjusting the matrix of weight vectors W and the neurons number in the hidden layers.

It will be appreciated by those persons skilled in the art that in order to obtain a Neural Network with the proper modeling ability, the topology of the Neural Network with the relative weights must be correctly configured. The size of the Neural Network is determined by the number of layers and neurons within that network. The number of input neurons is determined by the input pattern representation. The number of output neurons is determined by the target value required and the number of layers and neurons for a hidden layer is related to the system complexity.

After being configured, Artificial Neural Networks are initialized by weighting neurons with random numbers. At this stage, the ANN knows nothing about the relationships between the vector of input pattern X and their target vector Y. For training the Neural Networks, many different learning algorithms are available and these include: Bayesian regularization back propagation training algorithm, Gradient descent back propagation training algorithm, Levenberg-Marquardt training algorithm and Resilient back propagation training algorithm. During the training period, ANN adjusts the output values to match the targets. The average least squares error is typically used as a criterion to evaluate the ANN's prediction performance. If the output criteria are satisfied then all the neural weights are reinforced. Otherwise, the weight vectors would be adjusted iteratively until the output is satisfied.

The method may further include processing the signal from one or more of the electrodes with an algorithm and providing the processed signal as input data for the neural network. Pre-processing the signal may reduce errors and improve the prediction accuracy of the neural network by providing input data that is easier for the neural network to process.

Pre-processing techniques are used to develop new data sets with less artificial variables in order to increase accuracy of analysis. These new variables make it possible to represent all the variances in the original observation data. One of the most important functions of data pre-processing is to reduce the complexity of the observed data. Since each artificial variable contains different amounts of variance in the observation data, ranking these artificial variables by how much variance information they contain, allows data reduction to be implemented by removing the new variables with no or low variance information.

One example of a pre-processing technique is Principal Component Analysis (PCA), which is an orthogonal linear transformation pre-processing method which linearly projects the multi-dimensional observation data into a new coordinate system. The variables in the new coordinates are orthogonal uncorrelated, and contain a maximum amount of variance information. PCA is normally implemented by the Singular Value Decomposition (SVD) algorithm, and the new data components, containing variance information can be represented by pairs of eigenvalues and eigenvectors. Eigenvectors indicate the directions of the new data coordinate system, whereas eigenvalues indicate the amount of variance from observation data each PC contains. The higher the eigenvalues the more variance information the relative component contains. Ranking the components by their eigenvalues from high to low, allows the highest components called the Principal Components (PCs) to be identified and data dimensions can be reduced by eliminating eigenvectors with the lowest eigenvalues. In most applications of PCA, the first two or three PCs extracted normally captured most of the variability. By utilizing PCA score plots, where the first two (three) PCs are represented as x-, y- and z-axis significant information for qualitative classification is theoretically described. Soft Independent Modeling of Class Analogy (SIMCA) is a supervised classification method which constructs classification models using PCA. New observations are assigned to the model class by being projected into the PCs score plot. PCA is normally applied as a data pre-processing method to reduce the number of data dimensions prior to further analysis.

In another example of a pre-processing technique, Partial Least Square (PLS) is a computational mathematical algorithm used for both qualitative and quantitative analysis. The factor extraction function of PLS can also be adopted for data reduction. Similar to PCA, the factor extraction function of PLS is also based on linear transformation of a high dimensional original observation data set into a small number of orthogonal factors, where PLS creates new variances, denoted by Latent Variables (LVs), where the latent vectors contain information on the correlations between the observed and target data. To calculate the LVs, both observed data and target data are employed. Data reduction is conducted by retaining LVs that capture the majority of the relationship information. The main difference between PCA and PLS is that PCA preserves variance rather than the correlations. As with PCA, PLS score plots can be used to display LVs in a new coordinate system, allowing sufficient information to be presented for classification and determination. PLS can be implemented by either the NIPALS (Non-linear Iterative Partial Least Squares) algorithm or the SIMPLE (Semi-Implicit Method for Pressure Linked Equations) algorithm.

In another example of a pre-processing technique, Fourier Transform (FT) analysis is based on the properties of trigonometric functions. In Fourier Transform analysis, the signals (wavelets) from their original domain, typically the time domain, are able to be transformed into combinations of sinusoids with different frequencies and amplitudes in the frequency domain. With this trigonometric transform, the variances from the signal are represented by amplitudes and frequencies and the amplitudes are recognized as Fourier coefficients. Data pre-processing is implemented by retaining the frequencies with higher Fourier coefficients (amplitudes). Discrete Fourier Transform (DFT), especially Fast Fourier Transform (FFT) is widely utilized to analyze signals from sensor arrays. Fast Fourier Transform (FFT) uses the periodicity functions to compute an N-point Discrete Fourier Transform with approximately N/2 operations.

The procedure for FFT transform from the time domain signal to the frequency spectrum is based on three overarching steps: 1) Time domain decomposition, using the so called Interlaced Decomposition algorithm, where the N point time domain signal is separated into N number of one point time domain signals; 2) Finding the relative frequency spectrum for each of the decomposed time domain signals; and 3) Frequency Domain Synthesis, where the N frequency spectrum is synthesized into a single frequency spectrum by using the so-called butterfly calculation algorithm.

In some embodiments, the signal from one or more of the electrodes is processed by Independent Component Analysis (ICA). In other examples, the signal may be processed using methods such as Nonlinear Principal Component Regression (PCR) and Nonlinear Partial Least Squares (PLS) Regression.

ICA is traditionally the main method of Blind Signal Separation (BSS). By using ICA, signals are separated into underlying independent components. These independent components maximize the so-called non-gaussianity properties of the signal. The ICA paradigm is as follows: The central limit theorem purports that most linear combinations of signals are more Gaussian than any of the independent signals. In ICA, it is assumed that the components of the data matrix X (representing the signal) are mixtures of independent components matrix S. There is a separating vector B, such that S=BX. The objective of Independent Component Analysis is to iteratively calculate the separating matrix B that minimizes the gaussianity of BX. To implement ICA, firstly the data matrix X (representing the signal) is whitened following three steps:

i. Centering by removal of means;
ii. Principal Component Analysis (PCA) to remove the correlations between data, simultaneously finding directions with maximal variance; and
iii. Data normalization, which ensures that the square root of the normalized data equals one.

Mathematically we denote Z to be the whitened data matrix, where Z=VX, V is the data whitened matrix. The independent component matrix $S=W^TZ$, where W is the separating matrix for the whitened signal. Whitening the data matrix X causes the separating matrix W to become orthogonal. Every separating vector win W is mutually orthogonal.

The pre-processing of the signal using ICA may be implemented using a geneticICA or fastICA algorithm.

FastICA is a fixed-point algorithm, based on a gradient function. For the whitened data Z, when the number of independent components is determined, fastICA will start initializing and orthogonalizing the separating matrix W with unit norm random values, then it simply iteratively replaces every separating vector $w_i$ in W with a new separating vector determined using the gradient function (1), which is given by $$E\{zf(w_i^T z)\} - E\{f'(w_i^T z)\} w_i \qquad (1)$$

and orthogonalizes the matrix symmetrically until convergence is achieved.

In the fastICA fixed-point algorithm, there are usually 4 types of nonlinearities: pow3 ($f(x)=x^3$), tan h($f(x)$=tan h($a1*x$)), gauss ($f(x)=x*\exp(-a2*x^2/2)$) and skew ($f(x)=x^2$), related to their Independent Components (ICs) extraction ability. There is no linear correlation between the resultant ICs, since the ICs are mutually orthogonal. The ICs are also considered to be latent variables, that are not able to be directly observed, but may be used as feature information for the prediction of neural networks.

In some embodiments, the algorithm for processing the signal may include a geneticICA algorithm. GeneticICA implements fastICA by using a genetic algorithm. The difference between geneticICA and normal fastICA is: fastICA is based on a gradient algorithm starting from one random matrix, as a single point in the Probability Density Function (PDF) of the model; geneticICA is based on a genetic algorithm starting from a number of random matrices, as multiple points in the PDF of the model. FastICA searches for the optimum result using a single point in the PDF of the model. If the model has a high data dimension and is non-linear, then the fastICA algorithm may face the local maxima problem. If the fastICA algorithm identifies a local maxima in a multi-dimensional parameter space, it may search a local smaller parameter area rather than the whole parameter space. GeneticICA searches for the optimum result using multiple points in the PDF of the model. The use of multiple starting points located efficiently in the parameter space avoids the local maxima problem. Similarly to fastICA, data used for GeneticICA analysis may be the zero mean and whitened data matrix Z.

The Independent Components (ICs) gained from fastICA or GeneticICA, may then be sent to a Neural Network that has been trained to produce output data indicative of the concentration of the analyte ion in a liquid. Prediction results from the neural network can be used for simultaneous determination of multi-free ions.

In some embodiments, the neural network may include a Back-propagation Feed-forward Neural Network (BPNN). A feed forward neural network allows signals to travel one way, from input to output. There are no feedback loops feeding outputs from one layer of the neural network into inputs of neurons in the same or previous layers. Back-propagation refers to a method used in training the neural network, of calculating how the error between the desired output and actual output changes as each weight is modified slightly. The rate at which the error changes as the activity level of a neuron changes is calculated moving from layer to layer in a direction opposite to the way the neural network normally propagates. So the error is propagated backwards through the neural network.

The method of the present invention may further include training the neural network. Training the neural network may include: contacting a training sample of known ionic concentration with the plurality of electrodes; obtaining a signal from each of the electrodes; providing the signal from each of the electrodes as training data for the neural network; comparing output data from the neural network with the known ionic concentration of the training sample; and adjusting weights in the neural network based on a result of the comparison.

Training the neural network may include using an orthogonal experimental design to reduce the number of training samples required to adequately train the neural network. Orthogonal experimental design is a method of choosing data inputs for running experiments where there are a variables with b different values. The data inputs are chosen so that only a set number of experiments need to be run to obtain adequate output for analysis. The data inputs are predefined combinations of the b different values. When applied to neural network training, orthogonal experimental design provides a spread of input values that are sufficient to adequately train the neural network.

As set out above, the method may be used to assess the concentration of an analyte ion in a liquid. The analyte ion may be in the form of, for example, an ion including an element or compound including sodium, copper, iron, lead, cadmium, magnesium, calcium, potassium, ammonium, nitrate, phosphate, phosphorus, chloride, sulphate, or sulfur. For example, the ion may be $Na^+$, $Mg^{2+}$, $Ca^{2+}$, $K^+$, or $NH^{4+}$, optionally associated with a non-metallic anion, or the ion may be, $NO^{3-}$, $PO_4^{3-}$, $Cl^-$, or $SO_4^{2-}$, optionally associated with a cation.

The method may be used to simultaneously assess the concentration of a plurality of analyte ions in the liquid. For example, the method may be used to simultaneously assess the concentration of two or more of the following ions in a liquid: sodium, copper, iron, lead, cadmium, magnesium, calcium, potassium, ammonium, nitrate, phosphate, phosphorus, chloride, sulphate, or sulphur.

Analyte ions of varying concentrations may be detected. For example, in some embodiments, the concentration of the analyte ion(s) may be between $10^{-1}$ M and $10^{-5}$ M. Concentrations of analyte ions in a liquid above or below this concentration range may be assessed by diluting or concentrating the liquid, respectively. Methods for diluting or concentrating the liquid include those methods generally known in the art including adding a solvent (e.g. water) or reducing the amount of solvent in the liquid (e.g. by vaporising a portion of the solvent from the liquid). Particularly suitable concentration ranges for sodium and/or chloride are between $10^{-1}$ M and $10^{-4}$ M and calcium, potassium, ammonium and/or nitrate are between $10^{-2}$ M and $10^{-5}$ M.

The method may include filtering the liquid prior to contacting the liquid with the electrodes. Filtering the liquid can remove unwanted components from the liquid which may otherwise affect the operation or maintenance of the electrodes. Examples of unwanted components may include particulate matter (e.g. sand, dirt, etc.), organic matter (e.g. leaves, debris, etc), microorganisms (e.g. bacteria, protozoa, microbial cysts, etc.). In some embodiments, filtering the liquid may include passing the liquid through one or more filters. As can be appreciated, the selection of the one or more filters will depend on the nature of the unwanted components in the liquid.

The method according to embodiments of the present invention may be used for in-situ water quality assessment. For example, a water sample may be taken directly from a water source (e.g. waste water, reservoir or water system) and contacted with the plurality of electrodes without having to send the sample to a laboratory. In this regard, the water quality may be assessed rapidly.

As mentioned above, the present invention also provides a device for assessing the concentration of an analyte ion in a liquid. The electrodes of the device are preferably ion selective electrodes that at least primarily convert the activity of a specific ion dissolved in a liquid into an electrical potential. For example, a $Na^+$ selective electrode will primarily generate an electrical potential for $Na^+$. However, it will be appreciated that the $Na^+$ selective electrode may also generate electrical potentials for other ions that react with the $Na^+$ selective electrode albeit to a lesser degree than $Na^+$ (i.e. other ions may cause "ion interference", as described above). In some embodiments, the electrodes may include one or more ion selective electrodes selected from the following group: sodium, copper, iron, lead, cadmium, magnesium, calcium, potassium, ammonium, nitrate, phosphate, phosphorus, chloride, sulphate, or sulphur selective electrodes. A pH electrode may also be used.

Accordingly, in some embodiments, one or more of the electrodes may generate a signal in response to one or more analyte ions including an element or compound selected from the following: sodium, copper, iron, lead, cadmium, magnesium, calcium, potassium, ammonium, nitrate, phosphate, phosphorus, chloride, sulphate, or sulfur.

The plurality of electrodes may be exposed to the outside of the device, allowing them to be dipped into a liquid to be assessed (e.g. the electrodes may be dipped into a pool of water or a water sample collected in a container). Alternatively, the device may have a liquid sampling unit which includes a chamber housing the plurality of ion selective electrodes and an inlet for introducing liquid into the chamber. The inlet may be connected to a sampling tube, or the like, which may be positioned such that the end of the sampling tube is submerged in the liquid to be tested.

The provision of a liquid sampling unit having a chamber housing the electrodes can protect the electrodes, control the volume of liquid to be analysed and/or insulate the water sample from external influences (e.g. external electrical influences).

The device may be a portable unit allowing it to be moved between testing sites or may be a fixed device (e.g. the device may be retained at one testing site). The latter may be beneficial for automated testing of particular sites that require regular monitoring.

The liquid sampling unit may further include one or more filters for filtering liquid being introduced into the chamber. The filters may be used to remove unwanted components from the liquid which may otherwise affect the operation and/or maintenance of the device. The selection of the filter will depend on the composition of the liquid (e.g. what unwanted components may be present). Examples of unwanted components may include particulate matter (e.g. sand, dirt, etc.), organic matter (e.g. leaves, etc), microorganisms (e.g. bacteria, protozoa, microbial cysts, etc.)

In some embodiments, the one or more filters may be provided on or near the inlet for introducing liquid into the chamber or on or near a sampling tube providing fluid communication between the liquid source and the inlet. Examples of suitable filters may include mesh sieves, fabric filters, micropore filters, nucleopore filters, in-line filters, and the like. In some embodiments, the filter may include a cellulose acetate, nitrocellulose, PTFE (Teflon) laminated, PTFE (Teflon) unlaminated, polycarbonate, glass fiber, silver metal, ceramic, polyester, polyethersulfone, polypropylene, or nylon membrane and/or prefilter. Different pore sizes (e.g. 0.01-30 microns) may be selected to suit the filtration of particular unwanted materials.

While any means of introducing the liquid into the liquid sampling unit chamber are contemplated by the present invention, in some embodiments, the device may include a pump for introducing liquid into the liquid sampling unit, moving liquid through the liquid sampling unit and/or expelling liquid from the liquid sampling unit. The pump may be a hand operated pump or automated pump including, for example, an impellor pump, a peristaltic pump, a submersible sump pump, a centrifugal pump, a metering pump, a gear pump, a helical pump, a magnetic drive pump, or the like. In some embodiments, the device may include multiple pumps.

The device may further include a control system that controls the operation of one or more pumps, the electrodes, signal transmitters and/or the data processing unit. In this regard, one or more steps may run automatically and/or with minimal user input. In some embodiments, a user may simply place the device such that the inlet is in fluid communication with a liquid source and press an activation switch on the device. The control system may activate a pump, which pumps liquid from the liquid source into the chamber housing the plurality of electrodes. The housing may include a fluid level switch which is activated when a predetermined volume of liquid is introduced into the chamber (e.g. when the electrodes are adequately submerged in the liquid in the chamber). Activation of the fluid level switch may deactivate the pump to prevent overfilling of the chamber and/or may activate the plurality of electrodes. Signals generated by the electrodes are then obtained and processed to provide data for input into the neural network to assess the concentration of the analyte ion in the liquid. Once data has been collected, the control system may activate a second pump for expelling the liquid from the chamber through an outlet or may open an outlet through which the liquid may be expelled by gravity.

The control system may control a periodic sampling of a liquid and/or periodic assessment of the concentration of an analyte ion in a liquid. For example, the control system may include a timer that initiates liquid sampling (e.g. pump activation) at predetermined intervals of time. In some embodiments, the control system may include a timer that initiates assessment of a liquid in the chamber at predetermined intervals of time (e.g. activation of electrodes). This may be particularly be useful if the chamber is submerged in the liquid and closable inlets and outlets allow the liquid to flow through the chamber when the electrodes are inactive.

The device may further include a data storage device or a data transmitter. The data storage device may be any means of storing information, such as a memory of the data processing unit, a solid state storage device or a magnetic device. It may be a computer readable media such as a CD, DVD, USB flash drive or an external hard drive. The data transmitter may be a wireless network transmitter. Suitable communications ports may use an IEEE802.11 based wireless interface, a general packet radio service (GPRS) compatible interface, a wireless application protocol (WAP) compatible interface, a Bluetooth interface, an optical interface (such as an IrDA interface), a ZigBee interface, a 433M interface, a universal serial bus (USB) interface or the like, or an radio frequency identification (RFID) induction based communication interface.

The device may have a battery as a power source. In this regard, the device may be portable and/or used in remote or relatively inaccessible areas. The battery is preferably rechargeable and/or replaceable. Alternatively, the device may be connectable to a power supply (e.g. mains power, a generator, or a solar power device).

The signal transmitters that operate between the electrodes and the data processing unit may include one or more of: a signal amplifier; a low pass signal filter; a signal multiplexer; and an analog/digital converter. It will be appreciated that other appropriate electronic components may be used. The signal transmitters convert the raw signals from the electrodes into input data for the neural network, which the signal transmitters then transmit to the data processing unit.

As described above, the neural network may be a Backpropagation Feed-forward Neural Network (BPNN).

The data processing unit may further include software for processing data before input into the Neural Network. The software may include a geneticICA or fastICA algorithm for processing data before input into the Neural Network. As outlined above, the use of ICA to pre-process the data may reduce errors and improve the prediction accuracy of the neural network.

The present invention is further described by the following non-limiting examples:

BRIEF DESCRIPTION OF THE FIGURES

FIG. 12 shows a graph of the prediction errors for an ion selective electrode array according to an embodiment of the present invention.

FIG. 13 is a table showing the results of an assessment of ion concentrations in water samples taken from the field according to an embodiment of the present invention.

FIG. 16 shows a table of selectivity coefficients (K) for seven ISE's used with respect to the water sampling unit of FIG. 14.

FIG. 19 shows a table comparing prediction results against actual results for three water samples according to an embodiment of the present invention.

FIG. 20 shows another table of selectivity coefficients (K) for seven ISE's used with respect to the water sampling unit of FIG. 14.

METHOD OVERVIEW

Figure 1:
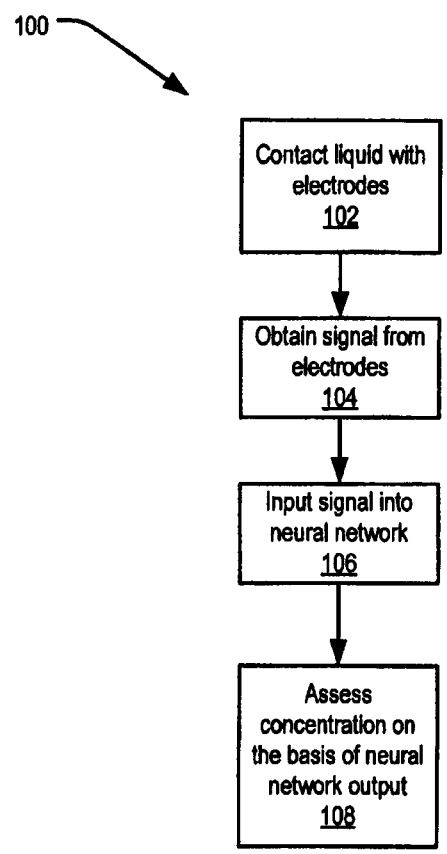
FIG. 1 is a flow chart of a method for assessing the concentration of an analyte ion in a liquid, according to an embodiment of the invention.

Referring to FIG. 1, embodiments of the present invention provide a method 100 for assessing the concentration of an analyte ion in a liquid, the method including: contacting the liquid with a plurality of electrodes each of which generate a signal in response to one or more ions in solution at step 102; obtaining a signal from each of the electrodes at step 104; providing the signal from each of the electrodes as input data for a neural network that has been trained to compensate for ion interference and/or electrode interference at step 106; and at step 108, assessing the concentration of the analyte ion in the liquid on the basis of an output from the neural network. In one embodiment, the method 100 is for assessing the concentration of more than one analyte ion in a liquid and each of the electrodes are configured to generate a signal in response to sensing a selected ion in the liquid. These signals are received and processed using a neural network algorithm residing on a processor that has been trained to calculate ion interference between the selected ion and other ions in the liquid sensed at one of the electrodes and/or electrode interference between ones of the electrodes sensing a same selected ion based on a result of a comparison of training data indicative of a known ionic concentration applied to the neural network algorithm and the known ionic concentration. The neural network then compensates for ion interference and/or electrode interference and is then used to assess the concentration of the analyte ions in the liquid.

Figure 30:
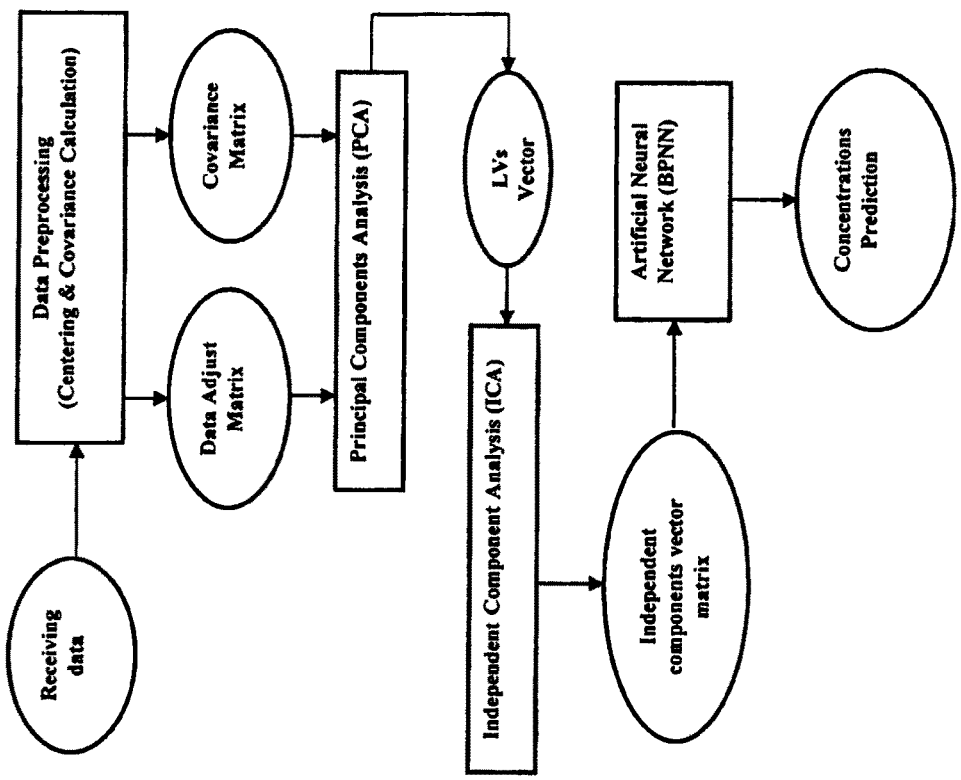
FIG. 30 is a flow chart of a method of assessing concentration of analyte ions in a liquid according to an embodiment of the invention.

Referring to FIG. 30, a further embodiment of the present invention is shown. In the embodiment, the method of assessing concentration of analyte ions in a liquid includes the steps of pre-processing the signals received from the electrodes before being inputted to the neural network algorithm as described. Here it can be seen that data pre-processing includes centering and covariance calculations, Principal Components Analysis (PCA), and Independent Components Analysis (ICA) before being fed into an Artificial Neural Network (e.g. BPNN) as described for assessing concentrations of ions in the liquid.

The following examples further define aspects of methods, devices and software according to embodiments of the present invention.

EXAMPLE 1

Simulation Data Setup

In this experiment, the data has eight dimensions (D1, D2, D3, D4, D5, D6, D7, D8). Accordingly, the ISE Array has eight response values for each solution. Each value was made up from a different combination of eight elements (E1, E2, E3, E4, E5, E6, E7, E8). Bearing in mind the range of Ion Selective Electrodes' measurement (Van London pHoniex Co.), the range of simulation data in each dimension was setup from the level of 0.1 ppm ($10^{-6}$ M level) to the level of ten thousand ppm ($10^{-1}$ M level). The normal response formats of electrodes to their desired ions are shown as below:

$$D_1(mV)=20*E_1+150 \quad (3)$$

$$D_2(mV)=-27*E_2+200 \quad (4)$$

$$D_3(mV)=15*E_3-300 \quad (5)$$

$$D_4(mV)=-30*E_4+320 \quad (6)$$

$$D_5(mV)=25*E_5+100 \quad (7)$$

$$D_6(mV)=15*E_6-250 \quad (8)$$

$$D_7(mV)=-30*E_7+320 \quad (9)$$

$$D_8(mV)=25*E_8-150 \quad (10)$$

For measuring errors brought by the interferences, The following Interfering Error formula was employed:

Interfering Error=$E(|\text{Error}|)$ between $V_{with\ interference}$ and $V_{without\ interference}$ (12)

Figure 2:
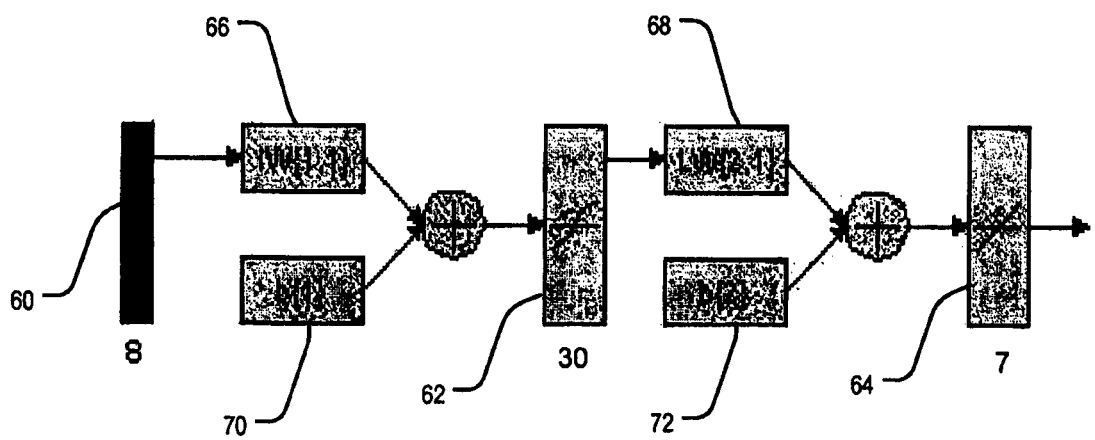
FIG. 2 is a block diagram showing a general structure of a Neural Network used according to an embodiment of the present invention.

FIG. 2 shows the architecture of an Artificial Neural Network (ANN) model set to 8*30*7 BPNN. There are 8 neurons in the input layer 60, 30 neurons in the hidden layer 62 and 7 neurons in the output layer 64. The tangent sigmoid transfer function (Tansig) was used as the transfer function for the hidden layer 62. The linear purelin transfer function was employed as the output function for the output layer 64. The weights 66, 68 and biases 70, 72 of the ANN were initialized randomly before applying the Bayesian regularization backpropagation <TRAINBR>. The training function was set to 100 epochs. The data set was separated into a training set and a testing set. Both the training data set and the testing data set were made up of 50 data vectors with random combinations of data values. The prediction system was trained with the training data set and validated with a validating data set. The robustness and appropriateness of structured approach was assessed by the Mean of Relative Error of the testing data set, given in (11) as follow, $$E(|\text{Error}|) = \frac{1}{n_{Test}} \sum_{i=1}^{N_{Test}} \left| \frac{C_i - C'_i}{C_i} \right| \quad (11)$$

In equation (11), $C'_i$ indicates the $i_{th}$ predicted value, the $C_i$ indicates the $i_{th}$ true concentration and $n_{Test}$ denotes the number of the test data subset.

As shown in table.1, there are four interference levels. The first level was High interference (D1, D2). In this level, it was assumed that there were more than 4 elements which interfere with the electrode. The Second level was Medium interference (D3, D4), in which it was assumed that there were 3 or 4 interfering elements. The Third level was Few interference (D5, D6), in which it was assumed that there was 1 or 2 interfering elements. The Fourth level was no interference (D7, D8).

TABLE 1

Simulation of Interferences

| Data Dimension | Interfering Levels | Mainly detection | Interferences |
|---|---|---|---|
| D1 | High | E1 | E2, E3, E4, E5, E6, E7 |
| D2 | High | E2 | E1, E3, E4, E5, E6, E7 |
| D3 | Medium | E3 | E4, E5, E6, E7 |
| D4 | Medium | E4 | E6, E7, E1 |
| D5 | Few | E5 | E3, E6 |
| D6 | Few | E6 | E2 |
| D7 | None | E7 | None |
| D8 | None | E8 | None |

EXAMPLE 2

Pure Linear Analysis

In this experiment, the pure linear interferences were tested. In this pure linear interfering situation, there was no fluctuation added into the data in any dimension. The linear functions were as follows:

$$D1=20*E1-5E2+3E3-3E4+2E5-2E6+E7+150(mV); \quad (14)$$

$$D2=-27*E2-5E1+5E3-5E4+3E5-2E6+E7+200(mV); \quad (15)$$

$$D3=15*E3-3E4+3E5-2E6+E7-300(mV); \quad (16)$$

$$D4=-30*E4-5E6+2E7+3E1+320(mV); \quad (17)$$

$$D5=25*E5+3E3-3E6+100(mV); \quad (18)$$

$$D6=15*E6-4E2-250(mV); \quad (19)$$

$$D7=-30*E7+280(mV); \quad (20)$$

$$D8=*E8-200(mV); \quad (21)$$

The data analysis result is shown in table.2. Interference from other data could increase the relative error of the system to 0.2. The average interfering error is around 0.12, which means that an error of more than ten percent was brought into the system. To demonstrate how geneticICA preprocessing could improve the prediction ability of neural network, the prediction results were compared with a fastICA supported neural network. The results were also compared with results obtained from a neural network without any data pre-processing methods. After the simulation, it was found that both geneticICA and fastICA could improve the prediction accuracy of the neural network. The prediction results from the fastICA supported neural network resulted in errors of the order $10^{-3}$ (specifically $2.4e^{-3}$), while the geneticICA supported neural network resulted in errors of the order $10^{-4}$ (specifically $1.79e^{-4}$). As such, it was evident that geneticICA supported neural networks have greater accuracy than fastICA supported neural networks. Nevertheless, fastICA supported neural networks were more accurate than neural networks that were not supported by pre-processing of the data. Specifically, the prediction precision of neural networks unsupported by pre-processing of data was 0.025.

From Table 3, it is evident that fluctuations can weaken the prediction ability of Neural Networks. As the Fluctuation Error increased, the prediction capability of the Neural Network decreased. In this simulation, to keep the prediction error below 0.10 of E(||Error||), the fluctuation should be controlled to under 5 (mV) of Fluctuation Error. Both fastICA and geneticICA were still able to extract independent components from their linear relationship. However, both ICA methods were unable to reduce the random fluctuation since it was difficult to find a relationship. With the high fluctuations, the geneticICA supported neural network had almost the same prediction results as the fastICA supported neural network. In practice, the noise from the system and measuring mistakes are ineludible. Accordingly, minimising the noise when sampling data is very important.

TABLE 3

Prediction Results of Various Fluctuations

| | | Prediction result E(RSD) | | |
|---|---|---|---|---|
| Noise | Fluctuation Error | geneticICA_NN | fastICA_NN | Neural Network |
| None | 0 | 1.79e-4 | 2.4e-3 | 0.025 |
| (rand (0:1) − 0.5) * 5 | 1.4 | 0.018 | 0.0182 | 0.033 |
| (rand (0:1) − 0.5) * 10 | 2.61 | 0.036 | 0.035 | 0.057 |
| (rand (0:1) − 0.5) * 20 | 5.28 | 0.077 | 0.075 | 0.081 |
| (rand (0:1) − 0.5) * 50 | 11.77 | 0.18 | 0.18 | 0.20 |
| (rand (0:1) − 0.5) * 80 | 19.96 | 0.29 | 0.29 | 0.32 |
| (rand (0:1) − 0.5) * 100 | 23.69 | 0.36 | 0.365 | 0.37 | geneticICA_NN: geneticICA supported neural network
fastICA_NN: fastICA supported neural network
Neural Network: neural network without data pre-processing methods

TABLE 2

Interfering Analysis

| Data Dimension | Mainly detection | Interference | Interfering Error |
|---|---|---|---|
| D1 | E1 | E2, E3, E4, E5, E6, E7 | 0.20 |
| D2 | E2 | E1, E3, E4, E5, E6, E7 | 0.048 |
| D3 | E3 | E4, E5, E6, E7 | 0.018 |
| D4 | E4 | E6, E7, E1 | 0.017 |
| D5 | E5 | E3, E6 | 0.57 |
| D6 | E6 | E2 | 0.10 |
| D7 | E7 | None | 0 |
| D8 | E8 | None | 0 |

The average of Interfering Rate (IR) = 0.12

EXAMPLE 3

Fluctuation Analysis

Based on the previous experiment, various fluctuations were added into each dimension of testing data. These fluctuations simulated errors resulting from system noise and measuring mistakes. Four different degrees of fluctuations were investigated and the prediction results are shown in Table 3. The influence of the fluctuations was measured by determining the Fluctuation Error (FE), which is the average errors for data by applying the following formula:

$$\text{Fluctuation Errors} = E(\|V_{with\ fluctuation} - V_{without\ fluctuation}\|) \quad (22)$$

EXAMPLE 4

Non Linear Analysis

In this experiment, the nonlinear interferences with a different degree of nonlinearity (K from 2 to 5, and K=10) were tested. No fluctuation was added. The nonlinear functions were as follows:

$$D1 = 20*E1 - (E2\cdot\hat{\ }K) + (E3\cdot\hat{\ }(K-1)) - (E4\cdot\hat{\ }K) + (E5\cdot\hat{\ }(K-1)) - (E6\cdot\hat{\ }K) + (E7\cdot\hat{\ }(K-1)) + 150; \quad (23)$$

$$D2 = -27*E2 - (E1\cdot\hat{\ }K) + (E3\cdot\hat{\ }(K-1)) - (E4\cdot\hat{\ }K) + (E5\cdot\hat{\ }(K-1)) - (E6\cdot\hat{\ }K) + (E7\cdot\hat{\ }(K-1)) + 200; \quad (24)$$

$$D3 = 15*E3 - (E4\cdot\hat{\ }K) + (E5\cdot\hat{\ }(K-1)) - (E6\cdot\hat{\ }K) + (E7\cdot\hat{\ }(K-1)) - 300; \quad (25)$$

$$D4 = -30*E4 - (E6\cdot\hat{\ }K) + (E7\cdot\hat{\ }(K-1)) + (E1\cdot\hat{\ }K) + 320; \quad (26)$$

$$D5 = 25*E5 + (E3\cdot\hat{\ }K) - (E6\cdot\hat{\ }(K-1)) + 100; \quad (27)$$

$$D6 = 15*E6 - (E2\cdot\hat{\ }K) - 250; \quad (28)$$

$$D7 = -30*E7 + 280; \quad (29)$$

$$D8 = *E8 - 200; \quad (30)$$

Following the increase of the nonlinearity degree, which is shown in Table 4, geneticICA demonstrated the strongest robustness for providing independent components to the Neural Network for further prediction. Even as the nonlinear interference degree was increased to 4, the neural network supported by geneticICA was still capable of predicting the results with errors of the order of $10^{-4}$ level. In comparison, the degree of interfering rate (IR) impaired the independent component extraction for the fastICA supported neural network. The fastICA could not converge when the nonlinearity degree was up to 4.

With a higher nonlinearity degree of interference, the number of epochs for training neural network has to be increased. In the scenario of a high input space dimension and nonlinearity, geneticICA was capable of extracting Independent Components for neural network prediction with higher accuracy and robustness than fastICA.

TABLE 4 prediction results comparing various nonlinear interfering degrees

| Non-linearity Degree (K) | Training epochs | Interfering Rate (IR) | Prediction result E(RSD) | | |
|---|---|---|---|---|---|
| | | | fastICA_NN | geneticICA_NN | NN |
| 1 | 150 | 0.12 | 2.4e−3 | 1.79e−4 | 0.025 |
| 2 | 500 | 0.42 | 3.4e−3 | 5.7e−4 | 0.18 |
| 3 | 500 | 1.98 | 0.17 | 7.3845e−4 | 0.27 |
| 4 | 500 | 9.32 | No convergence | 6.01e−4 | 0.20 | geneticICA_NN: geneticICA supported neural network
fastICA_NN: fastICA supported neural network
NN: neural network without data pre-processing methods

EXAMPLE 5

Training Numbers

In this experiment, various training numbers which were produced by Random Experimental Design (RED) were tested. In this experiment, no fluctuation was added. For the neural network, the number of training steps was set to 300 epochs. The nonlinear degree was set to K=2. The nonlinear functions were as follows:

$$D1=20*E1-(E2 \cdot \hat{} K)+(E3 \cdot \hat{}(K-1))-(E4 \cdot \hat{} K)+(E5 \cdot \hat{}(K-1))-(E6 \cdot \hat{} K)+(E7 \cdot \hat{}(K-1))+150; \quad (31)$$

$$D2=-27*E2-(E1 \cdot \hat{} K)+(E3 \cdot \hat{}(K-1))-(E4 \cdot \hat{} K)+(E5 \cdot \hat{}(K-1))-(E6 \cdot \hat{} K)+(E7 \cdot \hat{}(K-1))+200; \quad (32)$$

$$D3=15*E3-(E4 \cdot \hat{} K)+(E5 \cdot \hat{}(K-1))-(E6 \cdot \hat{} K)+(E7 \cdot \hat{}(K-1))-300; \quad (33)$$

$$D4=-30*E4-(E6 \cdot \hat{} K)+(E7 \cdot \hat{}(K-1))+(E1 \cdot \hat{} K)+320; \quad (34)$$

$$D5=25*E5+(E3 \cdot \hat{} K)-(E6 \cdot \hat{}(K-1))+100; \quad (35)$$

$$D6=15*E6-(E2 \cdot \hat{} K)-250; \quad (36)$$

$$D7=-30*E7+280; \quad (37)$$

$$D8=*E8-200; \quad (38)$$

According to the results obtained for the 8 dimension dataset, the training data with the larger dataset (more than 150) provided the system with better results. As the training number decreased below 150, the prediction performance was weakened. The reason is that if the training number was too low, there would be an increased chance of large gaps in the training data. The gaps could result in large prediction errors, and provide less training information for the neural network; as is evident from Table 5, pre-processing data before input into the neural network resulted in improved prediction results. Furthermore, the geneticICA supported neural network had a better prediction performance than the fastICA supported neural network.

TABLE 5

The prediction performance with various training number with Random Experimental Design (RED)

| Training number | Prediction result E(Error) | | |
|---|---|---|---|
| | fastICA_NN | geneticICA_NN | Neural Network |
| 500 | 1.3e−3 | 3.2e−4 | 0.14 |
| 250 | 1.6e−3 | 6.5e−4 | 0.02 |
| 150 | 1.7e−3 | 1.1e−3 | 0.22 |
| 100 | 0.01 | 4.0e−3 | 0.24 |
| 80 | 0.03 | 5.9e−3 | 0.49 |
| 50 | 0.05 | 0.01 | 0.49 | geneticICA_NN: geneticICA supported neural network
fastICA_NN: fastICA supported neural network
Neural Network: neural network without data pre-processing methods

EXAMPLE 6

Comparison of Processing Methods

In this experiment, the prediction precisions between the geneticICA supported neural network and neural networks supported by other data preprocessing methods were compared. The other data preprocessing methods included Nonlinear Principal Component Regression (PCR), and Nonlinear Partial Least Squares (PLS) Regression. In practice, the real concentrations of testing samples are generally unknown. In this experiment, both linear interpolation and real target values were used for validating the robustness and appropriateness of the structured approaches. Both linear and nonlinear (nonlinear degree K=2) interferences were tested and the number of training data was set to 250 with Random Experimental Design. In this experiment, no fluctuation was added. The average of relative errors between interpolation values and real values were calculated. The averages of relative errors were 0.09 and 0.16 for linear and nonlinear interference, respectively. The formulation of simulation data is shown in Table 6.

The linear interpolation was defined as:

$$E1_2=\text{interp}(D1,E1,D1_2) \quad (39)$$

$$E2_2=\text{interp}(D2,E2,D2_2); \quad (40)$$

$$E3_2=\text{interp}(D3,E3,D3_2); \quad (41)$$

$$E4_2=\text{interp}(D4,E4,D4_2); \quad (42)$$

$$E5_2=\text{interp}(D5,E5,D5_2); \quad (43)$$

$$E6_2=\text{interp}(D6,E6,D6_2); \quad (44)$$

$$E7_2=\text{interp}(D7,E7,D7_2); \quad (45)$$

$$E8_2=\text{interp}(D8,E8,D8_2); \quad (46)$$

TABLE 6

The formulation of simulation data with linear and nonlinear interference.

| Linear Interference | Nonlinear Interference K = 2 |
|---|---|
| D1 = 20 * E1 − 5E2 + 3E3 − 3E4 + 2E5 − 2E6 + E7 + 150 (mV); | D1 = 20 * E1 − (E2.$^\wedge$ K) + (E3.$^\wedge$ (K − 1)) − (E4.$^\wedge$ K) + (E5.$^\wedge$ (K − 1)) − (E6.$^\wedge$ K) + (E7.$^\wedge$ (K − 1)) + 150 (mV); |
| D2 = −27 * E2 − 5E1 + 5E3 − 5E4 + 3E5 − 2E6 + E7 + 200 (mV); | D2 = −27 * E2 − (E1.$^\wedge$ K) + (E3.$^\wedge$ (K − 1)) − (E4.$^\wedge$ K) + (E5.$^\wedge$ (K − 1)) − (E6.$^\wedge$ K) + (E7.$^\wedge$ (K − 1)) + 200 (mV); |
| D3 = 15 * E3 − 3E4 + 3E5 − 2E6 + E7 − 300 (mV); | D3 = 15 * E3 − (E4.$^\wedge$ K) + (E5.$^\wedge$ (K − 1)) − (E6.$^\wedge$ K) + (E7.$^\wedge$ (K − 1)) − 300 (mV); |
| D4 = −30 * E4 − 5E6 + 2E7 + 3E1 + 320 (mV); | D4 = −30 * E4 − (E6.$^\wedge$ K) + (E7.$^\wedge$ (K − 1)) + (E1.$^\wedge$ K) + 320 (mV); |
| D5 = 25 * E5 + 3E3 − 3E6 + 100 (mV); | D5 = 25 * E5 + (E3.$^\wedge$ K) − (E6.$^\wedge$ (K − 1)) + 100 (mV); |
| D6 = 15 * E6 − 4E2 − 250 (mV); | D6 = 15 * E6 − (E2.$^\wedge$ K) − 250 (mV); |
| D7 = −30 * E7 + 280 (mV); | D7 = −30 * E7 + 280 (mV); |
| D8 = 32 * E8 − 200 (mV); | D8 = 32 * E8 − 200 (mV); |

The geneticICA supported neural network resulted in the best prediction performance with average relative errors of $1.8e^{-4}$ for linear interference and $5.0e^{-4}$ for nonlinear interference compared with the real value. Compared with other methods, the fastICA supported neural network had the second best prediction results. For the neural network supported using the data preprocessing method of Independent Component analysis, the average relative errors between the interpolation results and the prediction results are not comparable since these methods had much higher prediction accuracy and were very close to real values. The Multiple linear regressions (MLR) were not able to predict the value for this eight dimension data system with both linear interference and nonlinear interference. Two linear regression methods were taken into consideration, Principle Component Regression (PCR) and Partial Least Squared Regression (PLSR). As shown in Table 7, it is clear that both linear regression methods have weak prediction performance. The average relative errors of prediction were more than 0.40 for not only the interpolation, but also the real values. Both Principle Component analysis (PCA) and Partial Least Squared (PLS) could improve the prediction performance of the neural network. However, the improvement was not significant when compared with methods of Independent Component Analysis. As a data preprocessing method, Independent Component Analysis applied with neural networks (neuralICA) improved the prediction ability of the neural network significantly, especially in the case of linear interference.

TABLE 7

Prediction results comparing for various methods

| | Linear | | Nonlinear | |
|---|---|---|---|---|
| Methods | Interpolation E(‖Error‖) | Real E(‖Error‖) | Interpolation E(‖Error‖) | Real E(‖Error‖) |
| PCR | 0.90 | 0.91 | 0.86 | 0.87 |
| PLSR | 0.40 | 0.45 | 0.40 | 0.43 |
| Neural Network | 0.18 | 0.16 | 0.21 | 0.18 |
| PCA_NN | 0.091 | 3.0e−3 | 0.17 | 0.13 |
| PLS_NN | 0.092 | 6.4e−3 | 0.17 | 0.13 |
| neuralICA_NN | 0.15 | 0.12 | 0.16 | 0.12 |
| fastICA_NN | 0.091 | 7.7e−4 | 0.16 | 0.016 |
| geneticICA_NN | 0.091 | 1.8e−4 | 0.16 | 5.0e−4 |

PCR: linear Principle Component Regression
PLSR: linear Partial Least Squared Regression
Neural Network: neural network without data pre-processing methods
PCA_NN: Principal Component Analysis supported neural network
PLS_NN: Partial Least Squared supported neural network
neuralICA_NN: neuralICA supported neural network
fastICA_NN: fastICA supported neural network
geneticICA_NN: geneticICA supported neural network

EXAMPLE 7

Device for Assessing the Concentration of an Analyte Ion in a Liquid

Figure 3:
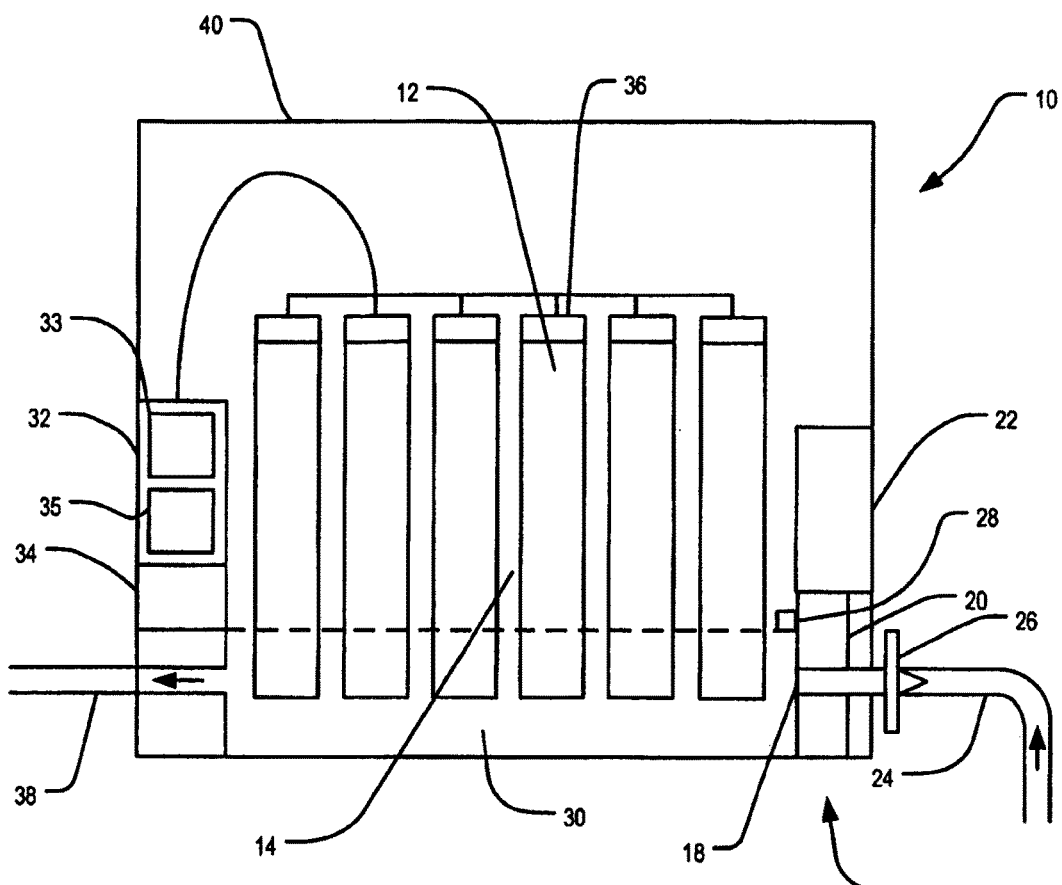
FIG. 3 is a schematic side view of a device for assessing the concentration of an analyte ion in a liquid according to an embodiment of the present invention.
Figure 4:
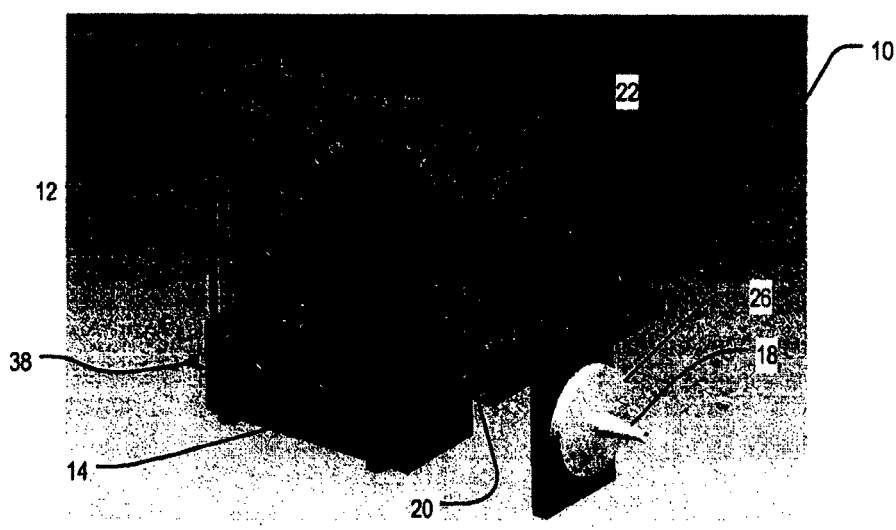
FIG. 4 is an isometric view of some components of the device shown in FIG. 3.

FIGS. 3 and 4 illustrate a device 10 for assessing the concentration of an analyte ion in a liquid according to an embodiment of the present invention. As illustrated, the device 10 includes a plurality of ion selective electrodes 12 housed in a chamber 14 of the water sampling unit 16. The water sampling unit 16 includes an inlet 18 for introducing liquid into the chamber 14. Liquid is introduced into the chamber 14 by activation of a pump 20 (200 Series Peristaltic Pump from the company of Williamson Pumps, 70 r/min, 12v DC, 1.6 mm Viton tubing), which is powered by a 12V rechargeable battery 22. Liquid is drawn by the pump 20 from its source (e.g. a river, pond or collected water sample) through a tube 24 and a filter 26 (Whatman 67255002A-01 Inline Filter Solvent IFD Inline Filter Polypropylene Pore Size 0.2 Max Volume 2.5 ml/m). The pump 20 continues to draw liquid into the chamber 14 until a liquid level detector 28 is activated. The liquid level detector 28 is positioned about 30 mm from the base of the chamber 14 and allows membranes of the electrodes 12 to be immersed in around 15 mm of liquid. Once the level of the liquid 30 reaches and activates the liquid level detector 28, the liquid level detector 28 switches the pump 20 off and activates the electrodes 12. The electrodes 12, data processing unit 32 and optional wireless data transmitter 34 are also powered by the battery 22. The electrodes 12 are connected to a data processing unit 32 via signal transmitters 36. The electrodes 12 are connected to the signal transmitters 36 via connectors, which include Female TNC/Male BNC adapters and high quality coaxial cables (RG174A/U).

Figure 5:
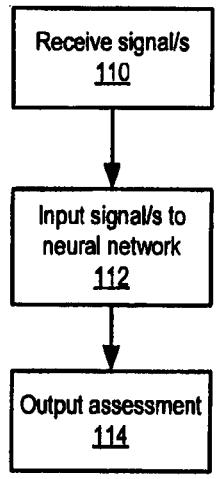
FIG. 5 is a flow chart of steps performed by software for assessing the concentration of an analyte ion in a liquid according to an embodiment of the invention.

The data processing unit 32 includes a memory 33 and a processor 35. Software for preprocessing signals obtained from the electrodes (geneticICA) and software for a Backpropagation Feed-forward Neural Network, which has been trained to calculate and/or compensate for ion interference and/or electrode interference are stored in memory 33 for execution by the processor 35. With reference to FIG. 5, the software includes a series of instructions executable by the processor 35 to perform step 110 of receiving a signal from each of a plurality of electrodes contacting the liquid, each electrode generating the signal in response to one or more ions in solution; step 112 of inputting the signal from each of the electrodes as input data to a neural network that has been trained to compensate for ion interference and/or electrode interference; and step 114 of outputting an assessment of the concentration of the analyte ion in the liquid on the basis of an output from the neural network.

If an optional wireless data transmitter 34 is included in the device 10, results from the Back-propagation Feed-forward Neural Network may be sent to a remote computer to allow a user to view, analyse or store the data. Alternatively, the data processing unit 32 may include a removable computer readable media, such as a CD, DVD, USB flash drive or other media, to allow a user to extract the results.

Once the liquid 30 has been analysed, the liquid 30 is discharged through an outlet 38 by gravity or pumping. The device 10 may include a control system (not illustrated) which controls one or more of the pump 20, electrodes 12, signal transmitters 36, data processing unit 32 and the wireless data transmitter 34. The control system may allow for the device 10 to be placed in the field (e.g. a river or water system) with the tube 24 in fluid communication with the liquid to be sampled and set to automatically sample, analyse and transmit results of analyte ions in the liquid at predetermined times. In this regard, waterways, water treatment effluent or the like may be monitored with minimal human intervention required.

The device 10 may be provided with a waterproof housing 40 to protect the battery 22, the signal transmitters 36, the data processing unit 32 and/or the wireless transmitter 34. Optionally, electric power may also be provided from an AC electricity power outlet using a (AC-DC) adjustable transformer (not illustrated).

EXAMPLE 8

Signal Transmission Setup

Figure 6:
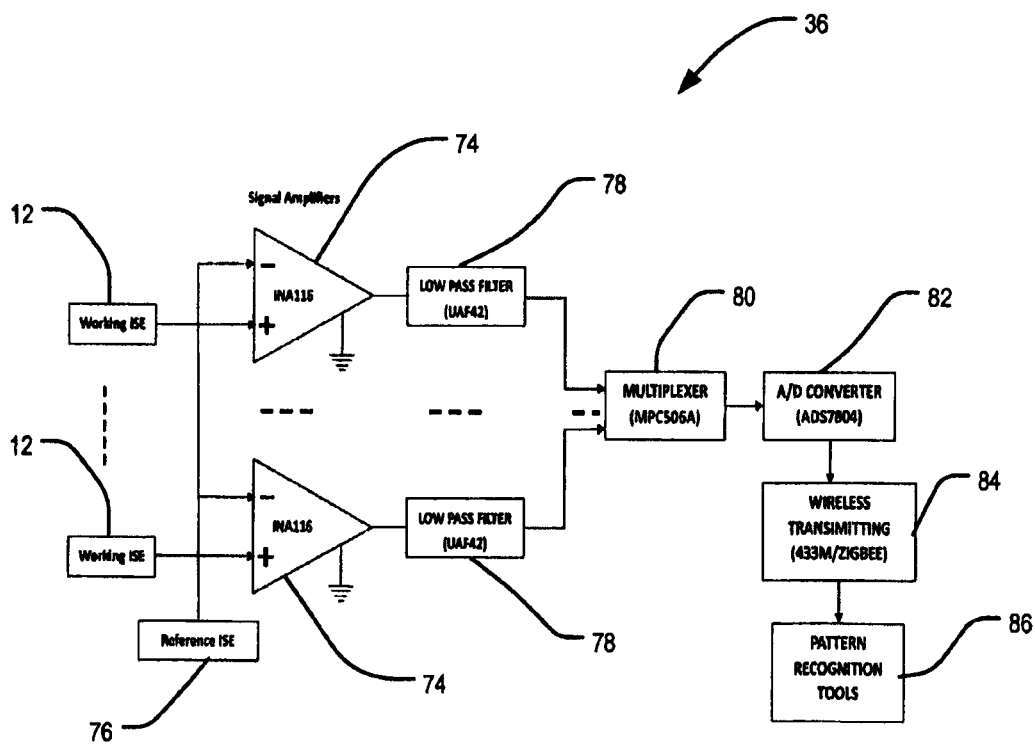
FIG. 6 is a block diagram of electronic components for performing the signal transmitting functions of the device shown in FIG. 3.

As shown in FIG. 6, the Signal transmitting device 36 contains:

a. Signal Amplifiers 74: instrumentation amplifiers (INA116) are adopted to amplify the potential values between the reference electrode 76 and each working electrode 12. INA116 amplifiers are low drift, low noise with high input impedances. These characteristics are suitable in measurement of ISEs.

b. Low pass signal filters 78: 10 Hz cutoff low pass filters, which are implemented by UAF42 universal active filters, are applied to eliminate the noise having high frequencies. With the UAF42, the background noise from both the liquid 30 and ISEs 12 is able to be minimized.

c. Signal multiplexer 80: a universal signal multiplexer, MPC506A, with digital demultiplexer is used to select the input signals for pattern recognition analysis. MPC506A is a 16-channel single-ended analog multiplexer, which contains enough channels to transmit the signal from the sensor array.

d. Analog/Digital converter 82: universal ADS7804 A/D converter with 12-Bits "No Missing Codes" and 100 kHz min sampling rate, which provides digital signal coding function with high accuracy.

Signals can be transmitted via either wired or wireless devices 84 to be processed and input into the neural network 86. For wireless signal transmission, 433M or ZIGBEE techniques can be employed. 433M is a point to point signal transmitting, which has ability to provide short distance signal transmission. ZIGBEE is a wireless technique for multi-point network with long distances signal transmission.

EXAMPLE 9

Application of the Method and Device to Water Quality Monitoring and Control of Fertigation Systems Fertigation is the application of liquid fertilizer through irrigation systems. In this regard, liquid fertilizer may be injected into irrigation water and carried to the plant root zone. Inorganic fertilizers may be commonly used due to their quick release formulations making nutrients rapidly available to plants. However, the disadvantage of inorganic fertilizer is that nutrients may be readily leached from soil by rain or irrigation.

Figure 7:
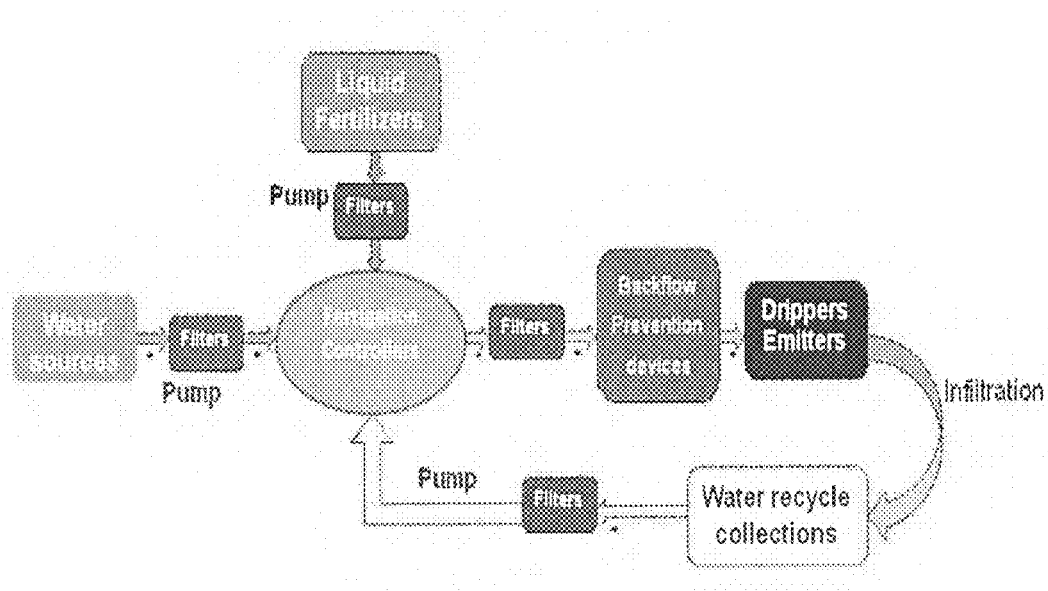
FIG. 7 shows a flow chart illustrating a fertigation system.

When fertilizers are applied to agricultural systems, not all of the fertilizers are utilized by the plants. Excess fertilizer can infiltrate into the soil and/or accumulate in aquifers, wasting fertilizer and causing pollution. Therefore, a water and fertilizer recycling system is important for fertigation systems. A block diagram illustrating fertigation systems and recycling is shown in FIG. 7. Liquid fertilizer is injected into the irrigation system and carried to the plant root zone. Excess liquid fertilizer is recollected by a water and fertilizer recycling system.

Figure 8:
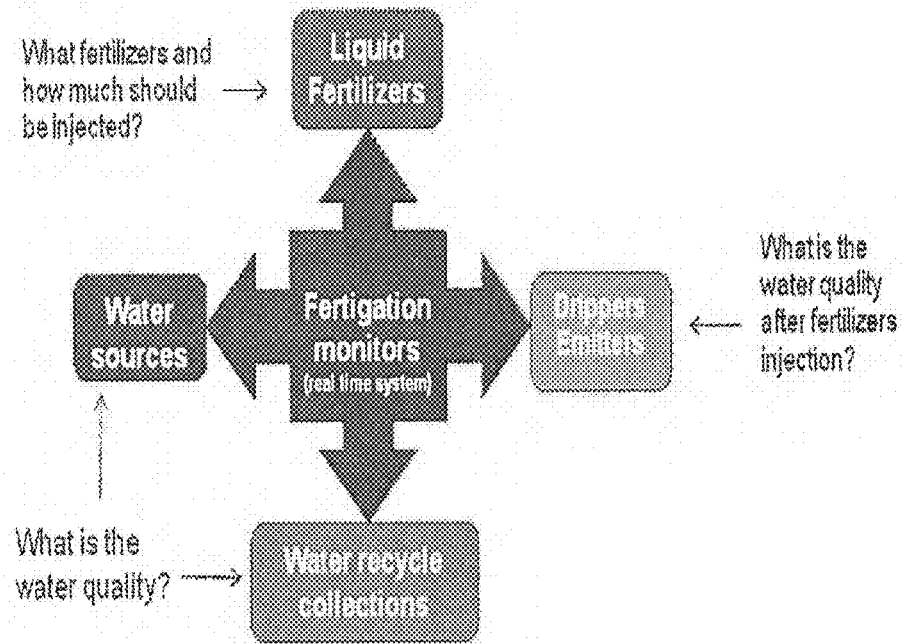
FIG. 8 is a block diagram demonstrating considerations pertaining to fertigation monitoring systems.

Issues pertaining to fertigation systems are illustrated in FIG. 8. In the fertigation system, fertigation monitors or controllers may be used to fine tune the water quality in term of pH, electrical conductivity and nutrients for each stage of plant growth. To fine tune the water quality which is applied to plants, it is necessary to know which and how much fertilizer should be added into the system. In order to control the amount of fertilizers, it is also important to know the water qualities of irrigation water sources and recycling water sources. Furthermore, after fertilizers are injected into the system, it is important to monitor the water quality which is exposed to the plant root zone. A real time in-situ water quality monitoring system has the potential to improve fertigation systems. Embodiments of the present invention may therefore be particularly suitable for assessing water quality in one or more stages in fertigation systems.

To demonstrate this suitability, an array of ion-selective electrodes, according to embodiments of the present invention, was used for the simultaneous determination of multiple free ions in solution in an in-situ water quality monitoring process. The method and device according to embodiments of the present invention were capable of predicting the concentration of ions in an unknown solution.

Water quality of irrigation water is usually analyzed for Electrical Conductivity (EC), which is a measure of the total soluble salts in the water. Sodium Adsorption Ratio (SAR) may also be used, which is a measure of the level of sodium relative to calcium and magnesium ions present. Inorganic fertilizers may include macronutrients which include primary components (nitrogen, phosphorus and potassium) and secondary macronutrients (calcium, sulfur and magnesium). Nitrogen containing fertilizers may include nitrate fertilizers and ammonium fertilizers. Various concentrations of chloride may also be present in water used in fertigation and/or irrigation. Accordingly, important ions which may be desirable to monitor in fertigation systems include: sodium, magnesium, calcium, potassium, ammonium, nitrate, phosphorus, chloride, sulfur.

EXAMPLE 10

Simultaneous Quantitation of Multiple Free Ions in Solution by Ion Selective Electrode Array The type of exchangeable ions present in irrigation water plays a role in the yield and quantity of crops, maintenance of soil productivity, and protection of the environment. The interaction and interferences between these ions and/or electrodes has previously limited the utilization of relative ion selective electrodes.

With this in mind, embodiments of the present invention were investigated for their ability to provide simultaneous determination of multiple ion concentrations using an Ion Selective Electrode (ISE) array for in situ monitoring. The experiment was based on Orthogonal Experimental Design (OED) and Artificial Neural Network (ANN). The multiple ions for detection were sodium, potassium, calcium, ammonium, chloride and nitrate. By building up a neural network with Genetic algorithm supported Independent Component Analysis (geneticICA), the determination results were rapidly and accurately analysed without perturbing the natural speciation. The concentrations of sodium (pNa) and chloride (pCl) that could be quantified were between $10^{-1}$ M and $10^{-4}$ M. The concentrations of potassium (pK), ammonium (pNH$_4$) calcium (pCa) and nitrate (pNO$_3$) that could be quantified were between $10^{-2}$M and $10^{-5}$M. Logarithmic calibration of the ISEs was carried out by immersing the ISEs into a solution of known concentration, then comparing the mV reading versus the concentration value in $10^x$M, based on the linear response rules of ISEs. When configured and optimized, the approach based on the geneticICA pre-processing arrangement was able to reduce the mean relative error between the predicted concentration and the actual concentration to 0.05 on average in a logarithmic way. This analysis confirmed the efficacy of the chosen strategy and method.

8 pH amplifiers (ADINSTRUMENTS Co.) were utilized as signal amplifiers and a PowerLab (ADINSTRUMENTS Co.) used to interface the computer with the amplifiers. A personal computer with Windows XP professional operation system was employed for system management and signal analysis. Windows application software named Chart5 (ADINSTRUMENTS. Co) was used in the data acquisition and filtering.

Finally, data processing and analysis was implemented in MatLab 6.0 using Statistical Analysis and neural network toolboxes. A chemometrics toolbox for Matlab (The MathWorks, Inc) was adopted for data preprocessing. SPSS 15.0 for Window was employed for generating the Orthogonal Experimental Design. The sensor array included 9 commercial electrodes from pHoenix: one sodium electrode (NA71501); one potassium electrode (KO01501); one ammonium electrode (NH41501); one calcium electrode (CAL1501); two water hardness electrodes (WHA1501); one chloride electrode (CL01501); one nitrate electrode (NO31501); and one reference electrode. One magnetic stirrer (IEC, C876083V) with a spin bar and several beakers (SCHOTT DURAN 250ML) were used for the samples and preparation of standards.

The pH amplifiers were connected using the I²C bus in order to share the same temperature (20° C.), potentiometric value from the reference electrode and the earth reference. The noise resulting from the signal granularity generated by ions was removed by a 10 Hz low-pass digital filter. The electrode tips were positioned in the solution about halfway between the center of the beaker and the beaker wall. Two points of calibration with standard solutions was carried out every hour. Containers and electrodes were carefully rinsed three times with the MQ water at each stage in an attempt to remove the physisorbed species of the electrical double later and to prevent the electrode cross-contamination. During the measurement, electrode membranes were always checked to make sure that they were free from air bubbles after immersion into the standard or sample. The potential value from the electrodes were recorded provided the potential became stable (The deviation $\Delta V$ of potential value $<\pm 0.01$ mv/s). Each training sample measurement was repeated three times and the average values were calculated and recorded. Calibration with standard solutions was carried out each time a new sample was measured.

All experiments were carried out at 20° C. The samples for orthogonal experimental in the range of $10^{-4}$ to $10^{-1}$ M were diluted and combined with 1 mol/L of sodium chloride, sodium nitrate, potassium chloride, calcium chloride, magnesium chloride and ammonium chloride, respectively. Milli-Q water (Milli Q plus System, Millipore, Bedford, Mass. USA, with 18.2 M$\Omega$ cm$^{-1}$ resistivity) was used in the preparation of all aqueous solutions. The pH value was in the range of 5.5 to 6.5 (measured by the Orion's pH electrode). In the nine-ISE array, six chemicals with seven ion concentrations were investigated: pNa, pK, pMg, pCa, pNH$_4$, pCl and pNO$_3$. These are shown in Table 8. Assuming that each ion had four different levels of concentrations from $10^{-6}$M and $10^{-3}$M, the total number of training combinations would be $4^6=4096$.

Figures 9, 10:
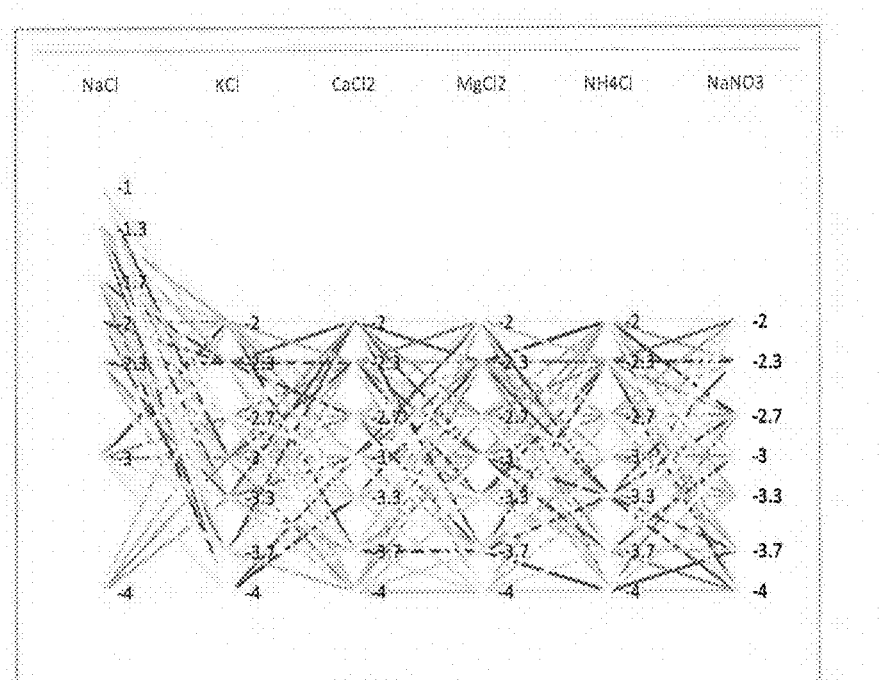
FIG. 9 shows a graph of an orthogonal experimental design used according an embodiment of the present invention.
FIG. 10 is a table showing the Pearson Correlations between ions and electrodes according to an embodiment of the present invention.

Such a large number of training samples is time prohibitive. Therefore, how to group up the training dataset with minimum number of samples and get maximum information was a key issue in building up the Neural Network determination system. An Orthogonal Experimental Design (OED) was employed to reduce the number of training samples without losing quality characteristics for the specific ions. By using Orthogonal Experimental design with $L_{49}$ ($7^6$) for the six chemicals with seven levels of concentration, the number of combination groups could be reduced to 49, as illustrated in FIG. 9. To optimize the prediction system, we used another 20 samples as a testing sample set, which randomly combined the ions with various levels of concentrations. The system was trained in a logarithmic way, and the prediction results were also logarithmic. This is because the ISEs provide a logarithmic linear response to the concentrations of their desired ions.

TABLE 8

Chemicals, concentration range and free ions

| Chemicals | Range | Ions |
| --- | --- | --- |
| NaCl | 0.1M~$10^{-4}$M | Na$^+$, Cl$^-$ |
| KCl | $10^{-2}$M~$10^{-4}$M | K$^+$, Cl$^-$ |
| MgCl$_2$ | $10^{-2}$M~$10^{-4}$M | Mg$^{2+}$, Cl$^-$ |
| CaCl$_2$ | $10^{-2}$M~$10^{-4}$M | ca$^{2+}$, Cl$^-$ |
| NH$_4$Cl | $10^{-2}$M~$10^{-4}$M | NH$_4^+$, Cl$^-$ |
| NaNO$_3$ | $10^{-2}$M~$10^{-4}$M | Na$^+$, NO$_3^-$ |

The Pearson Correlation value from 49 samples shows the relationship between the ISEs and ions. As shown in the FIG. 10, it is evident that all the electrodes react with other undesired ions. The relationships can therefore represent the interferences. The positive Pearson Correlation values indicate that the response value from electrode would increase when the concentration of interference ions increases; and the negative Pearson Correlation values indicate the response value would decrease when the concentration of interference ions increases. It is evident that the highest interference belongs to potassium ion against the ammonium ISE, with a Pearson Correlation value of 0.26. This means that the prediction result of ammonium could be doubled if the pK was four times higher than pNH$_4$. Both ISEs of calcium and two water hardness had the highest response to pCa. Nevertheless the two water hardness ISEs were more sensitive to the pMg, which were 0.14 and −0.12 respectively. Chloride is the most interfering ion in the group, which provided more than 0.1 Pearson Correlation value of relationship to four of the ISEs: ammonium, calcium, nitrate and one of the water hardness (W.H.1). A further water hardness ISE (W.H.2) was the most sensitive to other ions, with an average Pearson Correlation value from undesired ions of −0.12. As shown in FIG. 10, there was no single ISE whose response was based on pMg. Instead, the prediction of pMg was based on the interference relationships from the ISE Array.

Figure 11:
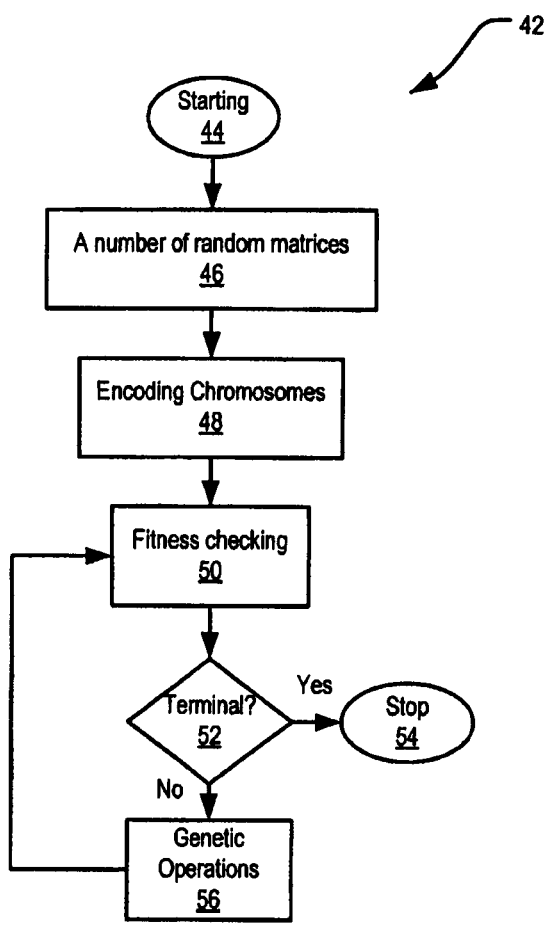
FIG. 11 is a flow chart of a geneticICA algorithm used according to an embodiment of the present invention.

In this work, geneticICA was used, which involved the implementation of fastICA by Genetic Algorithm. The data used for geneticICA analysis was zero mean and whitened data. To whiten the data, the raw data from the sensor array was firstly adjusted by centering and covariance calculation. After adjustment, the data in all eight dimensions was zero mean normalized and the covariance was calculated. Secondly, Principal Component Analysis (PCA) was employed to remove the correlations between data and, at the same time, find directions with maximal variance. Finally, the data was normalized, such that the square root of the normalized data would be equal to 1. To produce independent components (ICs) with minimized both linear and nonlinear interference, Independent Component Analysis (ICA) was adopted by maximizing the statistical independence of the estimated components (ICs). In the ICA, the genetic improved fixed-point algorithm (named geneticICA), was applied so as to separate the signals from their nonlinearly interfering components. To configure the genetic algorithm, the maximum number of generations was set to 500. In one generation, the population was set to 40. The data that was used for geneticICA analysis was the zero mean and whitened data matrix Z. A flow chart showing a method of performing geneticICA is shown in FIG. 11. The method starts at step 44. At step 46, to create the "Chromosomes" (proposed solutions) for the genetic algorithm, 40 separating matrices W with unit norm random values are initialized and orthogonalized. At step 48, these 40 matrices are encoded into "Chromosomes", one "Chromosome" for each separating matrix W. In every generation, the fitness value of each "Chromosome" is calculated and checked at step 50. If the fitness value is assessed at step 52 as satisfying accuracy criteria, or if the breeding for "offspring" reached the maximum number of generations then the Genetic Algorithm would stop at step 54. Otherwise, "offspring" of parent "chromosomes" selected using Stochastic Universal Sampling (SUS), would be recombined at step 56 using multi-point crossover and each element mutated with a probability of 0.7. Each "chromosome" presented one possible separating matrix W, which would be transformed into a vector Chr, $$Chr_{i*n+j} = W_{i,j} \qquad (47)$$

Where n is the number of values contained by one of vectors $w_i$ in separating matrix W. In each "chromosome", the geneticICA would calculate a relative $W_{new_j}$ by using function (48)

$$w_{new_j} = E\{zg(w_i^T z)\} - E\{g'(w_i^T z)\}w_i \qquad (48)$$

Where for every $w_{new_j}$ in $W_{new}$

The nonlinearity of pow3 (g(x)=x^3) was applied for IC extraction. The fitness value was measured by how close $W*W_{new}^T$ is to identity. The "chromosome" whose $W*W_{new}^T$ is closer to identity, the better fitness value it has. After geneticICA, the covariance between ICs was cut to zero.

To optimize the robustness and appropriateness of the ANNs, the Mean of the Relative Error of the testing sample set was used. The Mean of Relative Error, E(|Error|) was as follows:

$$E(|\text{Error}|) = \frac{1}{n_{Test}} \sum_{i=1}^{N_{Test}} \left| \frac{C_i - C_i'}{C_i} \right| \qquad (49)$$

In equation (49), $C'_i$ indicates the $i_{th}$ predicted value, the $C_i$ indicates the $i_{th}$ true concentration and $n_{Test}$ denotes the number of the test data subset.

After optimizing the performance of the Back-propagation Feed-forward Neural Network (BPNN), the architecture of the ANN model was set as 8×30×7 BPNN (As illustrated in FIG. 2).

The neural network included one input layer with eight input neurons (one neuron for each IC); one hidden layer with 30 hidden neurons; one output layer with seven output neurons, in which every output neuron provides predicted prediction values for each expected element, respectively. The tangent sigmoid transfer function (Tansig) was used as the transfer function for the hidden layer. The linear purelin transfer function was employed as the output function for the output layer. The training parameters were set to 100 epochs maximum, with the fixed error goal of the Root of Mean Square Error (RMSE) (50)

$$RMSE = \sqrt{\frac{\sum_{i=1}^{n}(C_i - C_i')^2}{n}} \qquad (50)$$

In this equation, n is the number of samples in the data set, $C_i$ is real actual value of the $i_{th}$ number of sample, $C'_i$ is the predicted value of the $i_{th}$ number of sample. The weights and biases of the ANN were initialized randomly and applied. The training function used was the Bayesian regularization backpropagation training function <TRAINBR>.

The prediction results of 20 testing samples are shown in FIG. 12. The result was a logarithmic value since the system was trained in logarithmic way. The best prediction results belong to pK, pCa and pNO$_3$, whose E(|Error|)s were 0.01, 0.02 and 0.03, respectively. Magnesium had a high relative error as no Magnesium selective electrodes were used. As such, magnesium was calculated based only on the interference relations from the ISE Array. Excluding magnesium, the average prediction precision was lower than 0.05 of E(|Error|).

To validate the system, three field samples were analysed. Two of the samples were from Mawson Lakes in South Australia (M.L.1 and M.L.2) and one was from the River Torrens in South Australia. The prediction results were validated by ICP/IC. The results are shown in FIG. 13.

The ICP-OES conducted for the exchangeable cations and IC-MS was conducted for chloride and nitrate. The samples prepared for ICP-OES were diluted by 50 times, and the samples prepared for ICS were diluted by 100 times, which would bring errors for the results. Analysis of each sample was repeated three times for both the ISE-array and ICP/IC. A magnesium selective electrode was unavailable at the time of the experiment. The difference of results between ISE-array and ICP/IC was larger when converted to milligram per liter (mg/L). The reason was that the ISEs responded to the desired ions in logarithmic linear way, and the ISE-array system was trained in a logarithmic way as well. For sodium, potassium, calcium, chloride and nitrate, the prediction capability was lower than 0.06 of E(|Error|) on average using the logarithmic determination of moles per liter and around 0.18 of E(|Error|) on average for the milligrams per liter results.

EXAMPLE 11

Summary

Irrigation water quality is very important to promote crops and plants. Irrigation water quality could be monitored online in situ by using methods and/or devices in accordance with embodiments of the present invention. As demonstrated by the data presented above, essential macro-elements in irrigation water can be simultaneously determined using the methods and/or devices with acceptable error levels. Macro-elements that may be tested include, for example, sodium, potassium, ammonium, calcium, chloride and nitrate.

The present methods and devices may be used to provide simultaneous determination of multi-free ions for online in-situ water qualities assessment. In this regard, the methods and/or devices may be applied to ion specific fertilizer monitoring. While farmers are currently able to monitor soil moisture and salinity, they aren'table to conduct real time nutrient monitoring. Furthermore, the methods and/or devices may be used for environmental purposes, such as waste water management or nutrient monitoring of freshwater waterways and reservoirs.

EXAMPLE 12

Data Modelling

The purpose of this modeling is to evaluate the robustness of a pattern recognition method (named 'Io deTech') according to an embodiment of the invention. The proposed methodology is employed in an electronic tongue system for quantitative analysis of several ions. As shown in FIG. 30, in this proposed approach, the response values from the working ISEs were centrally adjusted by removing the average values. Principal Component Analysis (PCA), as the signal whitening method was employed to eliminate any linear interference. By finding eigenvectors and eigenvalues, the PCs represent the improved signals obtained by minimizing their mutual linear correlation (PCA is normally implemented by the algorithm of Singular Value Decomposition (SVD), as mentioned above). By using SVD, Principal Components, which contain variance information, can be represented by pairs of eigenvalues and eigenvectors. Eigenvectors represent the directions of the new data coordinate system, whereas eigenvalues indicate variance contained in the observed data of each PC. The eigenvector with the highest eigenvalue indicates the most important principal component (PC) of the data set. After PCA, in order to implement Independent Component Analysis (ICA), since the Independent Components (ICs) are mutually orthogonal, there is no linear correlation between the ICs. The ICs were utilized as the input for the Artificial Neural Network (ANN).

To facilitate testing for the robustness, simulated data is processed and described with reference to two dimensional data. The modeling focused on simulating the true potential response values from an array of ion-selective electrodes in a system similar to electronic tongue systems to predict the concentrations of target ions.

The input data represents the ISE's sensor responses to different combined concentrations of ions ($E_i$). The range of ISEs' measurement ranges normally from the $10^{-6}$M of magnitude to the $10^{-1}$ M. Additionally, the concentration of ions, corresponding to the measured potential, is described by the Nernst equation. Since the ISEs are Nernstian responses to the concentrations for the selected ions, in this simulation, the data ($E_i$) were set up between 6 and 1 for each ion, which represents the logarithmic concentrations (3.1.1)~(3.1.3)

$$C_{i_{mol/L}} = 1.0 \times 10^{(-E_i)} \quad (3.1.1)$$

$$E_i = -(\log^{C_i}) \quad (3.1.2)$$

$$C_{i_{mg/L}} = \frac{C_{i_{mol/L}} \times W_i}{1000} \quad (3.1.3)$$

Where:
$C_{i_{mol/L}}$—denotes the concentration of the ith ion in moles per liter unit;
$C_{i_{mg/L}}$—denotes the concentration of the ith ion in mg/L unit;
$W_i$—denotes the molecular weight of the ith ion.
Assuming that the simulation data for each ISE (a) is linear in response to E (3.1.4):

$$Dj_i = mj_{Ei} \times E_i \quad (3.1.4)$$

Where:
$Dj_i$—denotes the simulation data for the jth ISE;
$mj_{Ei}$—denotes the sensitivity of the jth ISE to the ith ion;
Interference effects are commonly described as the semi-empirical Nicolsky-Eisenman equation (otherwise spelt as the Nikolsky-Eisenman equation), an extension of the Nernst equation. Therefore, the formula for simulating data for each $D_i$ with interference is presented (3.1.5):

$$Dj_i = mj_{Ei} \times Ej_i + \Sigma(mj_{Ek} \times g(Ek_i)) \quad (3.1.5)$$

Where:
$mj_{Ei}$—denotes the sensitivity of the jth ISE to the ith ion;
$g(Ek_i)$—denotes the formula of interference from interfering ion (Ek).
To validate the approach, simulation data is separated into training data and test data. Training data is utilized to build up the prediction system, and the validation data estimates the robustness and appropriateness of the structured approach. The prediction accuracy is assessed by the Mean of Relative Errors (MRE) (3.1.6a), $$MRE(C_j(i)_{True}, C_j(i)_{Predicted}) = \quad (3.1.6a)$$

$$\frac{1}{N_{Test}} \sum_{i=1}^{N_{Test}} \left| \frac{C_j(i)_{Predicted} - C_j(i)_{True}}{C_j(i)_{True}} \right|$$

Where:

$C_{j_{Predicted}}$—denotes the predicted concentration of the ion X (moles per liter); and $C_{j_{True}}$—denotes the true concentration of the ion X (moles per liter); and $N_{Test}$—denotes the number of the test data subset.

Considering the fact that the primary measurement, the sensor system are logarithmic responses Ei, for convenience the relative error in Ci throughout this simulation is calculated as mean error, $\Delta E_i = E_i$, calculated $-E_i$, true.

Conveniently, for small value of the relative error $|\Delta C/C| \ll 1$ we have a direct relationship between the relative error (3.1.6a) and the calculated error (3.1.6b), following the differential relation:

$$|dE| = \frac{1}{\ln 10} \left| \frac{dC}{C} \right|,$$

hence:

$$MRE(C_j(i)_{True}, C_k(i)_{Predicted}) \cong \ln 10 \times \frac{1}{N_{Test}} \sum_{i=1}^{N_{Test}} \left| \frac{E_j(i)_{Predicted} - E_j(i)_{True}}{E_j(i)_{True}} \right| \quad (3.1.6b)$$

Certainly, for the relative errors exceeding a few percent the relation between the two error measures $|\Delta E|$ and $|\Delta C/C|$ is no more linear, i.e.:

$$|\Delta E| = \frac{1}{\ln 10} \ln\left(1 + \left|\frac{\Delta C}{C}\right|\right).$$

Additionally, MRE produced by the standard linear interpolation on the training data was used to assess the performance of the method. In the linearity simulation, different linear interfering degrees from other undesired ions were simulated. The simulation formula is shown below (3.1.7)

$$Dj_i = mj_{Ei} \times Ej_i + \Sigma(mj_{Ek} \times 10^C \times Ek_i) \quad (3.1.7)$$

Where:

$Dj_i$—denotes the simulating data for the jth ISE;

$mj_{Ei}$—denotes the sensitivity of the jth ISE to the selected ion;

$mj_{Ek}$—denotes the sensitivity of the jth ISE to the kth interfering ion;

C—denotes the linear interfering degree from ion $Ek_i$.

Different levels were investigated (C=1, 2, 3) in order to simulate different sensitivities of ISEs to varying undesired ions. The higher degree interferences indicated more a severe interference from the undesired ion.

In the non-linearity simulation, exponential interferences from other undesired ions were employed. The simulation formula is shown in (3.1.8):

$$Dj_i = mj_{Ei} \times Ej_i + \Sigma(mj_{Ek} \times Ek_i^C) \quad (3.1.8)$$

Where:

$Dj_i$—denotes the simulating data for the jth ISE;

$mj_{Ei}$—denotes the sensitivity of the jth ISE to the ith ion;

$mj_{Ek}$—denotes the sensitivity of the jth ISE to the kth interfering ion;

$Ej_i$—denotes sample solution contain the $i_{th}$ negative log of concentration of Ej;

$Ek_i$—denotes sample solution contain the $i_{th}$ negative log of concentration of interfering ion Ek;

C—denotes the exponential interfering degree from ion $Ek_i$.

Different exponential levels were taken into investigation (C=2, 3, 4), in order to simulate the different sensitivities of ISEs to different undesired ions in non-linear interference situations. The higher exponential interferences indicated more severe interference from the undesired ion.

To investigate the errors brought by the interferences, The Interfering Rate (IR) were employed and defined as (3.1.9):

$$IR = \frac{1}{N_{Test}} \sum_{i=1}^{N_{Test}} MRE(D_i, D_i') \quad (3.1.9)$$

Where:

$MRE(D_i, D_i')$—denotes the mean of relative errors for the response values of ISE with and without interference;

$D_i$—denotes the response values of ISE without interference;

$D_i'$—denotes the response values of ISE with interference.

For simulating two dimensional data, it is assumed that there is only one desired ion $E_1$ with one undesired similar interfering ion $E_2$. The testing samples contain only these two ions (E1, E2). The array of ion-Selective electrodes (ISE) only contains two working electrodes. One working electrode had a linear response to ion E1 and is interfered by ion E2; another working electrode had a linear response to ion E2 but without any interference. To simulate the response of ISEs', it is assumed the formulae of data from electrodes (D1, D2) are as below (3.2.1)~(3.2.3):

$$D1_i = m1_{E1} \times E1_i + m1_{E2} \times g(E2_i) \quad (3.2.1)$$

$$D2_i = m2_{E2} \times E2_i \quad (3.2.2)$$

$$Sample_i = [D1_i, D2_i] \quad (3.2.3)$$

Where:

$mj_{Ei}$—denotes the sensitivity of the jth ISE to the ith ion;

$g(E2_i)$—denotes the formula of interference from ion E2.

In a pure linear simulation scenario, no noise was applied and the interference $g(E2_i)$ was linear. The linear functions were set out as below (3.2.4), (3.2.5):

$$D1_i = -10^2 \times E1_i - 10^{c-1} \times E2_i \quad (3.2.4)$$

$$D2_i = -10^2 \times E2_i; \quad (3.2.5)$$

Where: c—denotes the linearity degree of interference

Network optimization has been done in each modeling step. To optimize of the Neural Network topology using the approach PCA_ICA_ANN ('Ion deTech'), all neurons of hidden layer numbered from 6 to 23 were parallel trained, and the trained network performance was compared by the MRE value of the validation subset. Two Neural Network transfer functions, tangent sigmoid transfer function (Tansig) and Log Sigmoid transfer function (Log sig) were involved for election. The processed data after PCA and ICA were applied as the input for ANN. The linear degree was set at C=2. The prediction performance of every Neural Network was estimated and repeated for 20 times, which the mean MRE (Mean of Relative Errors) value of each ANN with one standard deviation. Following the neuron number increasing from 6 to 12, prediction errors decreased tremendously. Nevertheless, the prediction performance ameliorated slightly following the number increase to 20. After the number reached 21, the redundant hidden neurons did not furnish any benefit to ANN prediction. In the observation, ANN models with the Tansig transfer function, offered lower prediction errors than the Log sig transfer function. The highest prediction accuracy belonged to the ANN model, whose structure comprised: one input layer with two input neurons, one neuron of each data dimension; and 20 neurons in the hidden layer with Tansig transfer function. The output layer consisted of two output neurons with linear transfer function (purlin). In addition, based on the same ANN architecture, the performances of different training functions were also investigated. The weights and biases of the ANN were initialized randomly before applying the training functions. Each training function was also investigated repeated 20 times using different data set and the Bayesian regularization training method (BR) offered better prediction accuracy than the others.

The linear 2D interpolation was employed to compare the prediction capability of the 'Ion deTech' approach. The principal of linear interpolation is choosing the two nearest training data points for each validation data to calculate the results, without knowing the interfering relationship. In this simple linear interfering two data dimension scenario, the linear interpolation had no error in predicting the ion concentrations.

When the linear interference degree increased, the interference from second ion (E2) was taking up mainly information which the first data dimension (D1) afforded, and both dimensions of data (D1, D2) would become mainly responsive to E2. Principal Component Analysis transfers the original observed data into a new coordinate system to afford better sight into the relationship. After PCA and ICA, the linear relationship between the first and the second component has been eliminated. The data extraction ability was exhibited clearly in ICA score plots. The two independent components, extracted from ICA, were adopted as the input for the Neural Network. Also, the interfering rate had no impact on the prediction performance of the 'Ion deTech' approach, since the linear data variation was found easily by PCA and ICA.

A participating fluctuations stage analyzed the impact of the noise generated by the system and its measurements. Based on the previous stage, different degrees of fluctuations were participated for simulating errors. It is defined here that fluctuation F is the zero mean random number within a limiting range. The fluctuations, equivalent to random calibration noise, were included as both testing data and training data. The equation of fluctuation is represented as (3.2.6), (3.2.7):

$$Fj_i = (Rand(0:1) - 0.5) \times 10^{C-2} \quad (3.2.6)$$

$$Ej_i' = Ej_i + Fj_i \quad (3.2.7)$$

Where:
$Fj_i$—denotes the fluctuation of $j_{th}$ ion on the $i_{th}$ sample solution;
C—denotes the degree of fluctuations;
Rand (0:1)—denotes a random number between 0 to 1;
$Ej_i'$—denotes the ion concentration with calibration errors of $j_{th}$ ion on the $i_{th}$ sample solution.

The $2^{nd}$ linear interfering degree was applied and the same ANN structure was employed. There are 3 different degrees of fluctuations (C=1, 2, 3), and the influence of fluctuation was investigated by the Interfering Rate (IR) between with and without fluctuation. This formula is mentioned in (3.1.9).

The 'Ion deTech' approach was estimated using different degrees of fluctuations. Each degree of fluctuation was repeated 20 times, and the average performance accuracies (Mean of Relative Errors) for each fluctuation degree with one standard deviation were calculated. Linear interpolation was also employed for comparison. It is evident that the fluctuation offered tremendously negatively impacts on the prediction accuracy of 'Ion deTech' approach. PCA_ICA has no capability to banish the fluctuation since the fluctuation is random. Even when the fluctuation was only at 0.01 of IR, this introduced significant errors into the prediction system. When the fluctuation increased up to the second degree (0.10 of Interfering Rate), the prediction abilities of both the 'Ion deTech' approach and linear interpolation were completely amiss. This is explained by the fluctuation taking up the major part of the information, and there is no proper data variation for PCA and ICA to find the relationship. Compared to the linear interpolation, whose prediction performances were seriously impaired by the fluctuation, the 'Ion deTech' approach offered a much better prediction in this fluctuation modeling stage.

The prediction performance was also modeled in non-linear interference scenarios. With the same ANN structure and same size of training and validation data sets, no fluctuation was affiliated both in training data and testing data. The different exponential degrees of non-linear interferences were employed for D1 (3.2.8):

$$D1_i = 100 \times E1_i - 3 \times E2_i^C \quad (3.2.8)$$

Where:
$D1_i$—denotes the $i_{th}$ response value from the first ISE;
$Ej_i$—denotes sample solution contain the $i_{th}$ concentration of EJ;
C—denotes the non-linear interference degree from ion $E2_i$.

In this case, similar to linear interfering scenarios, as mentioned in the first step, when non-linear interference degree increased, the interference from second ion (E2) began to take up information afforded by the first data dimension (D1). Both dimensions of data (D1, D2) became mainly responsive to E2. Principal Component Analysis (PCA) did not offer interference elimination in the data, hence there is no linear relationship between the two dimensions of data. Independent Component Analysis (ICA) has strong capability for high order polynomial non-linear formula data extraction, even with large interfering rate. It was determined that ICA score plot presented the data with more separation than the PCA score plot. The non-linear interference impaired the system prediction accuracy, especially when the concentration of ion E1 is too low and the concentration of ion E2 is too high. Although interferences were non-linear, the interpolation still offered reasonable results when the non-linearity degree was low. This is because the linear interpolation employs the nearest two data points from the training data for calculating the validation data. The good interpolated results could still be offered when the nearest two points had sufficiently small distances to each validation data point, apart from there being a low exponential degree of the non-linear interference. The interpolation failed completely when the non-linear interference was increased to the fourth degree.

In a fourth simulation step, the aim of surveying the size of the training data is to estimate what is the sufficient number of training samples that will satisfy the system training. In this step, retaining the ANN structure same as before, while the training data sizes being studies were gradually reduced from 200 to 20. The validation set was fixed at 60, and fluctuation was not included. The $2^{nd}$ order polynomial non-linear interference from E2 was applied to D1 and the formula used as at (3.2.10), in which the Interfering Rate 0.14.

Estimation of each training data size was repeated 20 times. The prediction accuracies were studied with Mean of Relative Errors (MRE), Maximum Relative Error (Max RE) and Minimum Relative Error (Min RE). The training data size in this case did ameliorate the prediction capability of the system. The best training number for the system was 200, which had the MRE at $10^{-3}$ level. There was modest improvement when the training number increased from 60 to 200. However, the prediction ability was impaired significantly when the number of training samples fell to below 40. Therefore, a suitable number of training samples is important for optimizing the system prediction ability. If the number was insufficient, the gaps between training data could not contribute enough information to the system. On the other hand, the large redundant training data would bring more complexity to the system, and improved the prediction accuracy inefficiently. The interpolating accuracy corresponds to the distance between each validation data and its nearest two training data points. A smaller training data set could increase the average distance between the two nearest training data points and consequently weakens the interpolating performance.

In a fifth stage, other well-known quantitative analytical methods for ET systems were surveyed for comparison. As mentioned above, these methods could be categorized into linear regression methods and Neural Network methods. The linear regression methods include: Multiple Linear Regression (MLR), Principal Component Regression (PCR), and Partial Least Squares (PLS) Regression. The Neural Network methods include the ANN with data mono-preprocessing methods, such as PCA and PLS. Both the first level (C=1) linear interference and the third order of non-linear interference (C=3) were investigated. The comparison between the chosen method and the other Neural Network methods were based on the same architecture of ANN model. The number of training data was set at 200, and the validation data size was 60. No fluctuation was taken part into either training data or validation data.

It was found that all linear regression methods except Principal Component Regression (PCR), offered no and low prediction errors for linear interference and non-linear interference, respectively. Neural Network approaches could offer better prediction performance in non-linear interference than linear regression methods. In addition, the prediction capacities of ANNs were improved by introducing either PCA or PLS as the preferred data mono-preprocessing method. Based on the validation results, in the linear interfering scenario, the 'Ion deTech' approach offered the best prediction abilities in all Neural Network methods. Regarding the non-linear interference situation this approach offered the highest prediction overall accuracy.

In conclusion, the above modeling focused on simulating the potential response values from an array of ion-selective electrodes in ET systems to predict the concentrations of target ions. The simulation included evaluating both linear and non-linear interferences with different degrees, various sizes of the training data and the 'noises' from both system and measuring mistakes. From the prediction results and data analysis, it has been confirmed that with the assistance from the PCA, the Independent Component Analysis (ICA) can extract further information from the data, and ameliorate the prediction ability of Artificial Neural Networks.

In the ANN optimization, the optimization of the number of the hidden neurons was important to offer high prediction accuracy. The higher dimensional was the data simulation, the more hidden neurons were needed. However, following the increase in the hidden neuron numbers, the redundant hidden neurons did not benefit ANN prediction. In the conclusion, the ANN models with the Tansig transfer function, offered lower prediction errors than the Log sig transfer function. The output layer consisted of output neurons with linear transfer function (Purlin). Furthermore, based on the same ANN architecture, the abilities of different training functions were investigated. The weights and biases of the ANN were initialized randomly before applying the training functions. It was illustrated that the Bayesian regularization training method (BR) offered higher prediction accuracy than other system.

In the pure linear interference simulation, three logarithmic different degrees of linear interferences were evaluated. The 'Ion deTech' approach has a strong ability to simultaneously determine the multi-ion concentrations in the pure linear interference scenario, even though the degree of linear interference negatively impacts on the prediction capability of this approach. The higher the data dimension, the less prediction precision. The reason is the increasing complexity of the relationships involved in the higher dimension data. Although the interferences were linear, the multi-interference relationships make the prediction system more complex.

For the fluctuation simulation, no matter what the number of data dimensions was, the prediction abilities were impaired gradually by the increase in random noise level. The 'Ion deTech' approach was not able to eliminate the random noise, since no deterministic information could be extracted from the random effects. The higher dimensions there were to the simulation data, the lower was the tolerance that the 'Ion deTech' approach to the fluctuation. It should be emphasized that in a realistic environment, the noise from equipment should be considered. However, it is essential to minimize the noise when sampling data in experiments.

In the modeling of non-linear interference, three exponential degrees of non-linear interference were investigated. The prediction abilities of 'Ion deTech' approach were weakened by increasing the degree of non-linear interference. However, compared to other chemometric methods, the 'Ion deTech' approach offered significantly better prediction capability in various degrees of non-linear interfering situations. It can be concluded that a combination of PCA and ICA is able to extract information to support the system with a modest non-linear interfering data to the Neuron Network for prediction. The higher the data dimension, then the lower prediction accuracy of the 'Ion deTech' approach. This is explained by the higher complexity of the interfering relationships in high dimensional data.

The effects of varying numbers in the training data set have been investigated in the simulation as well. It was found that prediction errors increased dramatically if the training data size resulted in insufficient training information for Artificial Neural Network prediction. On the other hand, after reaching the benchmark size of the training data set, the redundant training data amended the prediction accuracy inefficiently. In addition to enlarging the training size with huge amounts of data, it would make the system more complex and slow down its training speed. To retain high prediction accuracies, when the data dimension is bigger than larger training data sets should be involved. For organizing the training data, using both Orthogonal Experimental Design (OED) and Random Experimental Design (RED) was also investigated. It is evident that with the same numbers of the training data, the data distribution from OED could cover more data volume than RED. Furthermore, the prediction results illustrated that a combination of RED and OED could improve the prediction performance better than when applying random data only.

EXAMPLE 13

Application of the Method and Device to Water Quality Monitoring and Control of Fertigation Systems Referring back to Example 9, further embodiments of the fertigation system were investigated to demonstrate suitability for assessing water quality.

In one embodiment, an array of ion-selective electrodes (ISEs) in the form of an Electronic Tongue (ET) simultaneously determined the multiple free ions for in situ water quality monitoring by measuring the responses from the ISE array in any unknown solution and predicting the concentration directly using the below pattern recognition procedure.

To investigate irrigation water quality, two important indexes are used: 1) Electrical Conductivity (EC), measuring the total soluble salts in the water; and 2) Sodium Adsorption Ration (SAR) which measures the level of sodium relative to calcium and magnesium ions in the water. Inorganic fertilizers are typically composed of three primary macronutrients: nitrogen (as nitrate or ammonium), phosphorus as (phosphate) and potassium. In addition, chlorides are widely distributed in natural waters at various concentrations, together with calcium (Ca) and magnesium (Mg) which are essential elements for determining water hardness. Thus, there are eight important ions which the fertigation system should monitor: ammonium ($NH_4$), calcium (Ca), chloride (Cl), magnesium (Mg), nitrate ($NO_3$), phosphorus (P), potassium (K), and sodium (Na). These ions, which are commonly found in significant concentrations in irrigation waters, are essential for determining water quality and influencing crop yield, soil productivity and environmental contamination. Unfortunately, when using traditional techniques for analysis, the interaction and interference that occur among these elements in environmental samples may severely limit the application of ISEs. However, simultaneous determination of these elements directly using ISE array with appropriate data processing according to the embodiment may offer an alternative technique for developing an intelligent Fertigation system.

To develop this technique, the research was organized into three progressive steps:

Step I—Simultaneous determine four exchangeable cations (calcium, magnesium, sodium and potassium) using an ISE array;

Step II—Increase simultaneous determination capability by including ISE's for three additional elements (ammonia, chloride and nitrate), increasing the prediction system capability to seven elements in total;

Step III—Finally phosphorus was included into the prediction system giving eight elements in total, and real sample were included for system validation (case study)

In the embodiment, the Electronic Tongue (ET) included a suitable water sampling unit that was required to: carry an ISE array; filter the solvents prior to entering the water sampling unit; and transfer water samples through the sampling unit at a defined rate and contact with all ISEs in the array during analysis.

Figure 14:
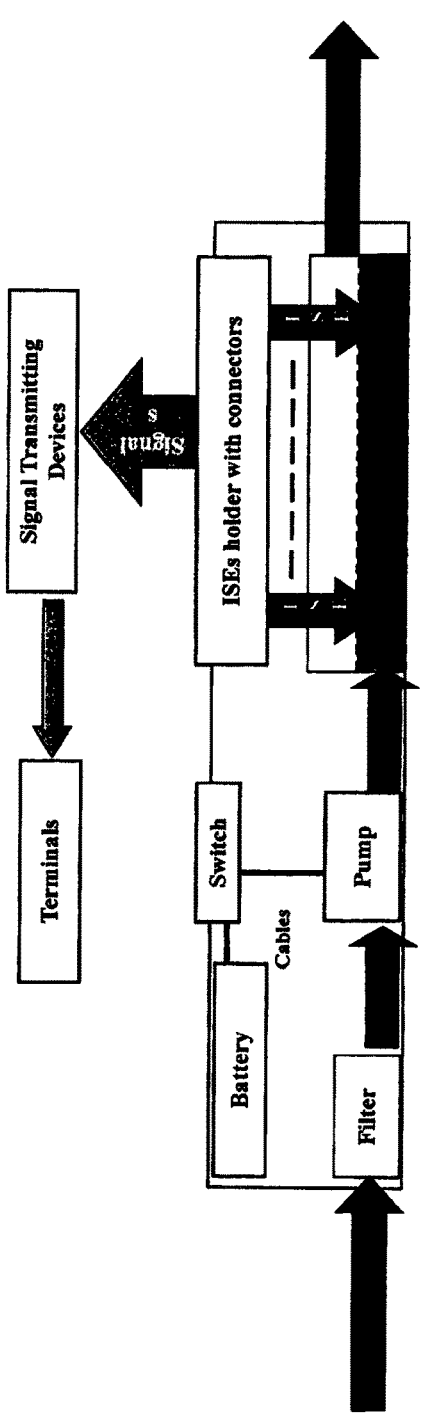
FIG. 14 is a block diagram demonstrating considerations pertaining to a water sampling unit of a fertigation system according to an embodiment of the present invention.

Based on these requirements, a sampling unit was designed as shown in FIG. 14. Initially, sample solutions were pumped into the unit from the inlet tube and passed through the filter into the detecting chamber. Solutions pumped into the chamber were accumulated and maintained at a depth of 30 mm during analysis, using a tap and the level indicator. This solution level was sufficient to submerge and contact the membranes of the ISEs (around 15 mm). It was also possible to assemble and disassemble all sampling unit components including tubing, chamber, pump, filter, probes and holders to allow for cleaning.

With reference to FIG. 14, the water sampling unit was capable of carrying an ISE array consisting of up to 12 individual ISEs. The ISEs were connected directly to the signal amplifiers and to the signal transmitting devices. Furthermore, the water sampling unit contained a filter at the front of the water inlet, one mini electric pump for controlling the flow rate of liquid to the flow-through water sampling unit. A water chamber was used to accumulate and control the water level. For the prototype, the water pump was simply powered by a 12V rechargeable battery. A water-proof container was necessary to protect the battery and signal connectors. A water level indicator was needed to control the pump. The water sampling unit could hold up to 12 ISEs having male TNC connectors (Van London pHoenix Co.).

The components of the system included the following: an inline filter (Whatman 67255002A-01 Inline Filter Solvent IFD Inline Filter Polypropylene Pore Size 0.2 Max Volume 2.5 mL/min); pump (200 Series Peristaltic Pump, Williams, 70 r/min, 12V DC, 1.6 mm Viton tubing); and 12 ISE connectors (Female TNC/Male BNC adapters). Signal transmission cables (RG174A/U) constituted a part of the system, and eight pH amplifiers (Adinstruments Co.) amplified signals and the PowerLab instrument (Adinstruments Co.) was used to interface the computer with the amplifiers. A standard personal computer was employed for system management and signal analysis. Chart 5 software (Adinstruments Co.) was used for data acquisition and filtering. Data processing and analysis was implemented in MatLab 6.5.1 using the Statistical Analysis and Neural Network toolboxes. One Magnetic stirrer (IEC, C876083V) with a spin bar, and several beakers (Schott Duran 250 mL) were employed for samples and standards preparation.

Samples for experiments in the concentration range $10^{-4}$ to $10^{-1}$ M were prepared by diluting and combining appropriate aliquots of 1 M stock solutions of calcium chloride, magnesium chloride, sodium chloride and potassium chloride. Deionized water (Milli Q plus System, Millipore, Bedford, Mass. USA, with 18.2 M$\Omega$ cm$^{-1}$ resistivity) was employed for the preparation of all aqueous solutions. pH in the range of 5.5 to 6.5 was measured using an Orion's pH electrode. This experiment used a 5-ISE array and four chemicals (Table 9). Five commercial electrodes from pHoenix were used in this study: 1) calcium electrode (CAL1501); 2) potassium electrode (KO01501); 3) sodium electrode (NA71501); 4) water hardness electrodes (WHA1501); and 5) An Orion double-junction Ag/AgCl reference electrode (Model 900200). The reference electrode was filled with Orion inner (1M KCl saturated with AgCl) and outer (0.1M $KNO_3$) filling solutions. Since there is no commercial magnesium electrode currently commercially available, the prediction of magnesium was based only on the data relationships in the ISE array.

TABLE 9

Selected chemicals for preparing standard solution of
four selected ions in different concentration ranges

| Chemicals | Range (M) | Ions |
| --- | --- | --- |
| $CaCl_2$ | $10^{-2} \sim 10^{-4}$ | $Ca^{2+}$ |
| KCl | $10^{-2} \sim 10^{-4}$ | $K^+$ |
| NaCl | $10^{-2} \sim 10^{-4}$ | $Na^+$ |
| $MgCl_2$ | $10^{-2} \sim 10^{-4}$ | $Mg^{2+}$ |

Assuming that each chemical had only five different concentrations ranging from $10^{-4}$ to $10^{-2}$M ($1.0 \times 10^{-4}$ M, $0.5 \times 10^{-3}$M, $1.0 \times 10^{-3}$M, $0.5 \times 10^{-2}$M, $1.0 \times 10^{-2}$ M), consider that 4 chemicals and these five concentrations give a total number of combinations equal to $5^4 = 625$ combinations. Consequently, it would be time-consuming to collect data for this number of combinations. Therefore, Orthogonal Experimental Design (OED) was employed to reduce the amount of training samples required without loss of any quality characteristics for the specific ions. Using an Orthogonal Experimental Design of $L_{25}$ ($5^4$), for the four chemicals with five concentrations, the number of required training combinations could be reduced to 25.

Selectivity coefficients found in an analysis of 25 training samples indicate some relationships between ISEs and other undesired ions in solution in Table 10 below. Positive selectivity coefficients (K) indicate that the response of the relevant ISE suffered a positive impact from the interfering ions as concentration increased. A negative selectivity coefficient indicates that the response from the relevant ISE suffered a negative impact from the interfering ions as concentration increased. As shown in the table, there was no severe interference between these ISEs and ions. The most severe interference was the potassium ions on the sodium ISE, which had a selectivity coefficient of 0.07. The ISEs of calcium and water hardness (W. H.) mainly responded to Ca, and the selectivity coefficient of the W. H. ISE was only 0.05 to Mg. Thus, there was no single ISE whose response was based solely on Mg, so that the prediction of Mg was based on the interference relationships from the entire ISE array.

TABLE 10

Experiment I - Selectivity coefficients (K) for the seven ISE's used in the flow-through water sampling prototype array

| Ion | Ion-selective Electrodes | | | |
| --- | --- | --- | --- | --- |
|  | Sodium | Potassium | Water Hardness | Calcium |
| Na | — | −0.01 | −0.05 | −0.04 |
| K | 0.07 | — | −0.01 | −0.01 |
| Mg | 0.06 | −0.01 | 0.05 | −0.04 |
| Ca | −0.02 | −0.02 | 0.94 | — |

In this experiment, geneticICA, implemented fastICA by the Genetic Algorithm, was employed. Principal Component Analysis (PCA) was employed to remove the correlations between data without reducing the data dimensions. Following geneticICA, the covariance between Independent Components (ICs) was reduced to zero. Four ICs was used as the input for the ANN. After optimizing the performance of the Artificial Neural Network (ANN), the architecture of the ANN model was set at 4×20×4 BPNN. It consisted of: one input layer with eight input neurons, and one neuron for each IC; one hidden layer with 20 hidden neurons; one output layer with 4 output neurons, where every output neuron gave the predicted prediction values for the each element studied. The tangent sigmoid transfer function (Tansig) was used as the transfer function for the hidden layer. The linear Purelin transfer function was employed as the output function for the output layer. The weights and biases of the ANN were initialized randomly and the training function was the Bayesian regularization backpropagation training function. The training parameters were set at a maximum of 100 epochs.

Figure 15:
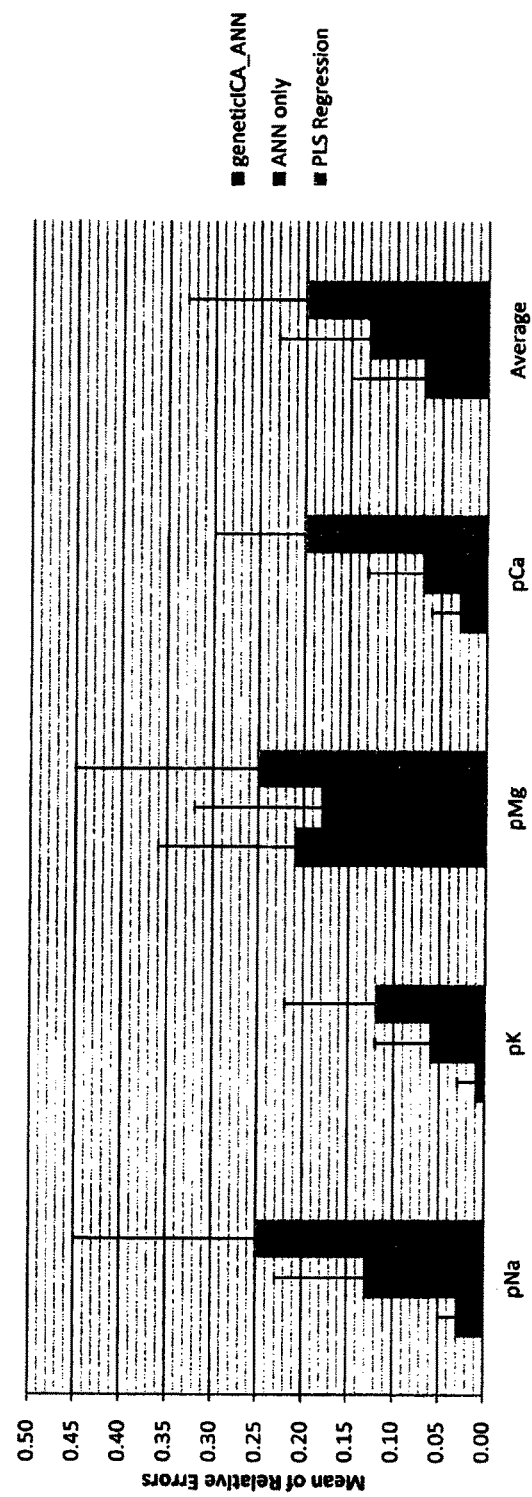
FIG. 15 shows a graph of the prediction errors for an ion selective electrode array according to an embodiment of the present invention.

The robustness and appropriateness of the ANNs was estimated by the Mean of the Relative Error (MRE) of the testing sample set. Since the system was trained in a logarithmic way, logarithmic prediction results of the 20 testing samples were applied to validate the system. As represented in FIG. 15, except for magnesium, the prediction errors for other three ions were ≤0.03 of the MRE. Magnesium was the worst ion predicted with a MRE of 0.21, since no single ISE in the ISE array responded to Mg and the interference relations from entire ISE array could not provide enough information for accurate prediction. The prediction accuracies of the ANN with geneticICA were compared to two other popular quantitative analysis methods commonly used in conjunction with ET systems: firstly, Partial Least Squares (PLS) Regression; and secondly, the Neural Network with no data pre-processing. From a comparison of the Mean of Relative Errors (FIG. 15), the ANN with geneticICA offered the highest prediction accuracies for calcium potassium and sodium. None of these three methods could offer reasonable prediction results for magnesium. The reason is there was not a single ISE whose response was based solely on pMg, and consequently the interference relationships could not offer significant information to aid prediction of pMg.

Samples for orthogonal experiments in the concentration range $10^{-4}$ to $10^{-1}$ M were prepared by diluting and combining 1 M stock solutions of ammonium chloride, calcium chloride, potassium chloride, magnesium chloride, sodium chloride and sodium nitrate. Deionized water (Milli Q plus System, Millipore, Bedford, Mass. USA, with 18.2 MΩ $cm^{-1}$ resistivity) was employed to prepare all aqueous solutions. pH in the range of 5.5 to 6.5 was measured using an Orion's pH electrode. This experiment used an eight-ISE array and six chemicals at seven ion concentrations (Table 11). Three more commercial electrodes from pHoenix were used in this study: 1) ammonium electrode (NH41501); 2) chloride electrode (CL01501); and 3) nitrate electrode (NO31501).

TABLE 11

Selected chemicals for preparing standard solution of
seven selected ions in different concentration ranges

| Chemicals | Range (M) | Ions |
| --- | --- | --- |
| NaCl | $0.1 \sim 10^{-4}$ | $Na^+, Cl^-$ |
| KCl | $10^{-2} \sim 10^{-4}$ | $K^+, Cl^-$ |
| $MgCl_2$ | $10^{-2} \sim 10^{-4}$ | $Mg^{2+}, Cl^-$ |
| $CaCl_2$ | $10^{-2} \sim 10^{-4}$ | $Ca^{2+}, Cl^-$ |
| $NH_4Cl$ | $10^{-2} \sim 10^{-4}$ | $NH_4^+, Cl^-$ |
| $NaNO_3$ | $10^{-2} \sim 10^{-4}$ | $Na^+, NO_3^-$ |

Using an Orthogonal Experimental Design of $L_{49}(7^6)$, for six chemicals with seven concentrations, the number of required training combinations could be reduced to 49. Six chemicals (factors) were chosen: $CaCl_2$, KCl, $MgCl_2$, NaCl, $NaNO_3$ and $NH_4Cl$, where each chemical has seven concentrations. As with experiment in step I, 20 additional samples were used as a testing sample set, by randomly combining ions at various concentrations.

The interferences was evaluated in experiment II using selectivity coefficients, which were determined by analyzing the 49 training samples as shown in FIG. 16. The most severe interference occurred when the potassium ions influenced the ammonium ISE. These potassium ions had a selectivity coefficient of 0.26, meaning that the observed result for ammonium could be doubled if the pK was four times higher than $pNH_4$ due to interference. The ISEs of calcium and water hardness (W. H.) mainly responded to Ca, but the W. H. ISEs were also sensitive to the Mg, with the selectivity coefficient of 0.14. Chloride was the most interfering ion in the group studied, having a selectivity coefficient >0.1 in magnitude for four of the ISEs: ammonium, calcium, nitrate and water hardness (W. H.). Thus there was no single ISE whose response was based solely on pMg so that the prediction of pMg was based on the interference relationships from the entire ISE array.

As mentioned in the experimental step I, Principal Component Analysis (PCA) was employed to remove the correlations between data without reducing the data dimensions. After geneticICA, eight ICs were used as the input for the ANN. After optimizing the performance of the Artificial Neural Network (ANN), the architecture of the ANN model was set at 8×30×7 BPNN. It consisted of: one input layer with eight input neurons, one neuron for each IC; one hidden layer with 30 hidden neurons; and one output layer with seven output neurons, where every output neuron gave the predicted values for each element studied. Other configurations for the ANN were the same as in experiment I.

Figure 17:
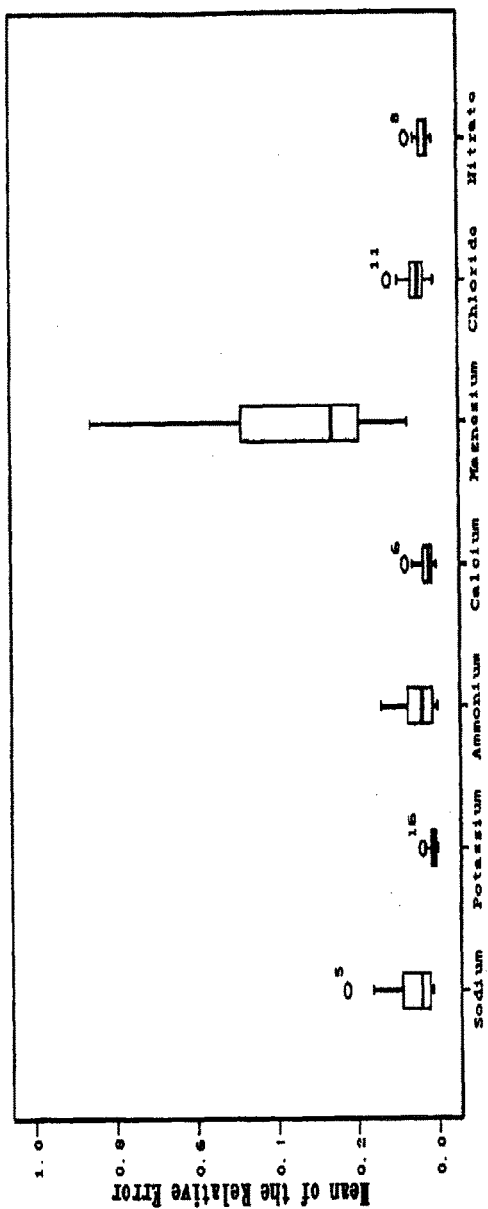
FIG. 17 shows a graph of the prediction errors for an ion selective electrode array according to an embodiment of the present invention.
Figure 18:
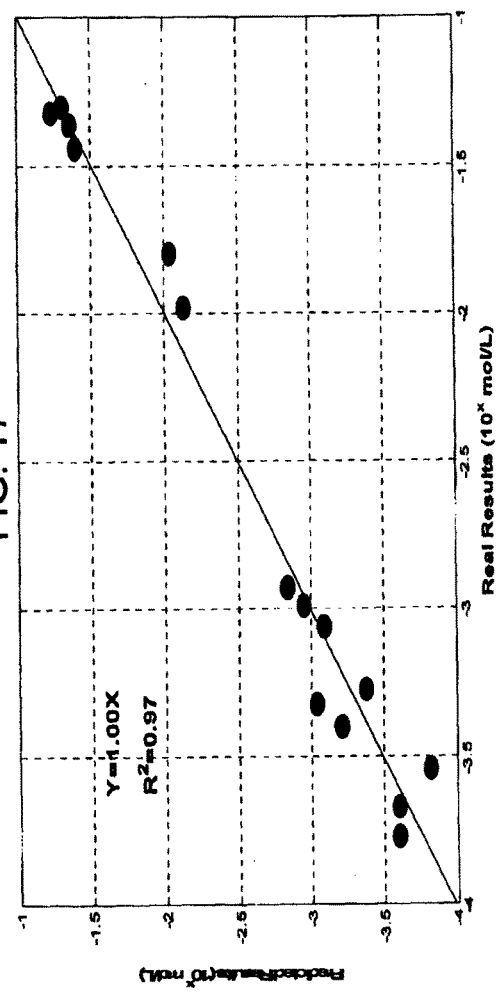
FIG. 18 shows a graph comparing prediction results against actual results according to an embodiment of the present invention.

The robustness and appropriateness of the ANNs, was estimated by the Mean of the Relative Error (MRE) of the testing sample set. Logarithmic prediction results for the 20 testing samples are shown in FIG. 17. The best prediction results were obtained for Ca, K and NO3, with MRE of 0.02, 0.03 and 0.03, respectively. Magnesium was still the worst ion predicted with a MRE of 0.29, since no single ISE in the ISE array responded to Mg and the interference relations from entire ISE array could not provide enough information for accurate prediction. Excluding magnesium, the average prediction precision (MRE) was <0.05.

Based on a comparison of the Mean of Relative Errors with other quantitative analysis methods, it can be concluded that the Neural Network approach with geneticICA offered the highest prediction accuracy of all methods considered. The ANN prediction abilities for each ion were also improved when single PCA or PLS was employed as the data pre-processing step. Partial Least Squares (PLS) regression, afforded the highest prediction accuracy of all the popular linear multivariate regression methods. Generally, however, the ANN methods offered better overall prediction performance than linear multivariate regression methods.

To validate of the system, three real samples was employed. Two of the samples were from Mawson Lakes (SA, Australia), M.L.1 and M.L.2; one was from the River Torrens (SA, Australia). The prediction results were validated using conventional analytical techniques. Cations were determined using ICP-OES and anions (chloride and nitrate) were determined using IC. Samples were analyzed by ICP-OES after a 50-fold dilution, while the samples for IC analysis were diluted 100-fold. Since ammonium is unstable to be stored for a long time, it was not possible to validate this ion. Each sample was measured in triplicate and the average values reported for both ISE-array and ICP/IC. For calcium, potassium, sodium, chloride and nitrate, the prediction capability was lower than 0.06 of the MRE on average. The plots in Figure demonstrate the comparison of predicted results to the determined results via ICP/IC (without NH4 and Mg). FIG. 19 shows a comparison of prediction results from the ISE array with actual results determine via ICP/IC for three real water samples, where concentrations are expressed logarithmically In experiment III, Samples for orthogonal experiments in the concentration range $10^{-4}$ to $10^{-1}$ M were prepared by dilution and combining aliquots of 1 M stock solutions of ammonium chloride, calcium chloride, potassium chloride, magnesium chloride, sodium chloride, sodium nitrate and sodium dihydrogen phosphate respectively. Deionized water (Milli Q plus System, Millipore, Bedford, Mass. USA, with 18.2 M$\Omega$ cm$^{-1}$ resistivity) was employed to prepare all aqueous solutions. The background buffer solution was $10^{-3}$M sodium chloride, in which the pH was adjusted to 3.2 (measured by an Orion's pH electrode) using 3M HAc, to ensure no precipitation of calcium phosphate occurred. All working solutions standards were prepared fresh daily and stored in polyethylene containers. This experiment used a nine-ISE array and seven chemicals at seven ion concentrations (Table 12). Based on the poor results for detecting magnesium in experiment II, instead of using water hardness electrode, which mainly responds to Ca, one electrical conductivity electrode (VanLondon pHoenix Co.) was used instead. The Electrical Conductivity (EC) is a measure of the total soluble salts in the water; and the Sodium Adsorption Ration (SAR) is measure the level of sodium relative to calcium and magnesium ions in the water. Sodium is widely distributed in natural waters at various concentrations, together with calcium (Ca) and magnesium (Mg) which are essential elements for determining water hardness. It should be possible to obtain information on magnesium concentrations from EC and SAR. In this experimental step, one cobalt wire electrode (American Elements: 99.9% basis, Diameter: 2 mm, Length: 8 cm, PN: CO-M_03M_W.080D) was applied as a working electrode into the array. Since the pH value of the background buffer solution was adjusted to 3.2, under such acidic conditions, the dihydrogen phosphate ion ($H_2PO_4^-$) becomes the most common ion in the solution for phosphoric acid. Therefore, the sensor array comprised 8 working electrodes: six ISEs with one EC electrode and one cobalt wire electrode.

TABLE 12

Selected chemicals for preparing standard solution of eight selected ions in different concentration ranges

| Chemicals | Range (M) | Ions |
|---|---|---|
| NaCl | $0.1 \sim 10^{-4}$ | $Na^+, Cl^-$ |
| KCl | $10^{-2} \sim 10^{-4}$ | $K^+, Cl^-$ |
| $MgCl_2$ | $10^{-2} \sim 10^{-4}$ | $Mg^{2+}, Cl^-$ |
| $CaCl_2$ | $10^{-2} \sim 10^{-4}$ | $Ca^{2+}, Cl^-$ |
| $NH_4Cl$ | $10^{-2} \sim 10^{-4}$ | $NH_4^+, Cl^-$ |
| $NaNO_3$ | $10^{-2} \sim 10^{-4}$ | $Na^+, NO_3^-$ |
| $NaH_2PO_4$ | $10^{-2.7} \sim 10^{-4.3}$ | $Na^+, H_2PO_4^-$ |

Using an Orthogonal Experimental Design of $L_{49}(7^7)$, for the seven chemicals with seven concentrations, the number of required training combinations could be reduced to 49. Six chemicals (factors) were chosen: $CaCl_2$, KCl, $MgCl_2$, $NaH_2PO_4$, NaCl, $NaNO_3$ and $NH_4Cl$; with each chemical having seven concentrations. As with Steps I and II, 20 additional samples were used as a testing sample set, by randomly combining ions at various concentrations.

Figure 21:
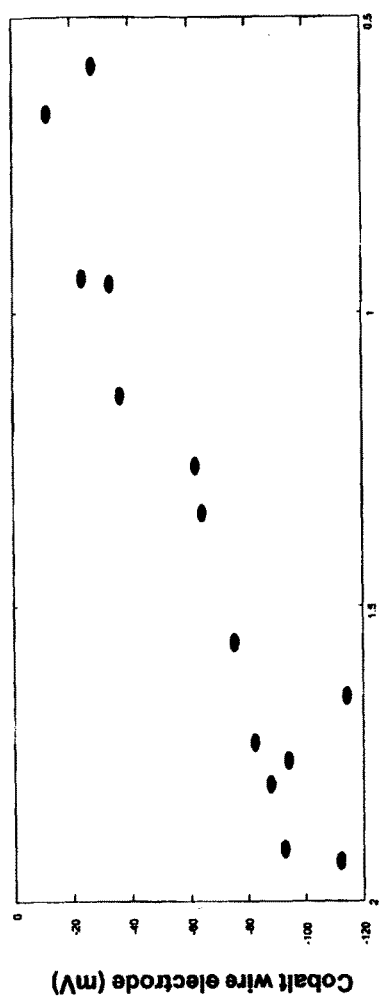
FIG. 21 shows a graph of response values (mV) of a cobalt wire electrode with various levels of pCl interference presented according to an embodiment of the present invention.

The interference was evaluated by selectivity coefficients (K), which were determined from an analysis of the 49 training samples, as shown in FIG. 20. The most severe interference occurred when the chloride ions (K=0.60) influenced the cobalt wire electrode. It is shown in FIG. 21 that the pCl is indicated on the X-axis, and the response values (mV) of the cobalt wire electrode to $pH_2PO_4$=2.7 with various levels of pCl presented are indicated on the Y-axis. Chloride had a severe positive impact on the cobalt wire electrode. The cobalt wire electrode also suffered significant interference from Ca, Mg and Na. All cations (K, Na, $NH_4$) ISEs in the sensor array suffered severe positive impacts from Na, where K=0.39, 0.40 and 0.47 for the potassium, ammonium and calcium ISE, respectively. Severe interference also occurred on the chloride ISE by $[H_2PO_4]^-$ and the nitrate ISE by chloride ions, having the selectivity coefficients of 0.36 and 0.37, respectively. Comparison with the previous two experiments indicated that the ISE array endured more severe interference from undesired ions. This was because, unlike in the previous two experiments, in this third experiment, the training and testing samples were prepared in a background buffer pH adjusted to 3.2, whereas the samples in last two experiments were prepared in deionized water with pH in the range of 5.5 to 6.5. There was again not a single ISE whose response was based solely on Mg and the electrical conductivity electrode had low selectivity for Mg (K<0.05), so that the prediction of Mg was still based on the interference relationships from the entire ISE array.

Figure 22:
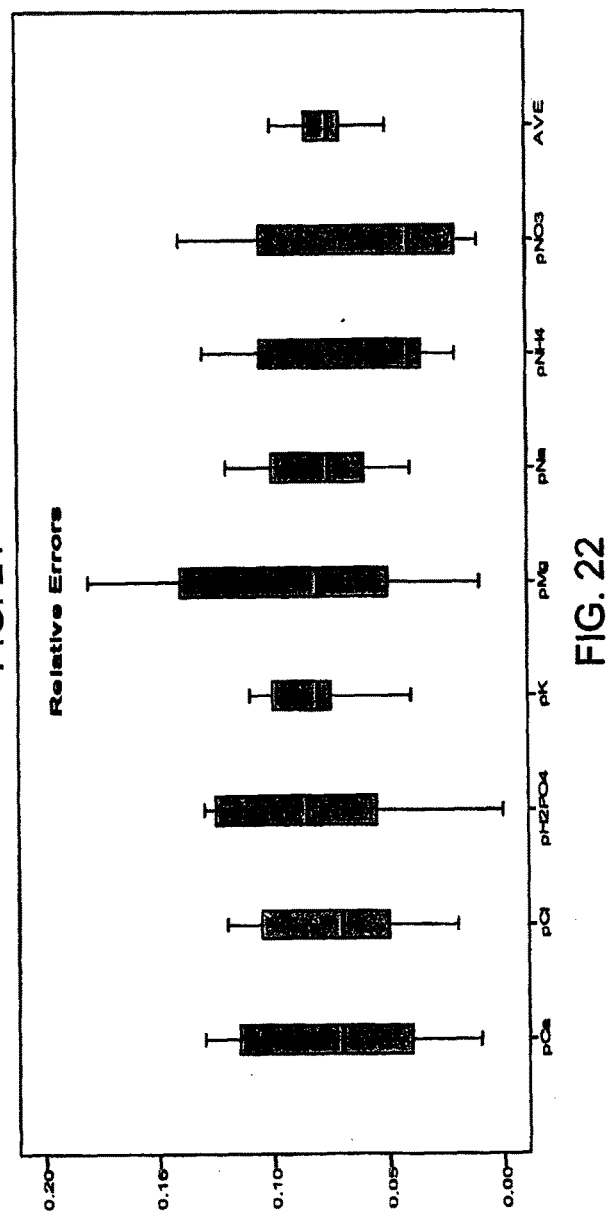
FIG. 22 shows a graph of the prediction errors for an ion selective electrode array according to an embodiment of the present invention.

After PCA and geneticICA, eight ICs were used as the input for the ANN. After optimizing the performance of the Artificial Neural Network (ANN), the architecture of the ANN model was set at 8×30×8 BPNN. It consisted of the following: one input layer with eight input neurons, one neuron for each IC; one hidden layer with 30 hidden neurons; and one output layer with eight output neurons, where every output neuron gave the predicted values for each element studied. Other configurations for the ANN were the same as in the previous experiments. The robustness and appropriateness of the ANNs were estimated by the Mean of Relative Error (MRE) of the testing sample set. Logarithmic prediction results of the 20 testing samples are shown in FIG. 22. The best prediction results were obtained for nitrate with 0.05 of MRE. All the predictions were lower than 0.9 of MRE (0.07 for pCa, 0.07 for pCl, 0.08 for $pH_2PO_4$, 0.09 for pK, 0.07 for $pNH_4$, 0.09 for pNa, and 0.05 for $pNO_3$), without including magnesium. The prediction of magnesium had also been improved with a MRE of 0.12, since the co-relationship from the interference of the entire ISE array (especially from cobalt wire electrode) provided more significant information for accurate prediction. Excluding magnesium, the average prediction precision (MRE) was 0.07.

To validate the system, twenty different real irrigation water samples were collected from five areas within South Australia. The locations and the details of these samples are listed in Table 13. Sampling were collected using standard water sampling procedures. There were five sub-samples (200 mL each), for each individual sample were collected in type bottles ensuring there was no air space in the bottle prior to sealing tightly with screw cap. The samples were delivered to the laboratory and analyzed in 24 hours. During transfer to the laboratory, the samples were covered with ice and kept in a sealed container. The prediction results were validated using conventional analytical techniques. Ca, K, Mg, Na and P were determined using ICP-OES and chloride was determined using IC. Samples were analyzed by ICP-OES after a 10-fold dilution, while the samples for IC analysis were diluted 50-fold. Two bottles of each sample were sent to Australia Laboratory Services (ALS) group (Pooraka, SA) to test for ammonia and nitrate using Discrete Analyser (DA). To testing the real samples by the ISE array, all pH values of the solutions were adjusted to between 3.0 and 3.4 with 3M HAC (measured in triplicate by an Orion's pH electrode). Under such acid condition, the dihydrogen phosphate ion ($H_2PO_4^-$) is the most common phosphate ion present in solution. Therefore, the detection results of phosphorus (P) from ICP-OES were employed to validate the prediction results for $H_2PO_4^-$. Each sample was measured in triplicate by ISE-array and duplicate by the ICP-OES and IC.

TABLE 13

Details of the 20 real irrigation water samples

| No. | Name | Type | Location (South Australia) | pH Before | pH After | Date |
|---|---|---|---|---|---|---|
| 1 | Berri Bore One | Bore | Berri | 6.5 | 3.3 | Dec. 07, 2011 |
| 2 | Berri Bore Two | Bore | Berri | 6.0 | 3.3 | Dec. 07, 2011 |
| 3 | Murry River | River | Berri | 6.1 | 3.1 | Dec. 07, 2011 |
| 4 | Berri C. I. T. Fide | River | Berri | 6.0 | 3.1 | Dec. 07, 2011 |
| 5 | V. I. D. R.1 | Dam | Barossa Valley | 6.4 | 3.4 | Nov. 07, 2011 |
| 6 | V. I. D. R.2 | Dam | Barossa Valley | 6.3 | 3.4 | Nov. 07, 2011 |
| 7 | Barossa Bore | Bore | Barossa Valley | 5.9 | 3.0 | Nov. 07, 2011 |
| 8 | North Para River | River | Barossa Valley | 5.8 | 3.4 | Nov. 07, 2011 |
| 9 | Main Reservoir | Reserved | Barossa Valley | 6.0 | 3.2 | Nov. 07, 2011 |
| 10 | K. R. Large Bore | Bore | McLaren Vale | 5.8 | 3.2 | Oct. 07, 2011 |
| 11 | K. R. Small Bore | Bore | McLaren Vale | 5.8 | 3.2 | Oct. 07, 2011 |
| 12 | R. I. C. C. I | Bore | McLaren Vale | 5.9 | 3.1 | Oct. 07, 2011 |
| 13 | K.R.JOBS | Bore | McLaren Vale | 5.9 | 3.4 | Oct. 07, 2011 |
| 14 | GEMTREE | Bore | McLaren Vale | 6.0 | 3.4 | Oct. 07, 2011 |
| 15 | WOODSIDE DAM 1 | Dam | Woodside | 6.3 | 3.3 | Oct. 07, 2011 |
| 16 | WOODSIDE DAM 2 | Dam | Woodside | 5.8 | 3.2 | Oct. 07, 2011 |
| 17 | MEADOW Over Bore | Bore | Meadows | 5.9 | 3.3 | Oct. 07, 2011 |
| 18 | MEADOW Town Bore | Bore | Meadows | 6 | 3.4 | Oct. 07, 2011 |
| 19 | HAPPY VALLEY | Reserved | Happy Valley | 6.1 | 3.2 | Oct. 07, 2011 |
| 20 | Tap Water | Tap | Mawson Lakes | 5.9 | 3.0 | Oct. 07, 2011 |

Figure 23:
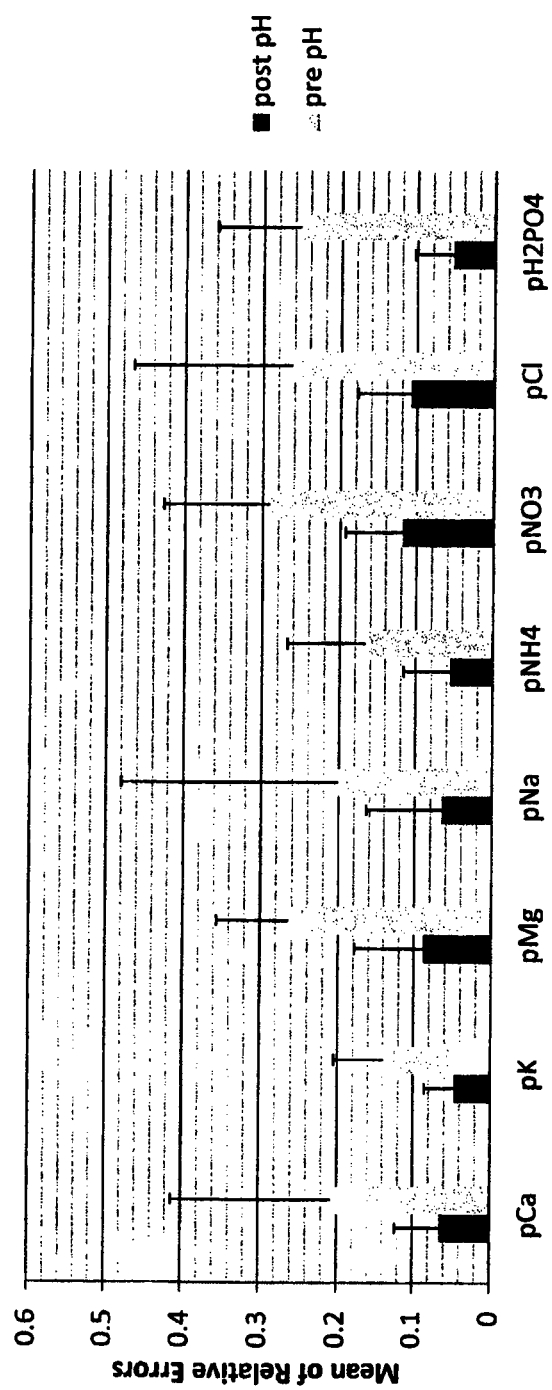
FIG. 23 shows a graph of the means of relative errors for each desired ion according to an embodiment of the present invention.

Comparison of sensor array predicted concentrations with concentrations determined using traditional analytical chemistry methods. The Mean of Relative Errors (MRE) with one standard deviation for each desired ion is shown in FIG. 23. The figure also compared the prediction results of before (pre pH) and after (post pH) adjustment. The sensor array could not accurate predict the analytes without pH adjustment. After the pH of all testing samples was adjusted to pH<3.4, all the predictions were lower than 0.10 of MRE (0.07 for pCa, 0.06 for $pH_2PO_4$, 0.05 for pK, 0.06 for $pNH_4$, 0.09 for Mg, 0.07 for pNa), without including chloride and nitrate, which were 0.11 and 0.12 of MRE, respectively.

Figure 24:
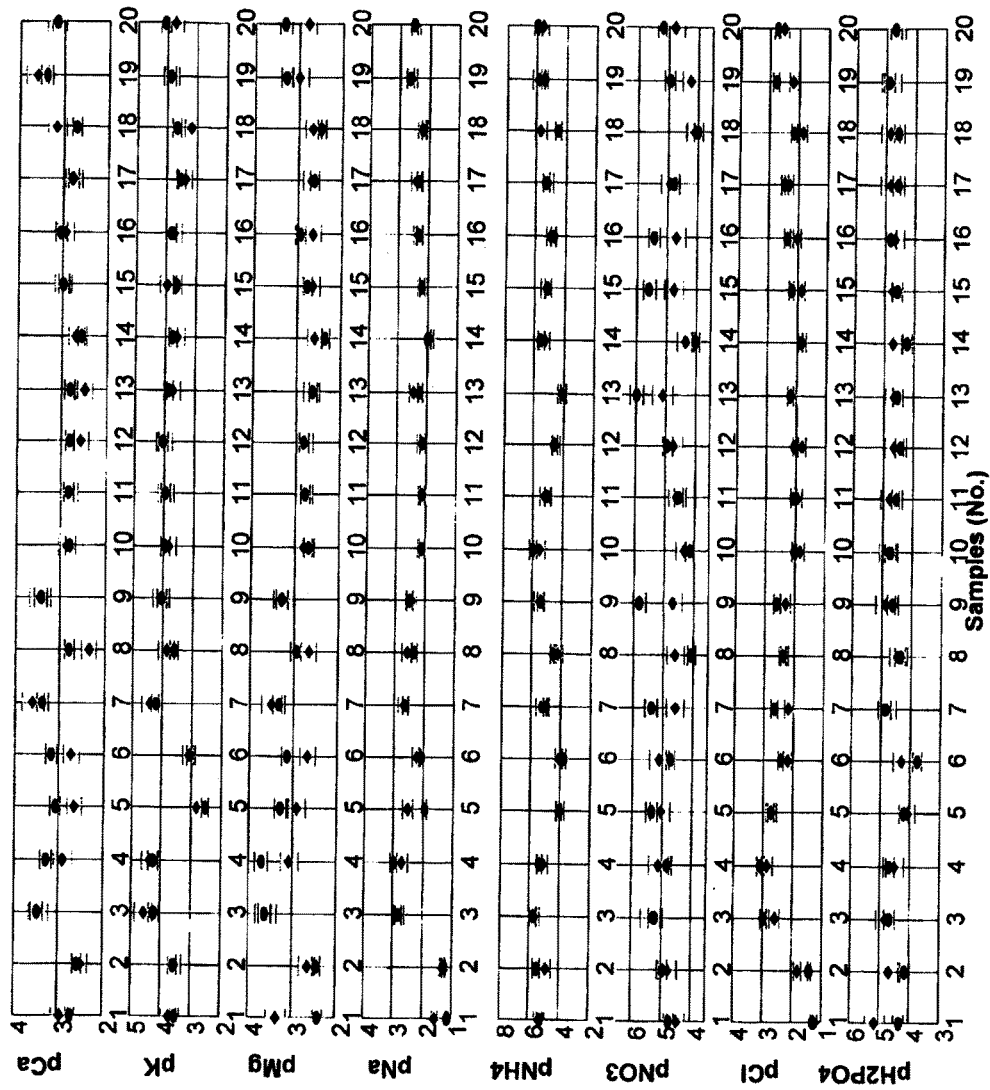
FIG. 24 shows a graph of a comparison of prediction concentrations (shown as a diamond) with determined concentrations from traditional analytical chemistry methods (shown as a circle) for each sample according to an embodiment of the present invention.
Figure 25:
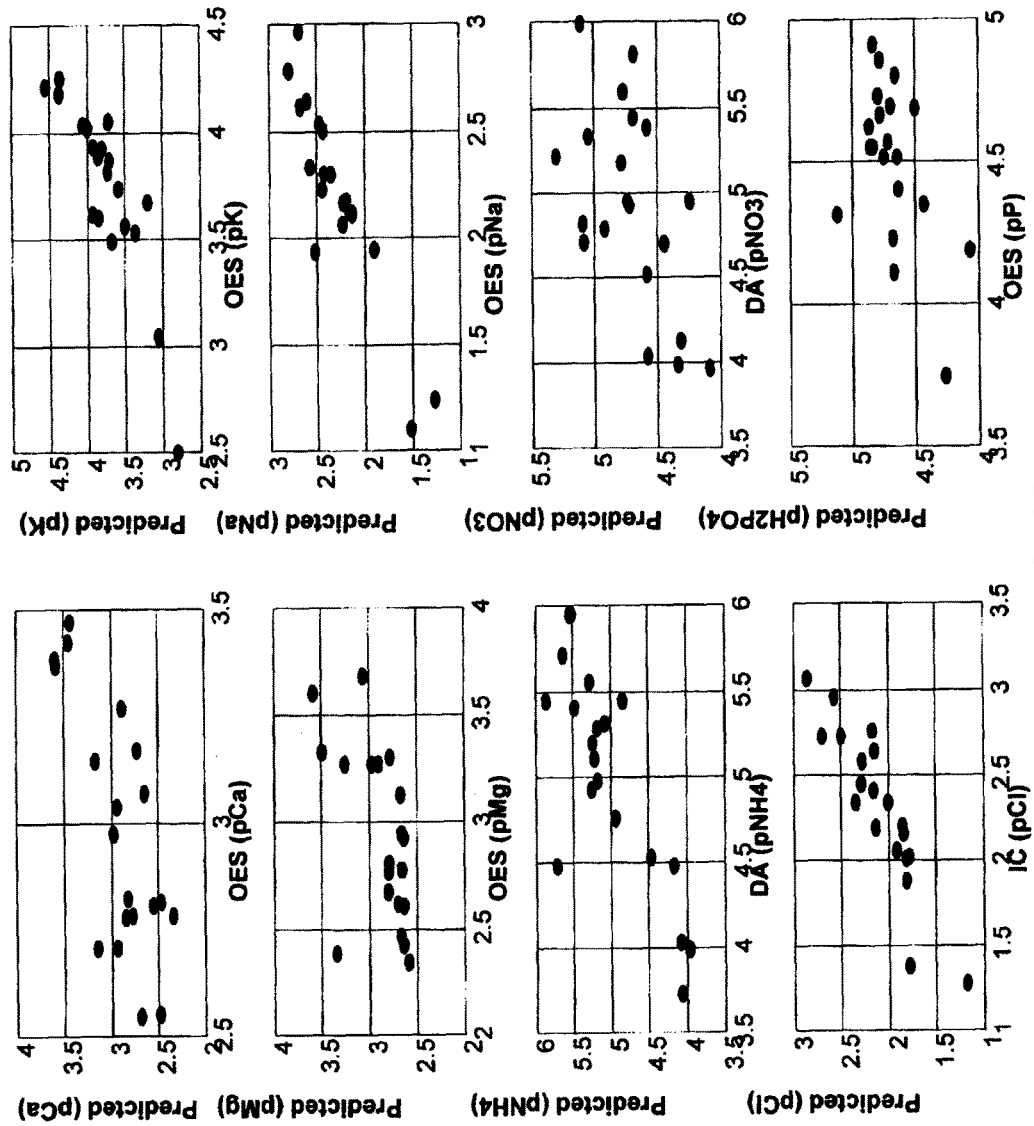
FIG. 25 shows a graph of a comparison of sensor array prediction concentrations with determined concentrations from traditional analytical chemistry methods according to an embodiment of the present invention.

The distributions of prediction errors for each ion are shown in FIGS. 24 and 25. The prediction results for pCl (0.11 of MRE) were generally higher than the results determined by IC (FIG. 24 and FIG. 25). Since the samples for IC were all diluted 50-fold, this would bring some error into accurate IC determination. The concentrations of nitrate for the real testing samples (tested by ALS, using Discrete Analyser) were below the system prediction level of the ISE array (Table 12), which caused large errors, where the prediction accuracy was 0.12 of MRE.

Also as shown in the two errors distribution plots, most phosphate prediction results were lower than the detection results of ICP-OES (0.05 of MRE). This was explained by as dihydrogen phosphate ion ($H_2PO_4^-$) was the most common phosphate species in all the solutions, the cobalt wire electrode responded sensitively to the dihydrogen phosphate ions, and the pP results from ICP-OES corresponded to the total elemental phosphorus concentration in the solution regardless of species, where $pP \geq pH_2PO_4$. Compared to the previous experiments, the prediction accuracy of Mg had improved, since the co-relationship from the interference for the whole ISE array (especially from cobalt wire electrode) provided more significant information for prediction.

To predict the concentration of magnesium, in the first two experiments, the prediction system was not able to offer reasonable prediction results for magnesium, since there was no single ISE in the array, which responded solely to Mg and furthermore, the interference relationships between electrodes could not offer significant information to predict magnesium. In the last experiment, the water hardness electrode was replaced by one electrical conductivity electrode and a cobalt wire electrode. After pH was adjusted, the prediction of magnesium improved, since the co-relationship from the interference of the entire ISE array (especially from cobalt wire electrode) provided more significant information for accurate prediction.

Based on the above, a sensor array consisting of 8 working electrodes—six ISEs with one EC electrode and one cobalt wire electrode—could detect dihydrogen phosphate ions. Following the experiments, all the essential macro-elements common in irrigation water, including Ca, Cl, H2PO4, K, Mg, Na, NH4 and NO3 were simultaneously determined with reasonable accuracy. The prediction abilities were successfully validated using twenty different real irrigation water samples, collected from five different locations in South Australia.

EXAMPLE 14

Application of the Method and Device to Water Quality Monitoring and Control of Fertigation Systems Further to Example 12, one hundred different real water samples were collected and tested using the same methodology, which includes: soil leaching (36 samples), bore water (48 samples) and surface water (17 samples). The details of these samples are listed in table 14 below. Thirty six validation samples were soil leaching from different soils. For soil leaching, 200 g of each soil sample was contained in a PVC pipe. A filter fabric was put into the bottom of each PVC pipe. Deionized water was parallel pumping into three different soil samples by a peristaltic pump. Flow rate of the pump was adjusted based on different soil characteristics. There were 62 different real irrigation water samples were collected from New South Wales and South Australia. The water samples were including: bore water, river water, dam water, reverse osmotic water and tap water. The water samples were collected using standard water sampling procedures. There were two sub-samples (200 mL each), for each individual sample were collected in type bottles ensuring there was no air space in the bottle prior to sealing tightly with screw cap. The samples were delivered to the laboratory and analysed in 24 hours. During transfer to the laboratory, the samples were covered with ice and kept in a sealed container.

TABLE 14

Details of the 100 real irrigation water samples

| No. | Name | Type | Location | pH | Date |
|---|---|---|---|---|---|
| 1 | RBT | Soil leaching | Redland Bay, QLD | 5.0 | 5 Nov. 2011 |
| 2 | WRT | Soil leaching | Wallaroo, SA | 3.8 | 5 Nov. 2011 |
| 3 | FRT | Soil leaching | Flat Rock, NSW | 5.0 | 5 Nov. 2011 |
| 4 | PBT | Soil leaching | Port Broughton, SA | 5.4 | 5 Nov. 2011 |
| 5 | ATB | Soil leaching | Athenhen QLD | 5.9 | 5 Nov. 2011 |
| 6 | PW | Soil leaching | Pitts water, QLD | 5.3 | 5 Nov. 2011 |
| 7 | UCT | Soil leaching | Uppercomma, QLD | 5.5 | 5 Nov. 2011 |
| 8 | TE03T | Soil leaching | Tavern, NSW | 5.4 | 5 Nov. 2011 |
| 9 | MLT | Soil leaching | Mawson Lakes, SA | 4.7 | 5 Nov. 2011 |
| 10 | BIT | Soil leaching | Bribie Island, QLD | 4.7 | 5 Nov. 2011 |
| 11 | RHB | Soil leaching | Richmond, NSW | 4.8 | 5 Nov. 2011 |
| 12 | RHT | Soil leaching | Richmond, NSW | 4.6 | 5 Nov. 2011 |
| 13 | RBB | Soil leaching | Redland Bay, QLD | 4.9 | 5 Nov. 2011 |
| 14 | Plot 1 Control | Soil leaching | St Kilda, SA | 4.9 | 5 Nov. 2011 |
| 15 | Plot 2 B.J.O | Soil leaching | St Kilda, SA | 4.7 | 5 Nov. 2011 |
| 16 | Plot 1/25 | Soil leaching | St Kilda, SA | 5.1 | 5 Nov. 2011 |
| 17 | Plot 2 Control | Soil leaching | St Kilda, SA | 4.9 | 5 Nov. 2011 |
| 18 | Plot 2/B50 | Soil leaching | St Kilda, SA | 5.2 | 5 Nov. 2011 |
| 19 | Plot 2/B25 | Soil leaching | St Kilda, SA | 5.2 | 6 Nov. 2011 |
| 20 | Plot 2/C50 | Soil leaching | St Kilda, SA | 5.5 | 6 Nov. 2011 |
| 21 | Plot 2 B/C | Soil leaching | St Kilda, SA | 5.2 | 6 Nov. 2011 |
| 22 | Plot 2/C25 | Soil leaching | St Kilda, SA | 5.6 | 6 Nov. 2011 |
| 23 | BNB | Soil leaching | QLD | 6.4 | 6 Nov. 2011 |

TABLE 14-continued

Details of the 100 real irrigation water samples

| No. | Name | Type | Location | pH | Date |
|---|---|---|---|---|---|
| 24 | BNA | Soil leaching | QLD | 5.9 | 6 Nov. 2011 |
| 25 | STB | Soil leaching | QLD | 6.2 | 6 Nov. 2011 |
| 26 | STA | Soil leaching | QLD | 5.8 | 6 Nov. 2011 |
| 27 | MTB | Soil leaching | QLD | 5.8 | 6 Nov. 2011 |
| 28 | MTA | Soil leaching | QLD | 5.4 | 6 Nov. 2011 |
| 29 | G/A | Soil leaching | QLD | 5.7 | 6 Nov. 2011 |
| 30 | BBA | Soil leaching | QLD | 6.1 | 6 Nov. 2011 |
| 31 | BBB | Soil leaching | QLD | 5.9 | 4 Nov. 2011 |
| 32 | IWA | Soil leaching | QLD | 5.6 | 4 Nov. 2011 |
| 33 | SGA | Soil leaching | QLD | 5.7 | 4 Nov. 2011 |
| 34 | IWB | Soil leaching | QLD | 5.8 | 4 Nov. 2011 |
| 35 | TXA | Soil leaching | QLD | 5.8 | 4 Nov. 2011 |
| 36 | BDA | Soil leaching | QLD | 5.7 | 4 Nov. 2011 |
| 37 | M1 | BORE | Meadows, SA | 4.8 | 14 Nov. 2011 |
| 38 | M2 | R.O. | Meadows, SA | 6.4 | 14 Nov. 2011 |
| 39 | M3 | BORE + R.O. | Meadows, SA | 6.0 | 14 Nov. 2011 |
| 40 | M4 | Fertilized | Meadows, SA | 4.1 | 14 Nov. 2011 |
| 41 | M5 | Feeding Water | Meadows, SA | 5.2 | 14 Nov. 2011 |
| 42 | M6 | Fertilized | Meadows, SA | 5.3 | 14 Nov. 2011 |
| 43 | M7 | Dam | Meadows, SA | 6.1 | 14 Nov. 2011 |
| 44 | M8 | Dam | Meadows, SA | 6.0 | 14 Nov. 2011 |
| 45 | M9 | Dam | Meadows, SA | 6.2 | 14 Nov. 2011 |
| 46 | M10 | Dam | Meadows, SA | 6.2 | 14 Nov. 2011 |
| 47 | B108 | Bore | Williamstown, NSW | 5.0 | 8 Nov. 2011 |
| 48 | B5 | Bore | Williamstown, NSW | 4.9 | 8 Nov. 2011 |
| 49 | B8 | Bore | Williamstown, NSW | 5.0 | 8 Nov. 2011 |
| 50 | FF2SS14 | Bore | Williamstown, NSW | 4.2 | 8 Nov. 2011 |
| 51 | FF2SS07 | Bore | Williamstown, NSW | 5.9 | 8 Nov. 2011 |
| 52 | W18 | Bore | Williamstown, NSW | 5.3 | 8 Nov. 2011 |
| 53 | WL107 | Bore | Williamstown, NSW | 5.5 | 8 Nov. 2011 |
| 54 | WL109 | Bore | Williamstown, NSW | 5.4 | 8 Nov. 2011 |
| 55 | WL111 | Bore | Williamstown, NSW | 5.9 | 8 Nov. 2011 |
| 56 | WL201 | Bore | Williamstown, NSW | 5.7 | 8 Nov. 2011 |
| 57 | WL202 | Bore | Williamstown, NSW | 4.9 | 8 Nov. 2011 |
| 58 | WL203 | Bore | Williamstown, NSW | 5.5 | 8 Nov. 2011 |
| 59 | WL205 | Bore | Williamstown, NSW | 5.3 | 8 Nov. 2011 |
| 60 | WL207 | Bore | Williamstown, NSW | 5.4 | 8 Nov. 2011 |
| 61 | WL209 | Bore | Williamstown, NSW | 5.1 | 8 Nov. 2011 |
| 62 | WL210 | Bore | Williamstown, NSW | 5.4 | 8 Nov. 2011 |
| 63 | WL211 | Bore | Williamstown, NSW | 5.9 | 8 Nov. 2011 |
| 64 | WL215 | Bore | Williamstown, NSW | 5.0 | 8 Nov. 2011 |
| 65 | L1 | Tap | Mawson Lakes, SA | 5.4 | 18 Nov. 2011 |
| 66 | L2 | Filter water | Mawson Lakes, SA | 5.6 | 18 Nov. 2011 |
| 67 | L3 | Bore | Adelaide, SA | 6.5 | 18 Nov. 2011 |
| 68 | L4 | Lakes | Mawson Lakes, SA | 6.5 | 18 Nov. 2011 |
| 69 | L5 | Filter water | Adelaide, SA | 6.9 | 18 Nov. 2011 |
| 70 | Orlando I | Bore | Barossa Valley, SA | 5.9 | 16 Nov. 2011 |
| 71 | Orlando II | Bore | Barossa Valley, SA | 6.3 | 16 Nov. 2011 |
| 72 | Orlando Dam | Dam | Barossa Valley, SA | 6.5 | 16 Nov. 2011 |
| 73 | Hahn Ebenezer | Bore | Barossa Valley, SA | 6.3 | 16 Nov. 2011 |
| 74 | Hahn Dam | Dam | Barossa Valley, SA | 6.6 | 16 Nov. 2011 |
| 75 | Hahn Pass | Bore | Barossa Valley, SA | 6.5 | 16 Nov. 2011 |
| 76 | Hahn Creek | Creek | Barossa Valley, SA | 6.5 | 16 Nov. 2011 |
| 77 | Stuart's Bore | Bore | Barossa Valley, SA | 6.2 | 16 Nov. 2011 |
| 78 | John's Bore | Bore | Barossa Valley, SA | 6.0 | 16 Nov. 2011 |
| 79 | Beer Brothers I | Bore | Barossa Valley, SA | 6.3 | 16 Nov. 2011 |
| 80 | Beer Brothers II | Bore | Barossa Valley, SA | 6.3 | 16 Nov. 2011 |
| 81 | Beer Brothers III | Bore | Barossa Valley, SA | 6.2 | 16 Nov. 2011 |
| 82 | Lindsay Bore I | Bore | Barossa Valley, SA | 6.5 | 16 Nov. 2011 |
| 83 | Lindsay Bore II | Bore | Barossa Valley, SA | 6.4 | 16 Nov. 2011 |
| 84 | Berri Bore One | Bore | Berri, SA | 6.5 | 12 Nov. 2011 |
| 85 | Berri Bore Two | Bore | Berri, SA | 6.0 | 12 Nov. 2011 |
| 86 | Murry River | River | Berri, SA | 6.1 | 12 Nov. 2011 |
| 87 | Berri C. I. T. Fide | River | Berri, SA | 6.0 | 12 Nov. 2011 |
| 88 | V. I. D. R.1 | Dam | Barossa Valley, SA | 6.4 | 11 Nov. 2011 |
| 89 | V. I. D. R.2 | Dam | Barossa Valley, SA | 6.3 | 11 Nov. 2011 |
| 90 | Barossa Bore | Bore | Barossa Valley, SA | 5.9 | 11 Nov. 2011 |
| 91 | North Para River | River | Barossa Valley, SA | 5.8 | 11 Nov. 2011 |
| 92 | Main Reservoir | Reserved | Barossa Valley, SA | 6.0 | 11 Nov. 2011 |
| 93 | K. R. I | Bore | McLaren Vale, SA | 5.8 | 10 Nov. 2011 |
| 94 | K. R. II | Bore | McLaren Vale, SA | 5.8 | 10 Nov. 2011 |
| 95 | R. I. C. C. I | Bore | McLaren Vale, SA | 5.9 | 10 Nov. 2011 |
| 96 | K.R.JOBS | Bore | McLaren Vale, SA | 5.9 | 10 Nov. 2011 |
| 97 | GEMTREE | Bore | McLaren Vale, SA | 6.0 | 10 Nov. 2011 |
| 98 | Woodside DAM 1 | Dam | Woodside, SA | 6.3 | 10 Nov. 2011 |
| 99 | Woodside DAM 2 | Dam | Woodside, SA | 5.8 | 10 Jul. 2011 |

TABLE 14-continued

Details of the 100 real irrigation water samples

| No. | Name | Type | Location | pH | Date |
|---|---|---|---|---|---|
| 100 | Meadows I | Bore | Meadows, SA | 5.9 | 10 Jul. 2011 |
| 101 | Meadows II | Bore | Meadows, SA | 6 | 10 Jul. 2011 |
| 102 | Happy Valley | Reserved | Happy Valley, SA | 6.1 | 10 Jul. 2011 |

The system used to test the above samples comprised a nine electrode array: Seven commercial electrodes from pHoenix were used in this study: 1) ammonium electrode (NH41501) 2) calcium electrode (CAL1501); 3) chloride electrode (CL01501); 4) nitrate electrode (NO31501); 5) potassium electrode (KO01501); 6) sodium electrode (NA71501); 7) EC electrode; One C-CIT AG (Switzerland) magnesium electrode and an Orion double junction Ag/AgCl reference electrode (Model 900200) and. The reference electrode was filled with Orion inner (1M KCl saturated with AgCl) and outer (0.1M KNO3) filling solutions. Eight pH amplifiers (Adinstruments Co.) amplified signals and the PowerLab instrument (Adinstruments Co.) were used to interface the computer with the amplifiers. A standard personal computer was employed for system management and signal analysis. Chart 5 software (Adinstruments Co.) was used for data acquisition and filtering. Data processing and analysis was implemented in MatLab 6.5.1 using the Statistical Analysis and Neural Network toolboxes. One Magnetic stirrer (IEC, C876083V) with a spin bar, and several beakers (Schott Duran 250 mL) were employed for samples and standards preparation.

Samples for training the neural network system were in the concentration range $10^{-4}$ to $10^{-1}$ M were prepared by diluting and combining appropriate aliquots of 1 M stock solutions of ammonium chloride, calcium chloride, potassium chloride, magnesium chloride, sodium chloride and sodium nitrate. Deionized water (Milli Q plus System, Millipore, Bedford, Mass. USA, with 18.2 MΩ cm$^{-1}$ resistivity) was employed to prepare all aqueous solutions. pH in the range of 5.5 to 6.5 was measured using an Orion's pH electrode. The six chemicals at seven ion concentrations are showing in Table 15.

TABLE 15

Selected chemicals for preparing standard solution of seven selected ions in different concentration ranges

| Chemicals | Range (M) | Ions |
|---|---|---|
| NaCl | $0.1\sim10^{-4}$ | Na$^+$, Cl$^-$ |
| KCl | $10^{-2}\sim10^{-4}$ | K$^+$, Cl$^-$ |
| MgCl$_2$ | $10^{-2}\sim10^{-4}$ | Mg$^{2+}$, Cl$^-$ |
| CaCl$_2$ | $10^{-2}\sim10^{-4}$ | Ca$^{2+}$, Cl$^-$ |
| NH$_4$Cl | $10^{-2}\sim10^{-4}$ | NH$_4^+$, Cl$^-$ |
| NaNO$_3$ | $10^{-2}\sim10^{-4}$ | Na$^+$, NO$_3^-$ |

Using an Orthogonal Experimental Design of $L_{49}(7^6)$, for six chemicals with seven concentrations, the number of required training combinations could be reduced to 49. Six chemicals (factors) were chosen: CaCl$_2$, KCl, MgCl$_2$, NaCl, NaNO$_3$ and NH$_4$Cl, where each chemical has seven concentrations.

All measurements were carried out at the same temperature in triplicate. Each solution (150 mL) was measured in 250 mL beakers. All samples were stirred gently during measurement. A heat insulation pad was employed to prevent temperature changes during stirring. Electrode tips were immersed into the solution and positioned about halfway between the center of the beaker and the beaker wall. Between measurements, the electrodes were always rinsed with MQ water and blotted dry on tissue paper to remove any absorbed species, in order to prevent electrode cross-contamination. During measurement, electrode membranes were completely free from air bubbles after immersion into the analysis solution. For each individual measurement, a set of single meter readings for each ISE were recorded while the readings were relatively stable, i.e. at a constant potential of ±0.05 mV, over 2-3 mins. Single point calibrations with standard solutions ($10^{-3}$M Cu and $10^{-3}$M Cl), were carried out every hour.

The interferences were evaluated using selectivity coefficients, which were determined by analyzing the 49 training samples (Table 16). The most severe interference occurred when the sodium ions influenced the magnesium ISE. These sodium ions had a selectivity coefficient of 0.27, meaning that the observed result for magnesium could be doubled if the pNa was four times higher than pMg due to interference. Chloride was the most interfering ion in the group studied, having a selectivity coefficient >0.1 in magnitude for four of the ISEs: calcium, potassium, magnesium and nitrate; and nitrate ISE suffered the most interference in the group studied, excepted sodium, all observed ions offered the interference >0.1 of selectivity coefficient.

TABLE 16

Selectivity coefficients (K) for the ISEs

| ISE | pNa | pK | pCa | pMg | pNH$_4$ | pCl | pNO$_3$ |
|---|---|---|---|---|---|---|---|
| Sodium | — | −0.05 | −0.02 | −0.06 | 0.04 | −0.09 | 0.06 |
| Potassium | −0.19 | — | −0.02 | 0.01 | 0.03 | −0.16 | −0.06 |
| Calcium | −0.23 | −0.01 | — | −0.05 | 0.07 | −0.14 | 0.12 |
| Magnesium | −0.27 | −0.17 | −0.10 | — | 0.09 | −0.15 | 0.02 |
| Ammonium | −0.13 | −0.10 | −0.13 | 0.02 | — | −0.15 | 0.02 |
| Chloride | 0.05 | 0.07 | 0.09 | 0.06 | 0.14 | — | −0.18 |
| Nitrate | −0.09 | 0.13 | 0.13 | 0.12 | 0.17 | −0.18 | — |

As described, Principal Component Analysis (PCA) was employed to remove the correlations between data without reducing the data dimensions. After geneticICA, eight ICs were used as the input for the ANN. After optimizing the performance of the Artificial Neural Network (ANN), the architecture of the ANN model was set at 8×30×7 BPNN. It consisted of: one input layer with eight input neurons, one neuron for each IC; one hidden layer with 30 hidden neurons; and one output layer with seven output neurons, where every output neuron gave the predicted values for each element studied. Other configurations for the ANN were the same as above.

The prediction results were validated using conventional analytical techniques. Ca, K, Mg, Na were determined using ICP-OES, chloride and nitrate were determined using IC. Samples were analysed by ICP-OES after a 10-fold dilution, while the samples for IC analysis were diluted 20-fold. Two bottles of each sample were sent to Australia Laboratory Services (ALS) group (Pooraka, S A) to test for ammonium using Discrete Analyser (DA). Each sample was measured in triplicate by ISE-array and duplicate by the ICP-OES and IC. Since the lowest detect limit of ISE array was trained to be $10^{-4}$ M for each observed ion. It was defined that for both prediction and analysed results from ISE array and conventional analytical techniques, any ion concentration, which was detected below $10^{-4}$ M, was set to be $10^{-4.02}$.

Comparison of sensor array predicted concentrations with concentrations determined using traditional analytical chemistry methods are shown from FIG. 4 to FIG. 6. The prediction errors were calculated by the Mean of Relative Errors (MRE) for each desired ion. The MRE results excluded the samples, with the prediction or analysing results below $10^{-4}$M.

Figure 26:
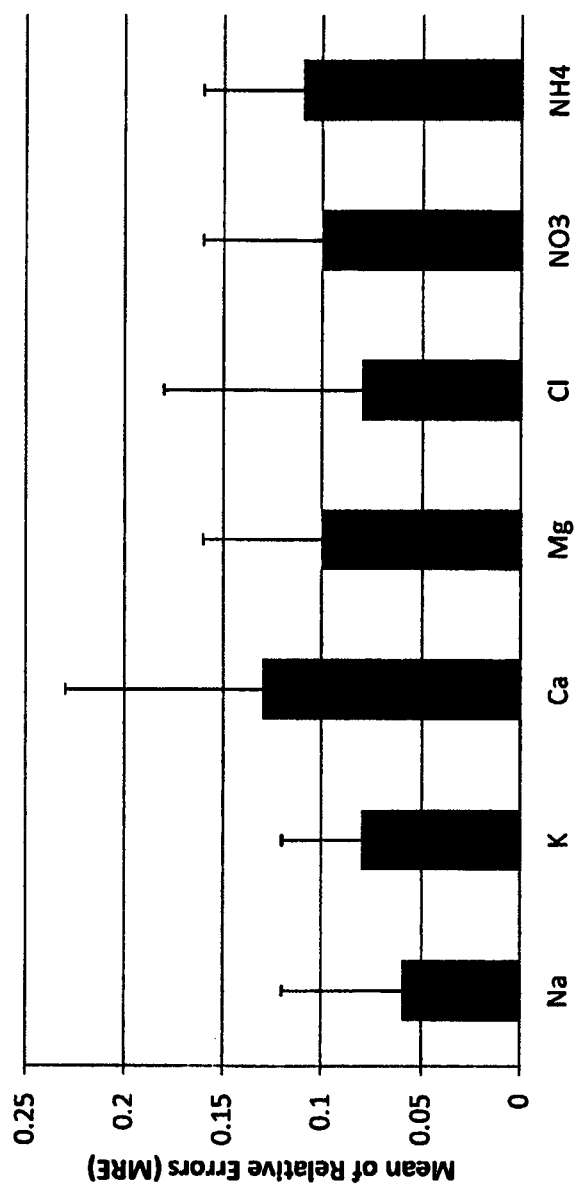
FIG. 26 shows a graph of the means of relative errors for each desired ion according to an embodiment of the present invention.
Figure 27:
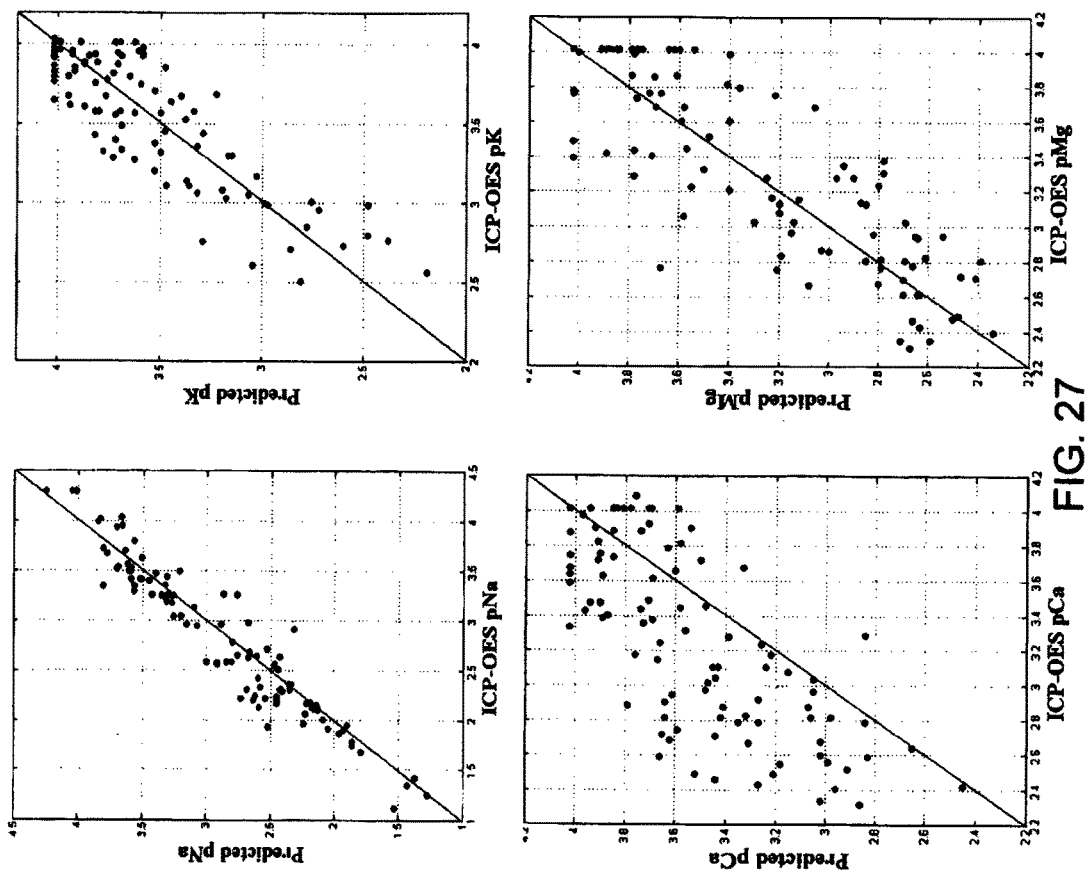
FIG. 27 shows a graph of a comparison of prediction results with actual results determined via ICP-OES in logarithmic values according to an embodiment of the present invention.
Figure 28:
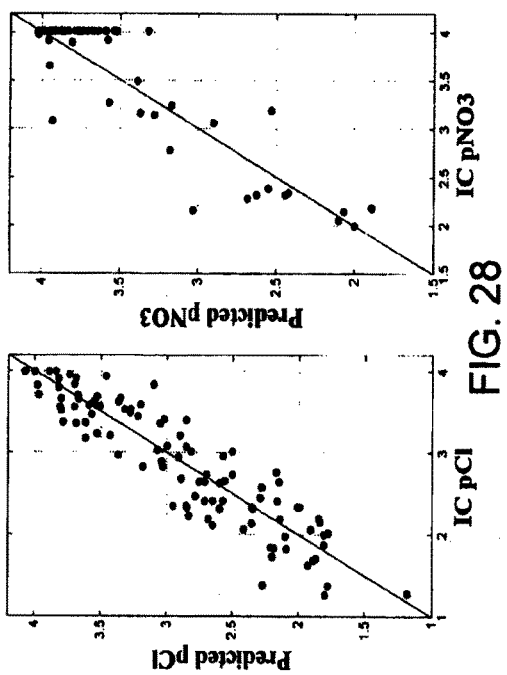
FIG. 28 shows a graph of a comparison of prediction results with actual results determined via IC in logarithmic values according to an embodiment of the present invention.
Figure 29:
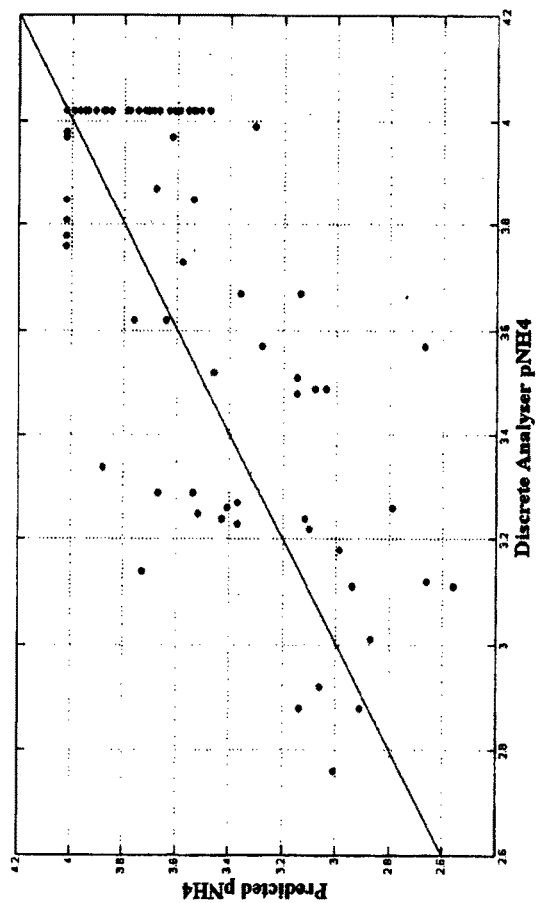
FIG. 29 shows a graph of a comparison of ammonium prediction results with actual results determined via Discrete Analyzer in logarithmic values according to an embodiment of the present invention.

As shown in FIG. 26, the best prediction belongs to sodium, which the prediction error was 0.06 of MRE. Most of the prediction accuracies were below 0.1 of MRE (0.08 for chloride, 0.08 for potassium, 0.10 for nitrate), excluding ammonium, calcium and magnesium, which were 0.12, 0.13 and 0.11 of MRE, respectively. Furthermore, from FIG. 27 to FIG. 29, it is interesting that the concentrations of sodium and chloride were higher in the real water samples than in the soil leaching samples. Whereas, nitrate was widely contained in soil leaching samples rather than real water samples, excluding three water samples from Meadows (M4, M5, M6), which contained high concentration of nitrate. The reason was these three samples were fertilized water with calcium nitrate and magnesium nitrate. It can be concluded that all the real water samples were not contaminated by nitrate. The prediction abilities of ammonium, nitrate and magnesium were not as strong as chloride, potassium and sodium, which because the magnesium ISE was seriously interfered by sodium, chloride and potassium; Nitrate and ammonium ISE were significantly interfered by all observed ions (Table 16). Most of the calcium predictions were lower than the ICP-OES. The results from ICP-OES corresponded to the total elemental calcium concentration in the solution regardless of species, while the calcium ion-selective electrode is measuring the free calcium ions in the solution.

SUMMARY

As described, Electronic Tongue (ET) systems incorporating various pattern recognition techniques have being studied for both qualitative and quantitative analysis. In each described ET system, there is a sensor array composed of different types of working and reference electrodes. The different working electrodes, may record either potential or current differences between the reference electrode and each working electrode, which can be used as input data for pattern recognition. For successful application of an electronic tongue system, choosing the most appropriate method of recognition is crucial.

In this research, an ET system was developed and the application was based on processing the response signals from an array of ion-selective electrodes and the detection results could be gained rapidly and accurately. This system has the advantage of rapid real time response, portability and low cost, which indicated that the system could comprehensively be applied to online in situ water quality assessments. This technique was able to minimize the interference between undesired ions and ion-selective electrodes, as well as the co-relationships among ion-selective electrodes. For the proposed pattern recognition method, Artificial Neural Network (ANN) algorithms were employed to simultaneously determine elemental concentrations. A signal processing method, Independent Component Analysis (ICA) was considered as a data preprocessing method for extracting the features for mixed chemicals and Principal Component Analysis (PCA) was used as the preferred signal whitening method.

The prediction capability of the above method was tested by modeling data. In the first modeling section, data starting from simply two dimensions to the more complicated eight dimensions scenario, which has been comprehensively simulated. The modeling was focused on simulating the potential response values from an array of ion-selective electrodes in an Electronic Tongue (ET) system to predict the concentrations of target ions. The simulation included testing both linear and non-linear interferences of different degrees; various numbers of training data and noises from both system and measuring errors. Based on the improvements emanating from Principal Component Analysis, Independent Component Analysis (ICA) can extract further information from the raw data and which improved the prediction ability of the Artificial Neural Networks. The prediction performance of the above method was slightly impaired by increasing data dimensions, so that the higher data dimensions needed a larger training data for training the pattern recognition system. Building on this theme, for organizing the training data, both Orthogonal Experimental Design (OED) and Random Experimental Design (RED) were analyzed. It was evident that with the same number of training data, the data construction from OED was able to cover a larger data area than RED, and the prediction results indicated that a combination of RED and OED could improve prediction accuracy.

Independent Component Analysis (ICA) can be implemented by fastICA, which has the advantage of fast convergence and is easy to use. However, the fastICA is based on a gradient algorithm that starts with one random matrix, as a single point in the Probability Density Function (PDF) of the model. In the scenario where the model involves many highly non-linear inputs, the fastICA would face a local maxima problem, and consequently the algorithm would be confined to search in a much smaller sub-set of the multi-dimensional parameter space rather than in the whole parameter space. A method for improving fastICA method in extracting independent components (ICs) from the original mixed signals, based on Genetic Algorithms (geneticICA) was also designed. The geneticICA, which implemented the fastICA using the Genetic Algorithm, could avoid the local maxima problem by using a number of starting random matrices as multi-points in the PDF of the model, and searching for the best result in all of the sub-set parameter spaces. Overall, geneticICA_ANN was more accurate than fastICA_ANN, which produced the highest prediction accuracy of all chemometric methods compared, and many of the other pattern recognition methods. Simulation data has proved that geneticICA has stronger robustness for providing independent information to ANN for further prediction. Even with high dimensional non-linear input data, geneticICA was still able to extract ICs for Neural Network prediction with significant accuracy and robustness.

As described, the Electronic Tongue system was applied to monitor water quality and control a fertigation system. Currently, for online in situ monitoring of irrigation water qualities only gross information such as: pH, electrical conductivity, total dissolve salt content are available for measured, and individual components of the nutrient solution cannot be commonly monitored. In our study, all the essential macro-elements in irrigation water such as ammonium, calcium, chloride, dihydrogen phosphate, nitrate, potassium and sodium were simultaneously determined with acceptable errors. The results were acquired rapidly and accurately, which can be fully employed agronomy and horticulture and serve as a real time nutrient monitoring system for many vegetable crops and analyze irrigation water quality. This could significantly enhance the commercial potential of this tool in the medium- to long-term. Meanwhile, this can also be applied for the natural environment area as a tool for waste water management and nutrient monitoring system for freshwater waterways and reservoirs.

Those skilled in the art will appreciate that the invention described herein is susceptible to variations and modifications other than those specifically described. It is to be understood that the invention includes all such variations and modifications. For example, the described methods can be extended to simultaneously detecting and monitoring multiple contaminants using a variety of different sensor arrays. Furthermore, a database may be constructed based on the knowledge of the features produced from individual chemical interactions with certain sensor arrays to detect and evaluate concentrations of known mixed chemicals. It is now well recognized that a better acceptance of the risk-based approach to manage contaminations, and this requires more sensitive, precise, and accurate analytical techniques that can monitor contaminants in land, water, and air. It also requires a sound understanding of the fate and behavior of chemicals in the environment. Resources and manufacturing industries must also continually improve, develop or modify existing analytical techniques for monitoring and production to be competitive in the world market, as well as control their waste discharges as regulations require. Therefore, new analytical tools able to work in situ and have real-time, autonomous monitoring for all kinds of contaminations and nutrients are of prime importance. These ET systems will also lead to the development of Electronic Nose (EN) systems, which are based on a gas sensor array and can also employ pattern recognition methods, as described, to monitor air pollutants.

The invention claimed is:

1. A method of assessing concentration of at least one analyte ion in a liquid, the method including:
    contacting the liquid with a plurality of electrodes, each of which is configured to generate a signal in response to sensing a selected ion in the liquid;
    receiving the signal from each of the electrodes;
    processing the signal from each of the electrodes using a neural network algorithm residing on a processor that has been trained to calculate ion interference between the selected ion and other ions in the liquid sensed at one of the electrodes and electrode interference between ones of the electrodes sensing a same selected ion based on a result of a comparison of training data indicative of a known ionic concentration applied to the neural network algorithm and the known ionic concentration;
    processing data of the signal from one or more of the electrodes with a genetic Independent Component Analysis (geneticICA) algorithm into Independent Components (ICs) and providing the ICs as input data for the neural network algorithm, wherein the geneticICA algorithm is based on a genetic algorithm using a number of random points in a Probability Distribution Function (PDF) of the data;
    compensating said ion interference and for said electrode interference; and
    assessing the concentration of the at least analyte ion in the liquid on the basis of a compensated output from the neural network algorithm.

2. The method of claim 1, wherein the neural network includes an artificial neural network supported by the geneticICA algorithm.

3. The method of claim 1, wherein the neural network includes a Back-propagation Feed-forward Neural Network (BPNN).

4. The method of claim 1, wherein the method further includes training the neural network algorithm by:
    contacting a training sample of said known ionic concentration with the plurality of electrodes;
    receiving a signal from each of the electrodes;
    providing the signal from each of the electrodes as training data for the neural network algorithm;
    comparing output data from the neural network algorithm with the known ionic concentration of the training sample; and
    adjusting weights in the neural network algorithm based on a result of the comparison.

5. The method of claim 4, wherein training the neural network algorithm includes using an orthogonal experimental design to reduce a number of training samples required to adequately train the neural network.

6. The method of claim 1, wherein the at least one analyte ion includes an ion including an element or compound including sodium, copper, iron, lead, cadmium, magnesium, calcium, potassium, ammonium, nitrate, phosphate, phosphorus, chloride, sulphate and/or sulfur.

7. The method of claim 1, wherein the concentration of the at least one analyte ion is between $10^{-1}$ M and $10^{-5}$ M.

8. The method of claim 1, wherein the data of the signal is non-linear and the geneticICA algorithm avoids a local maxima problem associated with providing the ICs with Independent Component Analysis based on applying a gradient algorithm on non-linear input data.

9. A device for assessing the concentration of an analyte ion in a liquid, the device including:
    a plurality of electrodes each of which generate a signal in response to sensing a selected ion in the liquid; and
    a data processing unit implementing a neural network algorithm that has been trained to calculate ion interference between the selected ion and other ions in the liquid sensed at one of the electrodes and electrode interference between ones of the electrodes sensing a same selected ion based on a result of a comparison of training data indicative of a known ionic concentration applied to the neural network algorithm and the known ionic concentration,
    wherein the signal generated by each of the electrodes is received by the data processing unit and is processed by the neural network algorithm,
    wherein the data processing unit further includes a genetic Independent Component Analysis (geneticICA) algorithm for processing data of the signal into Independent Components (ICs) for input into the neural network algorithm, wherein the geneticICA algorithm is based on a genetic algorithm using a plurality of random points in a Probability Distribution Function (PDF) of the data,
    and wherein the data processing unit compensates for said ion interference and said electrode interference and assesses the concentration of the at least one analyte ion in the liquid on the basis of a compensated output from the neural network algorithm.

10. The device of claim 9, wherein the device further includes a control system that controls operation of one or more of the electrodes, and/or the data processing unit,
wherein the control system controls periodic sampling of a liquid and/or periodic assessment of the concentration of said at least one analyte ion in the liquid.

11. The device of claim 9, further including signal transmitters associated with each of the electrodes, wherein the signal transmitters include one or more of: a signal amplifier; a low pass signal filter; a signal multiplexer; and an analog/digital converter.

12. The device of claim 9, wherein one or more of the electrodes generate a signal in response to said at least one ion including an element or compound including sodium, copper, iron, lead, cadmium, magnesium, calcium, potassium, ammonium, nitrate, phosphate, phosphorus, chloride, sulphate and/or sulfur.

13. The device of claim 9, wherein the neural network algorithm includes a Back-propagation Feed-forward Neural Network (BPNN).

14. The device of claim 9, wherein the neural network includes an artificial neural network supported by the geneticICA algorithm.

15. The device of claim 9, wherein the data of the signal is non-linear and the geneticICA algorithm avoids a local maxima problem associated with providing the ICs with Independent Component Analysis based on applying a gradient algorithm on non-linear input data.

\* \* \* \* \*